(12) United States Patent
Borgström et al.

(10) Patent No.: US 10,577,315 B2
(45) Date of Patent: Mar. 3, 2020

(54) COMPOSITIONS AND METHODS FOR TREATMENT OF PROSTATE CARCINOMA

(71) Applicant: Pellficure Pharmaceuticals, Inc., La Jolla, CA (US)

(72) Inventors: Per Borgström, La Jolla, CA (US); Adrian Chrastina, Chula Vista, CA (US); Veronique Therese Baron, Carlsbad, CA (US); Parisa Abedinpour, San Diego, CA (US)

(73) Assignee: PELLFICURE PHARMACEUTICALS, INC., La Jolla, CA (US)

( * ) Notice: Subject to any disclaimer, the term of this patent is extended or adjusted under 35 U.S.C. 154(b) by 0 days.

(21) Appl. No.: 16/146,225

(22) Filed: Sep. 28, 2018

(65) Prior Publication Data
US 2019/0169122 A1    Jun. 6, 2019

Related U.S. Application Data

(63) Continuation of application No. 15/508,391, filed as application No. PCT/US2015/049831 on Sep. 11, 2015, now Pat. No. 10,093,620.
(Continued)

(51) Int. Cl.
| | |
|---|---|
| *C07C 323/61* | (2006.01) |
| *A61K 31/105* | (2006.01) |
| *A61K 31/122* | (2006.01) |
| *A61K 31/05* | (2006.01) |
| *A61K 31/135* | (2006.01) |
| *A61K 31/136* | (2006.01) |
| *A61K 31/137* | (2006.01) |
| *A61K 31/165* | (2006.01) |
| *A61K 31/167* | (2006.01) |
| *A61K 31/18* | (2006.01) |
| *A61K 31/222* | (2006.01) |
| *A61K 31/235* | (2006.01) |
| *A61K 31/277* | (2006.01) |
| *A61K 31/325* | (2006.01) |
| *A61K 31/4164* | (2006.01) |
| *A61K 31/4166* | (2006.01) |
| *A61K 31/45* | (2006.01) |
| *A61K 31/496* | (2006.01) |
| *A61K 31/56* | (2006.01) |
| *A61K 31/573* | (2006.01) |
| *A61K 31/58* | (2006.01) |
| *A61K 31/661* | (2006.01) |
| *C07C 50/32* | (2006.01) |
| *C07C 69/63* | (2006.01) |
| *C07C 69/92* | (2006.01) |
| *C07C 205/36* | (2006.01) |

(Continued)

(52) U.S. Cl.
CPC ............ *C07C 323/61* (2013.01); *A61K 31/05* (2013.01); *A61K 31/105* (2013.01); *A61K 31/122* (2013.01); *A61K 31/135* (2013.01); *A61K 31/136* (2013.01); *A61K 31/137* (2013.01); *A61K 31/165* (2013.01); *A61K 31/167* (2013.01); *A61K 31/18* (2013.01); *A61K 31/222* (2013.01); *A61K 31/235* (2013.01); *A61K 31/277* (2013.01); *A61K 31/325* (2013.01); *A61K 31/4164* (2013.01); *A61K 31/4166* (2013.01); *A61K 31/45* (2013.01); *A61K 31/496* (2013.01); *A61K 31/56* (2013.01); *A61K 31/573* (2013.01); *A61K 31/58* (2013.01); *A61K 31/661* (2013.01); *C07C 50/32* (2013.01); *C07C 69/63* (2013.01); *C07C 69/92* (2013.01); *C07C 205/36* (2013.01); *C07C 217/60* (2013.01); *C07C 225/30* (2013.01); *C07C 233/23* (2013.01); *C07C 233/25* (2013.01); *C07C 271/46* (2013.01); *C07C 311/16* (2013.01); *C07C 311/51* (2013.01)

(58) Field of Classification Search
CPC .... C07C 323/61; A61K 31/105; A61K 31/122
See application file for complete search history.

(56) References Cited

U.S. PATENT DOCUMENTS

| | | |
|---|---|---|
| 5,491,161 A | 2/1996 | Janssen et al. |
| 8,236,962 B2 | 8/2012 | Hoekstra et al. |

(Continued)

FOREIGN PATENT DOCUMENTS

| | | |
|---|---|---|
| EP | 0288053 A1 | 10/1988 |
| EP | 0413270 A2 | 2/1991 |

(Continued)

OTHER PUBLICATIONS

Acharya et al., "The natural naphthoquinone plumbagin exhibits antiproliferative activity and disrupts the microtubule network through tubulin binding," Biochem, 47(3):7838-45, 2008.

(Continued)

*Primary Examiner* — Pancham Bakshi
(74) *Attorney, Agent, or Firm* — Knobbe, Martens, Olson & Bear LLP

(57) ABSTRACT

Disclosed herein are 1,4-naphthoquinone analogs, pharmaceutical compositions that include one or more of such 1,4-naphthoquinone analogs, and methods of treating and/or ameliorating diseases and/or conditions associated with a cancer, such as prostate cancer with such 1,4-naphthoquinone analogs. Also included are combination therapies wherein a 1,4-naphthoquinone analog disclosed herein, and a hormone therapy agent are provided to a subject suffering from a condition such as cancer.

13 Claims, 13 Drawing Sheets

Related U.S. Application Data

(60) Provisional application No. 62/049,974, filed on Sep. 12, 2014.

(51) Int. Cl.

| | | |
|---|---|---|
| *C07C 217/60* | (2006.01) | |
| *C07C 225/30* | (2006.01) | |
| *C07C 233/23* | (2006.01) | |
| *C07C 233/25* | (2006.01) | |
| *C07C 271/46* | (2006.01) | |
| *C07C 311/16* | (2006.01) | |
| *C07C 311/51* | (2006.01) | |

(56) References Cited

U.S. PATENT DOCUMENTS

| | | |
|---|---|---|
| 8,263,635 B2 | 9/2012 | Bock et al. |
| 9,132,105 B2 | 9/2015 | Borgström |
| 9,655,868 B2 | 5/2017 | Borgström |
| 9,745,261 B2 | 8/2017 | Faloon |
| 10,093,620 B2 * | 10/2018 | Borgstrom ........... A61K 31/105 |
| 2010/0305078 A1 | 12/2010 | Schotzinger et al. |
| 2013/0219528 A1 | 8/2013 | Borgström |
| 2016/0022606 A1 | 1/2016 | Borgström |
| 2017/0258744 A1 | 9/2017 | Borgström |

FOREIGN PATENT DOCUMENTS

| | | |
|---|---|---|
| EP | 0724591 A1 | 8/1996 |
| WO | WO 92/15404 | 9/1992 |
| WO | WO 199320097 | 10/1993 |
| WO | WO 199427989 | 12/1994 |
| WO | WO 199509157 | 4/1995 |
| WO | WO 199614090 | 5/1996 |
| WO | WO 199700257 | 1/1997 |
| WO | WO 199918075 | 4/1999 |
| WO | WO 199954309 | 10/1999 |
| WO | WO 2003027085 | 4/2003 |
| WO | WO 2011130692 | 10/2011 |
| WO | WO 2012018948 | 2/2012 |
| WO | WO 2014158875 | 10/2014 |
| WO | WO 2016040896 | 3/2016 |

OTHER PUBLICATIONS

Bolognesi (Bioorganic and Medicinal Chemistry Letters 18 (2008) 2272-2276).

Kaku et al., "Discovery of orteronel (TAK-700), a naphthylmethylimidazole derivative, as a highly selective 17,20-lyase inhibitor with potential utility in the treatment of prostate cancer," Bioorg Med Chem, 19:6383-99, 2011.

Kanda et al., "Histone-GFP Fusion Protein Enables Sensitive Analysis of Chromosome Dynamics in Living Mammalian Cells," Curr Biol, 8(7):377-85, 1998.

Schweizer et al., "Abiraterone and other novel androgen-directed strategies for the treatment of prostate cancer: a new era of hormonal therapies is born," Ther Adv Urol, 4(4):167-178, 2012.

International Search Report and Written Opinion dated Feb. 18, 2016, issued in International Application No. PCT/US2015/049831, filed Sep. 11, 2015.

* cited by examiner

COMPOSITIONS AND METHODS FOR TREATMENT OF PROSTATE CARCINOMA

CROSS-REFERENCE TO RELATED APPLICATIONS

This application is a continuation application of U.S. application Ser. No. 15/508,391, filed on Mar. 2, 2017, which is a U.S. National Phase Application of PCT International Application Number PCT/US2015/049831, filed on Sep. 11, 2015, designating the United States of America and published in the English language, which is an International Application of and claims the benefit of priority to U.S. Provisional Application No. 62/049,974 filed Sep. 12, 2014, the disclosures of which are hereby expressly incorporated by reference in their entireties.

FIELD OF THE INVENTION

Aspects of the present application relate to the fields of chemistry, biochemistry and medicine. More particularly, disclosed herein are novel 1,4-naphthoquinone analogs, pharmaceutical compositions that include one or more of such 1,4-naphthoquinone analogs, and methods of treating and/or ameliorating diseases and/or conditions associated with a cancer, such as prostate cancer with such 1,4-naphthoquinone analogs. Also included are combination therapies, wherein a 1,4-naphthoquinone analog disclosed herein, and a hormone therapy agent, such as a hormonal ablation compound, are provided to a subject having a cancer, such as a prostate cancer.

BACKGROUND

Prostate cancer develops in the prostate and is typically slow growing; however, some prostate cancers are aggressive. Prostate cancer cells are typically androgen/testosterone/DHT dependent and may metastasize from the prostate to other parts of the body, particularly the bones and lymph nodes. Treatment options for prostate cancer that remains within the prostate include watchful waiting/active surveillance, external beam radiation therapy, brachytherapy, cryosurgery, high-intensity focused ultrasound (HIFU), and surgery. Hormonal therapy and chemotherapy are often reserved for disease that has spread beyond the prostate. However, there are exceptions in that radiation therapy may be used for some advanced tumors, and hormonal therapy may be used for some early stage tumors.

After one to three years of hormonal therapy, it is common that prostate cancer cells resume growth despite the androgen/testosterone/DHT blockade. Previously referred to as "hormone-refractory prostate cancer" or "androgen-independent prostate cancer," the term castration-resistant prostate cancer (CRPC) is now commonly used. Chemotherapeutic agents and immunotherapy have been shown to prolong survival after CRPC but the survival benefit is limited. Despite the efforts of many, the need for more cancer treatments, in particular prostate cancer treatments, is manifest.

SUMMARY

Some alternatives disclosed herein relate to a compound of Formula (I) or a pharmaceutically acceptable salt thereof. Some alternatives disclosed herein relate to a compound of Formula (II) or a pharmaceutically acceptable salt thereof. Some alternatives disclosed herein relate to a compound of Formula (III) or a pharmaceutically acceptable salt thereof. Some alternatives disclosed herein relate to a compound of Formula (IV) or a pharmaceutically acceptable salt thereof.

Some alternatives disclosed herein relate to a pharmaceutical composition containing a compound of Formula (I), (II), (III), or (IV), or a pharmaceutically acceptable salt of Formula (I), (II), (III), or (IV), and a hormone therapy agent. The pharmaceutical composition can be used for inhibiting and/or delaying prostate cancer cell growth and/or the onset of castration-resistant prostate cancer (CRPC) and/or for inhibiting or delaying progression of stage I prostate cancer to stage II prostate cancer and/or for inhibiting or delaying progression of stage II prostate cancer to stage III prostate cancer, and/or for inhibiting or delaying progression of stage III prostate cancer to stage IV prostate cancer and/or for inhibiting or delaying progression of stage IV prostate cancer and/or for inhibiting or delaying the onset of metastasis after the onset of prostate cancer. The pharmaceutical composition can be used for decreasing prostate tumor size. The hormone therapy agent can be selected from cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butyl-benzene-sulfonamide, 3,3'-diindolylmethane, deslorelin, nafarelin, cetrorelix, and ganirelix. In some alternatives, the hormone therapy agent is an agent that reduces the production of testosterone. In some alternatives, the hormone therapy agent inhibits the conversion of testosterone to DHT. In some alternatives, the hormone therapy agent is an agent that reduces the production of testosterone and/or inhibits the conversion of testosterone to DHT. In some alternatives, the hormone therapy agent is not an androgen receptor antagonist. In some alternatives, the hormone therapy agent can be selected from abiraterone, finasteride, diethylstilbestrol (DES), megestrol acetate, fosfestrol, leuprolide, triptorelin, goserelin, histrelin, buserelin, abarelix, degarelix, orteronel, VT-464, ketoconazole, L-39, aminoglutethimide, prochloraz, dutasteride, izonsteride, turosteride, epristeride, equol, deslorelin, nafarelin, cetrorelix, and ganirelix.

Some alternatives disclosed herein relate to a method of inhibiting or delaying the growth of prostate cancer, and/or inhibiting or delaying the onset of castration-resistant prostate cancer (CRPC) and/or for inhibiting or delaying progression of stage I prostate cancer to stage II prostate cancer and/or for inhibiting or delaying progression of stage II prostate cancer to stage III prostate cancer, and/or for inhibiting or delaying progression of stage III prostate cancer to stage IV prostate cancer and/or for inhibiting or delaying progression of stage IV prostate cancer and/or for inhibiting or delaying the onset of metastasis after the onset of prostate cancer by providing a subject having prostate cancer with a therapeutically effective amount of a compound of Formula (I), (II), (III), or (IV), or a pharmaceutically acceptable salt of Formula (I), (II), (III), or (IV), and, optionally, identifying or selecting the subject prior to administration as a subject having prostate cancer or CRPC or stage I, stage II, stage II, or stage IV prostate cancer, and, optionally, determining the inhibition, amelioration, or remission of prostate cancer or CRPC or stage I, stage II, stage III, or stage IV prostate cancer during or after administration. The compound of Formula (I), (II), (III), or (IV), or pharmaceutically acceptable salt thereof, can be administered to the subject in combination with an androgen deprivation therapy. In some alternatives, the androgen deprivation therapy is surgical orchiectomy. In some alternatives, the androgen deprivation therapy can be the administration of a chemical castration agent selected from an anti-androgen compound, an estrogen, a luteinizing hormone-releasing hormone (LHRH) agonist, and a LHRH antagonist or any combination thereof. The androgen deprivation therapy can be the administration of one or more agents selected from cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, episteride, genisterin, gossypol, equol, 18β-glycyrrhetinic acid, altraric acid, N-butylbenzene-sulfonamide, 3,3'-diindolylmethane, deslorelin, nafarelin, cetrorelix, and ganirelix. In some alternatives, the androgen deprivation therapy can be the administration of an agent that reduces the production of testosterone. In some alternatives, the androgen deprivation therapy can be the administration of an agent that inhibits the conversion of testosterone to DHT. In some alternatives, the androgen deprivation therapy can be the administration of an agent that reduces the production of testosterone and/or inhibits the conversion of testosterone to DHT. In some alternatives, the androgen deprivation therapy can be the administration of an androgen deprivation therapy agent that is not an androgen receptor antagonist. In some alternatives, the androgen deprivation therapy can be the administration of an agent selected from abiraterone, finasteride, diethylstilbestrol (DES), megestrol acetate, fosfestrol, leuprolide, triptorelin, goserelin, histrelin, buserelin, abarelix, degarelix, orteronel, VT-464, ketoconazole, L-39, aminoglutethimide, prochloraz, dutasteride, izonsteride, turosteride, episteride, equol, deslorelin, nafarelin, cetrorelix, and ganirelix.

Some alternatives disclosed herein relate to a method of inhibiting or delaying the growth of prostate cancer by providing a subject having prostate cancer with a therapeutically effective amount of a compound of Formula (I), (II), (III), or (IV), or a pharmaceutically acceptable salt of Formula (I), (II), (III), or (IV), while reducing the amount of an androgen in the subject. In some alternatives, the amount of androgen can be reduced by providing the subject with a hormone therapy. In some alternatives, the amount of androgen can be reduced by providing the subject with one or more agents selected from cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, episteride, genisterin, gossypol, equol, 18β-glycyrrhetinic acid, altraric acid, N-butylbenzene-sulfonamide, 3,3'-diindolylmethane, deslorelin, nafarelin, cetrorelix, and ganirelix. In some alternatives, the hormone therapy agent is an agent that reduces the production of testosterone. In some alternatives, the hormone therapy agent inhibits the conversion of testosterone to DHT. In some alternatives, the hormone therapy agent is an agent that reduces the production of testosterone and/or inhibits the conversion of testosterone to DHT. In some alternatives, the hormone therapy agent is not an androgen receptor antagonist. In some alternatives, the hormone therapy agent can be selected from abiraterone, finasteride, diethylstilbestrol (DES), megestrol acetate, fosfestrol, leuprolide, triptorelin, goserelin, histrelin, buserelin, abarelix, degarelix, orteronel, VT-464, ketoconazole, L-39, aminoglutethimide, prochloraz, dutasteride, izonsteride, turosteride, episteride, equol, deslorelin, nafarelin, cetrorelix, and ganirelix.

Some alternatives disclosed herein relate to a method for identifying a compound that inhibits or delays prostate cancer cell growth by providing a pseudo-orthotopic chamber mouse model, where the mouse model has prostate cancer; reducing the level of an androgen in the mouse model; providing the mouse model with a compound of Formula (I), (II), (III), or (IV), or a pharmaceutical salt thereof; and evaluating whether the compound is effective in inhibiting the growth of prostate cancer cells.

Some alternatives disclosed herein relate to a method of inhibiting or delaying the onset of castration resistant prostate cancer (CRPC) by classifying a subject as a member of a population that is at risk for developing CRPC and providing the subject a therapeutically effective amount of a compound of Formula (I), (II), (III), or (IV), or a pharmaceutical salt thereof.

Some alternatives disclosed herein relate to a method of identifying a compound that inhibits or delays prostate cancer cell growth by contacting prostate cancer cells with a compound of Formula (I), (II), (III), or (IV), or a pharmaceutical salt thereof, in the absence of androgen; determining the presence or absence of an inhibition or delay in prostate cancer cell growth; and classifying the compound into a population that inhibits or delays prostate cancer cell growth in the absence of androgen, or into a population that does not inhibit or delay prostate cancer cell growth. Some alternatives disclosed herein relate to a method of identifying a compound that inhibits or delays prostate cancer cell growth by contacting prostate cancer cells with a compound of Formula (I), (II), (III), or (IV), or a pharmaceutical salt thereof, and with androgen concentrations at or below the concentrations of the average surgically castrated male subject; determining the presence or absence of an inhibition or delay in prostate cancer cell growth; and classifying the compound into a population that inhibits or delays prostate cancer cell growth with androgen concentrations at or below the concentrations of the average surgically castrated male subject, or into a population that does not inhibit or delay prostate cancer cell growth. Some alternatives disclosed herein relate to a method of identifying a compound that inhibits or delays prostate cancer cell growth by contacting prostate cancer cells with a compound of Formula (I), (II), (III), or (IV), or a pharmaceutical salt thereof, and with testosterone concentration at ≤20 ng/dL; determining the presence or absence of an inhibition or delay in prostate cancer cell growth; and classifying the compound into a population that inhibits or delays prostate cancer cell growth with testosterone concentration at ≤20 ng/dL, or into a population that does not inhibit or delay prostate cancer cell growth. Some alternatives disclosed herein relate to a method of identifying a compound that inhibits or delays prostate cancer cell growth by contacting prostate cancer cells with a compound of Formula (I), (II), (III), or (IV), or a pharmaceutical salt thereof, and with a 5-alpha reductase inhibitor; determining the presence or absence of an inhibition or delay in prostate cancer cell growth; and classifying the compound into a population that inhibits or delays prostate cancer cell growth in combination with a 5-alpha reductase inhibitor, or into a population that does not inhibit or delay prostate cancer cell growth.

Some alternatives disclosed herein relate to a method of making a prostate cancer therapeutic by contacting prostate cancer cells with a compound of Formula (I), (II), (III), or (IV), in the absence of androgen; determining the presence or absence of an inhibition or delay in prostate cancer cell growth; from said one or more compounds, selecting a compound that inhibits prostate cancer cell growth in the absence of androgen; and formulating the compound that inhibits or delays prostate cancer cell growth in the absence of androgen for administration to a subject suffering from prostate cancer. Some alternatives disclosed herein relate to a method of making a prostate cancer therapeutic by contacting prostate cancer cells with a compound of Formula (I), (II), (III), or (IV), with androgen concentrations at or below the concentrations of the average surgically castrated male subject; determining the presence or absence of an inhibition or delay in prostate cancer cell growth; from said one or more compounds, selecting a compound that inhibits prostate cancer cell growth with androgen concentrations at or below the concentrations of the average surgically castrated male subject; and formulating the compound that inhibits or delays prostate cancer cell growth with androgen concentrations at or below the concentrations of the average surgically castrated male subject for administration to a subject suffering from prostate cancer. Some alternatives disclosed herein relate to a method of making a prostate cancer therapeutic by contacting prostate cancer cells with a compound of Formula (I), (II), (III), or (IV), with testosterone concentration at ≤20 ng/dL; determining the presence or absence of an inhibition or delay in prostate cancer cell growth; from said one or more compounds, selecting a compound that inhibits prostate cancer cell growth with testosterone concentration at ≤20 ng/dL; and formulating the compound that inhibits or delays prostate cancer cell growth with testosterone concentration at ≤20 ng/dL for administration to a subject suffering from prostate cancer. Some alternatives disclosed herein relate to a method of making a prostate cancer therapeutic by contacting prostate cancer cells with a compound of Formula (I), (II), (III), or (IV), and with a 5-alpha reductase inhibitor; determining the presence or absence of an inhibition or delay in prostate cancer cell growth; from said one or more compounds, selecting a compound that inhibits prostate cancer cell growth in combination with a 5-alpha reductase inhibitor; and formulating the compound that inhibits or delays prostate cancer cell growth in combination with a 5-alpha reductase inhibitor for administration to a subject suffering from prostate cancer.

DETAILED DESCRIPTION

I. Definitions

Figure 1:
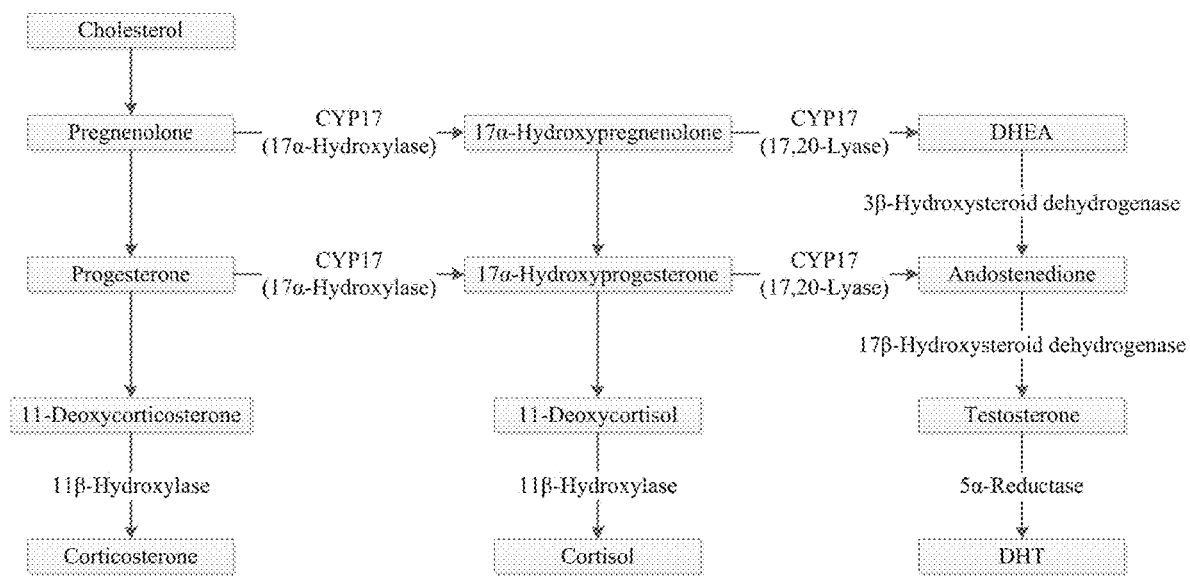
FIG. 1 illustrates a typical steroid/androgen synthesis pathway.
Figure 2A:
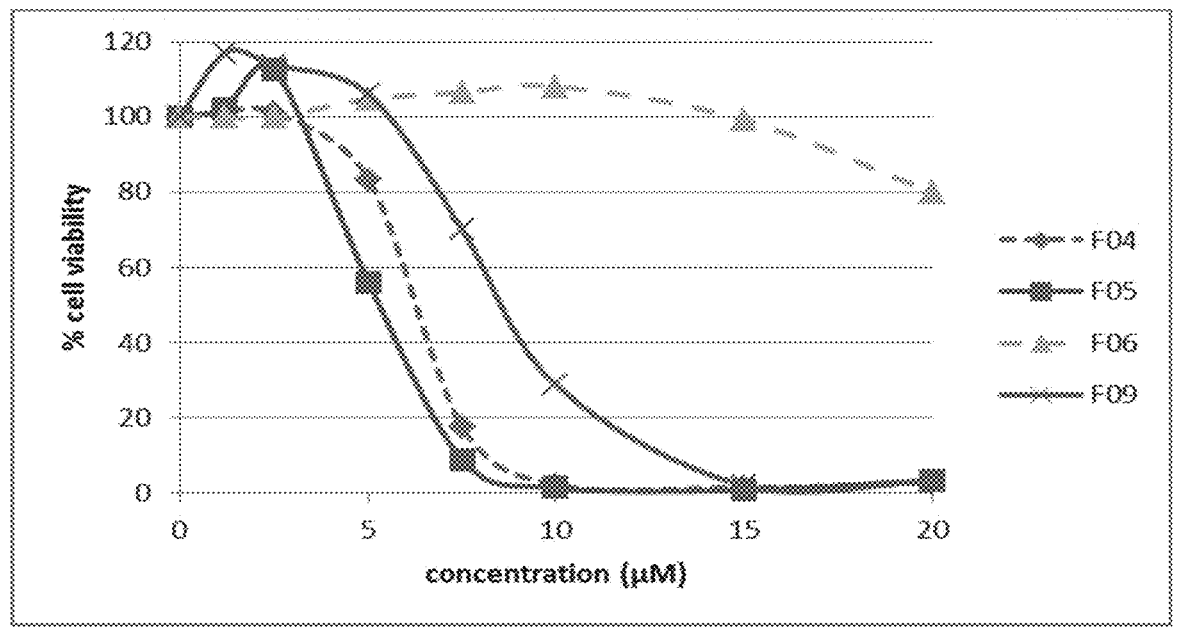
FIGS. 2A-2E summarize results of cytotoxicity assays performed to evaluate the effects of 1,4-naphthoquinone analogs on the proliferation of PTEN-P2 mouse prostate cancer cells. The X axis depicts drug concentrations (μM) used in each of the treatments. The Y axis depicts the percentage of cell viability observed in each of the treatments.
Figure 2B:
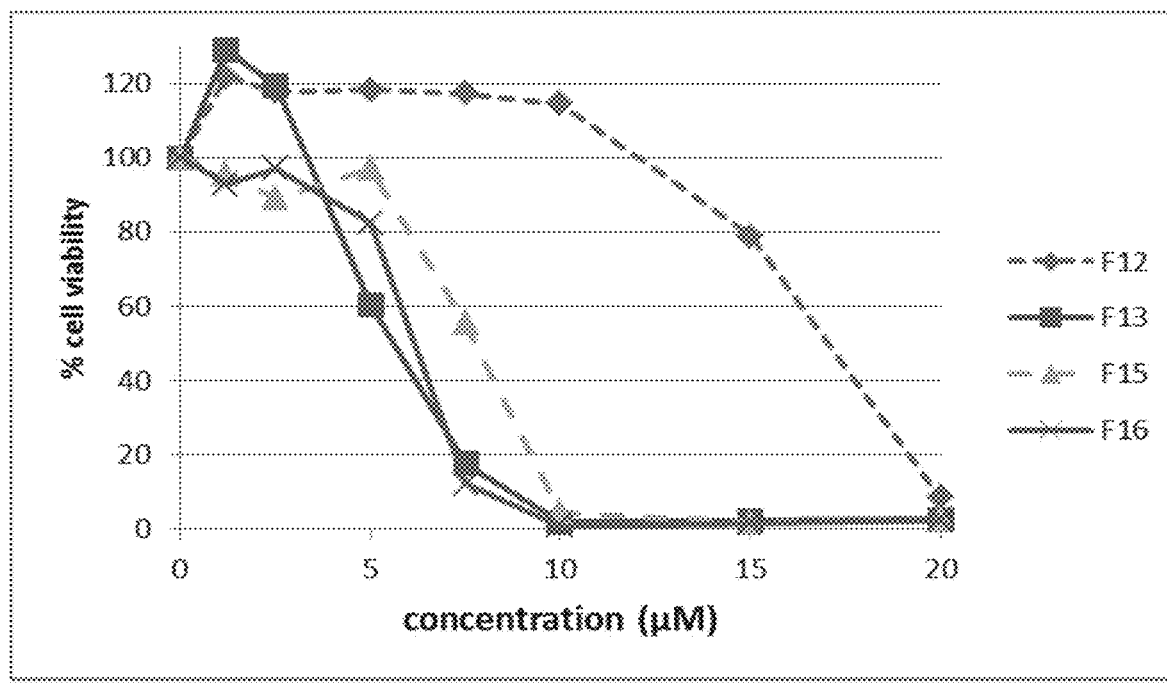
Figure 2C:
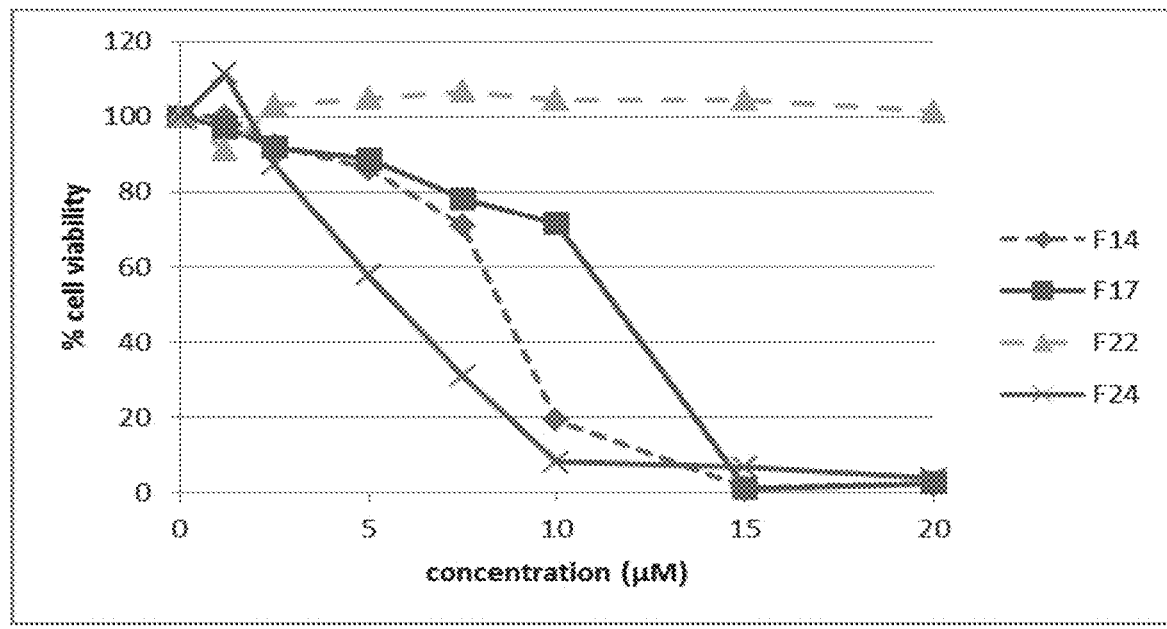
Figure 2D:
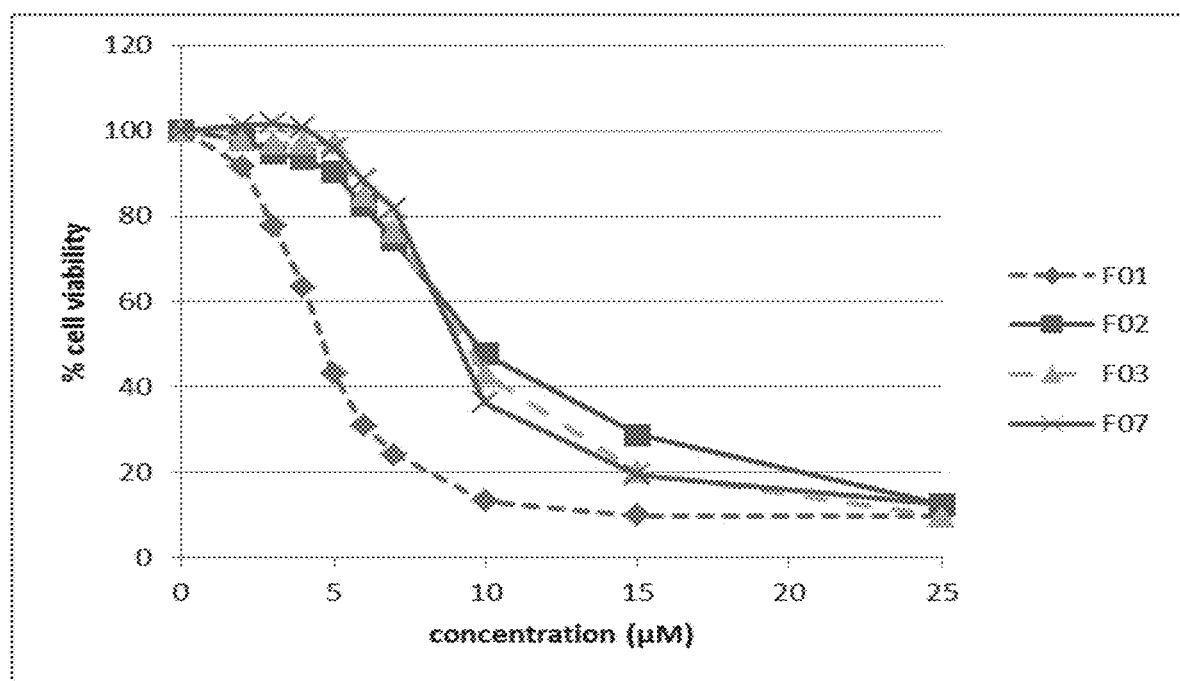
Figure 2E:
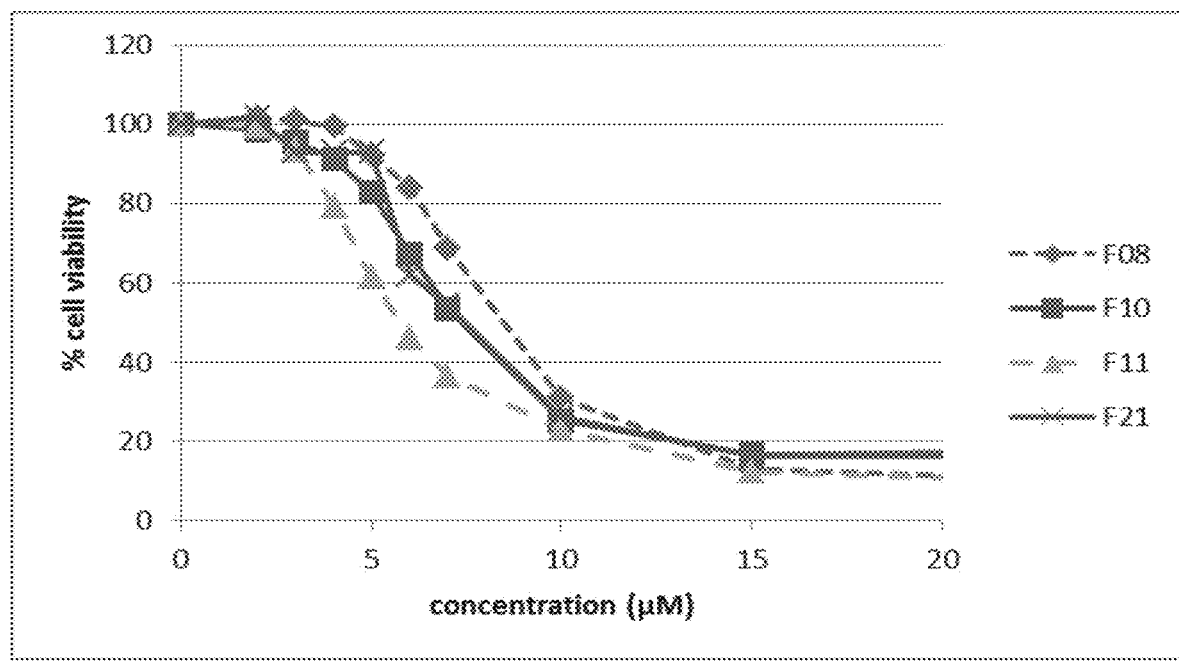
Figure 3A:
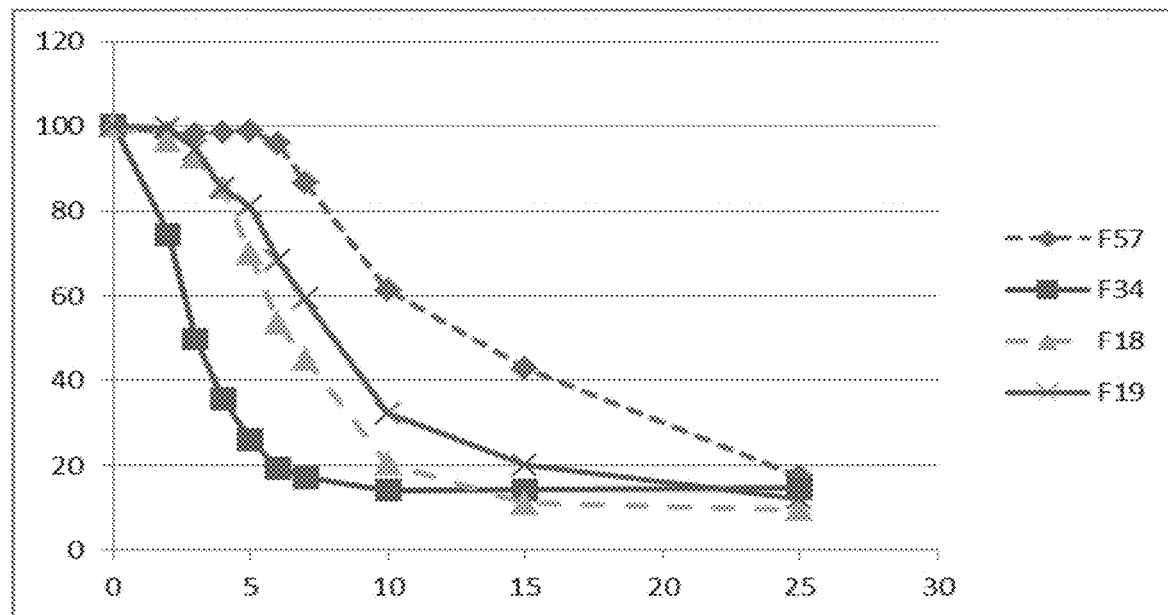
FIGS. 3A-3D summarize results of cytotoxicity assays performed to evaluate the effects of 1,4-naphthoquinone analogs on the proliferation of PTEN-P2 mouse prostate cancer cells. The X axis depicts drug concentrations (μM) used in each of the treatments. The Y axis depicts the percentage of cell viability observed in each of the treatments.
Figure 3B:
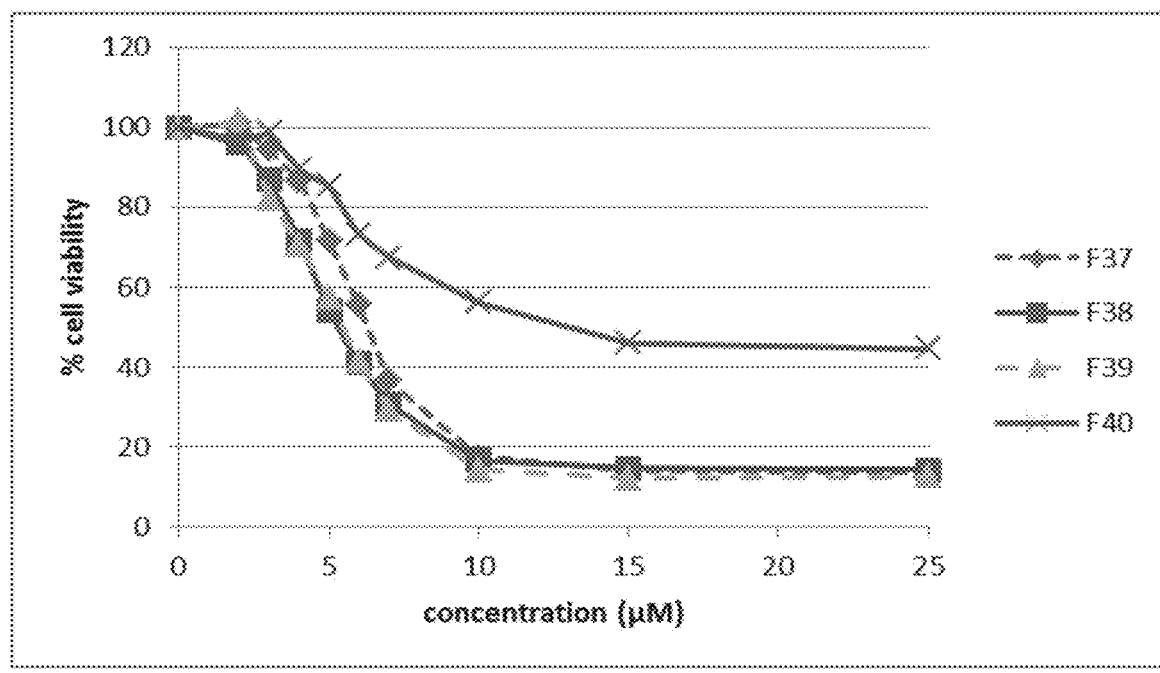
Figure 3C:
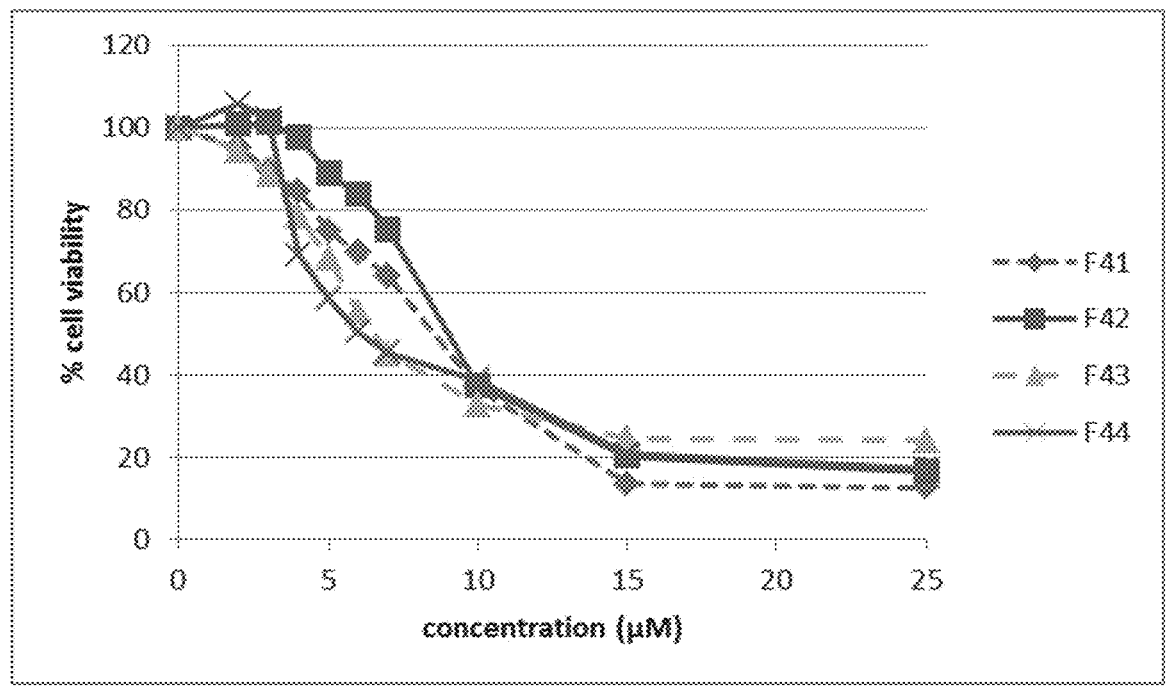
Figure 3D:
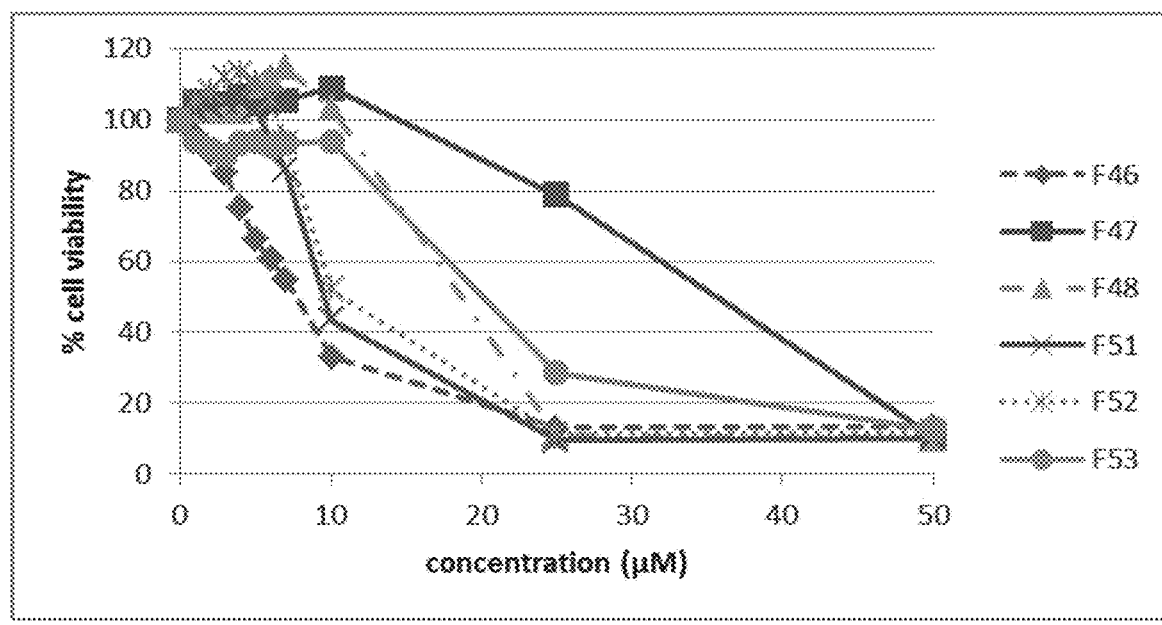

Unless defined otherwise, all technical and scientific terms used herein have the same meaning as is commonly understood by one of ordinary skill in the art. All patents, applications, published applications and other publications referenced herein are expressly incorporated by reference in their entireties unless stated otherwise. In the event that there are a plurality of definitions for a term herein, those in this section prevail unless stated otherwise.

As used herein, any "R" group(s) such as, without limitation, R, $R^1$, $R^2$, $R^3$, $R^4$, $R^5$, $R^6$, $R^7$, $R^8$, $R^9$, $R^{10}$, $R^{11}$, $R^{12}$, and $R^{13}$ represent substituents that can be attached to the indicated atom. An R group may be substituted or unsubstituted.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "a"

to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl or alkenyl group, the broadest range described in these definitions is to be assumed.

As used herein, the term "abarelix" refers to abarelix and pharmaceutically acceptable salts thereof, including acetyl-D-β-naphthylalanyl-D-4-chlorophenylalanyl-D-3-pyridyl-alanyl-L-seryl-L-N-methyl-tyrosyl-D-asparagyl-L-leucyl-L-N(ε)-isopropyl-lysyl-L-prolyl-D-alanyl-amide. Abarelix can include Plenaxis™.

As used herein, the term "abiraterone" refers to abiraterone and pharmaceutically acceptable salts thereof, including abiraterone acetate. Abiraterone includes Abretone and ZYTIGA™. Abiraterone includes (3β)-17-(pyridin-3-yl)androsta-5,16-dien-3-ol. Abiraterone includes Abretone and ZYTIGA®.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. An alkenyl group may be unsubstituted or substituted.

As used herein, the term "altraric acid" refers to altraric acid and pharmaceutically acceptable salts thereof, including D-altraric acid and (S)-2-methylpiperazine. Altraric acid includes (2S,3R,4S,5S)-2,3,4,5-tetrahydroxyhexanedioic acid.

As used herein, the term "aminoglutethimide" refers to aminoglutethimide and pharmaceutically acceptable salts thereof, including CYTADREN®, aminoglutethimide, d-Aminoglutethimide L-tartrate, and R-(+)-p-Aminoglutethimide (+)-tartrate salt. Aminoglutethimide includes (RS)-3-(4-aminophenyl)-3-ethyl-piperidine-2,6-dione.

As used herein, the term "ARN-509" refers to ARN-509 and pharmaceutically acceptable salts thereof, including JNJ-56021927 and A52. ARN-509 includes 4-(7-(6-cyano-5-(trifluoromethyl)pyridin-3-yl)-8-oxo-6-thioxo-5,7-diazaspiro[3.4]octan-5-yl)-2-fluoro-N-methylbenzamide).

As used herein, "aralkyl" refers to an aryl group connected, as a substituent, via a lower alkylene group. The lower alkylene and aryl group of an aralkyl may be substituted or unsubstituted. Examples include but are not limited to benzyl, phenylalkyl, and naphthylalkyl. An aralkyl group may be substituted or unsubstituted.

As used herein, "aralkyloxy" refers to an aryl group connected, as a substituent, via a lower alkoxy group. Examples include but are not limited to benzyloxy, phenylalkyloxy, and naphthylalkyloxy. An aralkyloxy group may be substituted or unsubstituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, phenyl, tolyl, xylyl, mesityl, naphthyl, ethylphenyl, t-butylphenyl, and isopropylphenyl, benzene, naphthalene and azulene. An aryl group may be substituted or unsubstituted.

As used herein, the term "bicalutamide" refers to bicalutamide and pharmaceutically acceptable salts thereof, including BICALOX®, CASODEX®, COSUDEX®, Calutide, and Kalumid. Bicalutamide includes N-[4-cyano-3-(trifluoromethyl)phenyl]-3-[(4-fluorophenyl)sulfonyl]-2-hydroxy-2-methylpropanamide.

As used herein, the term "buserelin" refers to buserelin and pharmaceutically acceptable salts thereof, including buserelin acetate. Beserelin includes Bigonist, SUPRADOPIN®, SURFACT®, Profact, Etilamide, and Tiloryth. Buserelin includes (2S)—N-[(2S)-1-[[(2S)-1-[[(2S)-1-[[(2S)-1-[[(2R)-1-[[(2S)-1-[[(2S)-5-(diaminomethylideneamino)-1-[(2S)-2-(ethylcarbamoyl)pyrrolidin-1-yl]-1-oxopentan-2-yl]amino]-4-methyl-1-oxopentan-2-yl]amino]-3-[(2-methylpropan-2-yl)oxy]-1-oxopropan-2-yl]amino]-3-(4-hydroxyphenyl)-1-oxopropan-2-yl]amino]-3-hydroxy-1-oxopropan-2-yl]amino]-3-(1H-indol-3-yl)-1-oxopropan-2-yl]amino]-3-(1H-imidazol-5-yl)-1-oxopropan-2-yl]-5-oxopyrrolidine-2-carboxamide.

As used herein, a "carrier" refers to a compound that facilitates the incorporation of a compound into cells or tissues. Exemplary carriers include, but are not limited to, water, saline, buffered saline, dextrose, glycerol, ethanol, partial glyceride mixtures of saturated and unsaturated vegetable fatty acids, waxes, polyethylene-polyoxypropylene-block polymers, starches such as corn starch and potato starch, and combinations thereof.

As used herein, the term "cetrorelix" refers to cetrorelix and pharmaceutically acceptable salts thereof, including cetrorelix acetate. Cetrorelix includes acetyl-D-3-(2'-naphtyl)-alanine-D-4-chlorophenylalanine-D-3-(3'-pyridyl)-alanine-L-serine-L-tyrosine-D-citrulline-L-leucine-L-arginine-L-proline-D-alanine-amide.

As used herein, the term "cyproterone acetate" refers to cyproterone acetate and pharmaceutically acceptable salts thereof, including Androcur and CYPROSTAT®. Cyproterone acetate can include 1R,3aS,3bR,7aR,8aS,8bS,8cS,10aS)-1-acetyl-5-chloro-8b,10a-dimethyl-7-oxo-1,2,3,3a,3b,7,7a,8,8a,8b,8c,9,10,10a-tetradecahydrocyclopenta-[a]cyclopropa-[g]phenanthren-1-yl acetate.

The term "degarelix", as used herein, refers to degarelix and pharmaceutically acceptable salts thereof, including degarelix acetate. Degarelix includes FIRMAGON® (including FIRMAGON® injection). Degarelix includes D-alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4pyrimidinyl]carbonyl]amino]-L-phenylalanyl-4-[(aminocarbonyl)amino]-D-phenylalanyl-L-leucyl-N6-(1-methylethyl)-L-lysyl-L-prolyl.

As used herein, the term "deslorelin" refers to deslorelin and pharmaceutically acceptable salts thereof, including deslorelin acetate. Deslorelin includes SucroMate™ Equine, Ovuplant, and SUPRELORIN®. Deslorelin includes (2S)—N-[(2S)-1-[[(2S)-1-[[(2S)-1-[[(2S)-1-[[(2R)-1-[[(2S)-1-[[(2S)-5-(diaminomethylideneamino)-1-[(2S)-2-(ethylcarbamoyl)pyrrolidin-1-yl]-1-oxopentan-2-yl]amino]-4-methyl-1-oxopentan-2-yl]amino]-3-(1H-indol-3-yl)-1-oxopropan-2-yl]amino]-3-(4-hydroxyphenyl)-1-oxopropan-2-yl]amino]-3-hydroxy-1-oxopropan-2-yl]amino]-3-(1H-indol-3-yl)-1-oxopropan-2-yl]amino]-3-(1H-imidazol-5-yl)-1-oxopropan-2-yl]-5-oxopyrrolidine-2-carboxamide.

As used herein, the term "diethylstilbestrol" refers to diethylstilbestrol and pharmaceutically acceptable salts thereof, including diethylstilbestrol disodium, diethylstilbestrol diphosphate, and Diethylstilbestrol dipropionate. Diethylstilboestrol includes DISTILBENE®, Stilbestrol, and Stilphostrol. Diethylstilbestrol includes 4,4'-(3E)-hex-3-ene-3,4-diyldiphenol.

As used herein, the terms "3,3'-diindolylmethane" and "DIM" refer to 3,3'-diindolylmethane and pharmaceutically acceptable salts thereof, including 5,5'-dichloro-diindolylmethane, dinitro-diindolylmethane, and N,N'-dimethoxy-diindolylmethane. DIM can include 3,3'-methanediylbis(1H-indole), 3-(1H-Indol-3-ylmethyl)-1H-indole, and 3,3'-methylenebis-1H-indole.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, the term "dutasteride" refers to dutasteride and pharmaceutically acceptable salts thereof, including dutasteride acetate. Dutasteride includes Avodart (including Avodart oral). Dutasteride includes (5α,17β)-N-{2,5-bis(trifluoromethyl)phenyl}-3-oxo-4-azaandrost-1-ene-17-carboxamide.

As used herein, the term "enzalutamide" refers to enzalutamide and pharmaceutically acceptable salts thereof. Enzalutamide includes Xtandi (including Xtandi oral). Enzalutamide includes (4-(3-(4-cyano-3-(trifluoromethyl)phenyl)-5,5-dimethyl-4-oxo-2-thioxoimidazolidin-1-yl)-2-fluoro-N-methylbenzamide).

As used herein, the term "episteride" refers to episteride and pharmaceutically acceptable salts thereof. Episteride includes SKF-105,657 and ONO-9302. Episteride includes (17-(tert-butylcarbamoyl)androsta-3,5-diene-3-carboxylic acid), 7β-(tert-butylaminocarbonyl)androsta-3,5-diene-3-carboxylic acid, (17β)-17-[[(1,1-dimethylethyl)amino]carbonyl]androsta-3,5-diene-3-carboxylic acid, and (17b)-17-[[(1,1-dimethylethyl)amino]carbonyl]-androsta-3,5-diene-3-carboxylic acid.

As used herein, the term "equol" refers to equol and pharmaceutically acceptable salts thereof, including (R,S) equol 4'-sulfate sodium salt. Equol includes (S)-equol and (R)-equol. Equol includes (3S)-3-(4-Hydroxyphenyl)-7-chromanol, (4',7-isoflavandiol), 7,4'-dihydroxy-isoflavan, 7-hydroxy-3-(4'-hydroxyphenyl)-chroman, and 3,4-dihydro-3-[4-(sulfooxy)phenyl]-2H-1-benzopyran-7-ol sodium salt.

The term "ethylstilbestrol", as used herein, refers to ethylstilbestrol and pharmaceutically acceptable salts thereof. Ethylstilbestrol includes BRN 3136095 and alpha-ethyl-4,4'-stilbenediol.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

As used herein, the term "finasteride" refers to finasteride and pharmaceutically acceptable salts thereof. Finasteride includes MK-906, Proscar and Propecia. Finasteride includes N-(1,1-dimethylethyl)-3-oxo-(5α,17β)-4-azaandrost-1-ene-17-carboxamide.

As used herein, the term "flutamide" refers to flutamide and pharmaceutically acceptable salts thereof, including hydroxyflutamide and 2-amino-5-nitro-4-(trifluoromethyl)phenol. Flutamide includes Eulexin, Flutamin, Cytomid, Flutamide USP$_{25}$, Cebatrol, Niftholide, and Niftolid. Flutamide includes 2-methyl-N-[4-nitro-3-(trifluoromethyl)phenyl]-propanamide.

As used herein, the term "fosfestrol" refers to fosfestrol and pharmaceutically acceptable salts thereof, including fosfestrol sodium and fosfestrol tetrasodium. Fosfestrol includes fosfestrol, fosfestrolo, Honvan, and Stilbostatin. Fosfestrol includes [4-[4-(4-phosphonooxyphenyl)hex-3-en-3-yl] phenoxy]phosphonic acid and diethylstilbestrol diphosphate.

As used herein, the term "galeterone" refers to galeterone and pharmaceutically acceptable salts thereof. Galeterone includes Tokai TOK-001 and VN/124-1. Galeterone includes (17-(1H-benzimidazol-1-yl)androsta-5,16-dien-3β-ol).

As used herein, the term "ganirelix" refers to ganirelix and pharmaceutically acceptable salts thereof, including ganirelix acetate and ganirelix diacetate. Ganirelix includes Antagon, Cetrotide, Ganirelix, and Orgalutran. Ganirelix includes (2S)-1-[(2S)-2-[[(2S)-2-[[(2R)-2-[[(2R)-2-[[(2S)-2-[[(2R)-2-[[(2R)-2-[[(2R)-2-acetamido-3-naphthalen-2-ylpropanoyl]amino]-3-(4-chlorophenyl)propanoyl]amino]-3-pyridin-3-ylpropanoyl]amino]-3-hydroxypropanoyl]amino]-3-(4-hydroxyphenyl)-propanoyl]amino]-6-[bis(ethylamino)methylideneamino]hexanoyl]-amino]-4-methyl-pentanoyl]amino]-6-[bis(ethylamino)methylideneamino]hexanoyl]-N-[(2R)-1-amino-1-oxopropan-2-yl]pyrrolidine-2-carboxamide.

As used herein, the term "genisterin" refers to genisterin and pharmaceutically acceptable salts thereof. Genisterin includes 5,7-dihydroxy-3-(4-hydroxyphenyl)-1-benzopyran-4-one, and 5,7-dihydroxy-3-(4-hydroxyphenyl)chromen-4-one.

As used herein, the term "18β-glycyrrhetinic acid" refers to 18β-glycyrrhetinic acid and glycyrrhetic acid, and pharmaceutically acceptable salts thereof, including Acetoxolone, Enoxolone, carbenoxolone, and 3β-Hydroxy-11-oxo-18β,20β-olean-12-en-29-oic acid. 18β-Glycyrrhetinic acid can include (2S,4aS,6aS,6bR,8aR,10S,12aS,12bR,14bR)-10-hydroxy-2,4a,6a,6b,9,9,12a-heptamethyl-13-oxo-1,2,3,4,4a,5,6,6a,6b,7,8,8a,9,10,11,12,12a,12b,13,14b-icosahydropicene-2-carboxylic acid.

As used herein, the term "goserelin" refers to goserelin and pharmaceutically acceptable salts thereof, including goserelin acetate. Goserelin includes Zoladex. Goserelin includes N-(21-((1H-indol-3-yl)methyl)-1,1-diamino-12-(tert-butoxymethyl)-6-(2-(2-carbamoylhydrazinecarbonyl)cyclopentanecarbonyl)-15-(4-hydroxybenzyl)-18-(hydroxymethyl)-25-(1H-imidazol-5-yl)-9-isobutyl-8,11,14,17, 20,23-hexaoxo-2,7,10,13,16,19,22-heptaazapentacos-1-en-24-yl)-5-oxopyrrolidine-2-carboxamide.

As used herein, the term "gossypol" refers to gossypol and pharmaceutically acceptable salts thereof, including gossypol acetate and acetyl gossypol. Gossypol includes AT-101, ApoG2, B-gossypol, and D-gossypol. Gossypol includes 2,2'-bis-(formyl-1,6,7-trihydroxy-5-isopropyl-3-methylnaphthalene).

The term "halogen" as used herein, means any one of the radio-stable atoms of column 7 of the Periodic Table of the Elements, such as, fluorine, chlorine, bromine and iodine.

As used herein, the term "histrelin" refers to histrelin and pharmaceutically acceptable salts thereof, including histrelin acetate. Histrelin includes Vantas and Supprelin LA. Histrelin includes 5-oxo-L-prolyl-L-histidyl-L-tryptophyl-L-seryl-L-tyrosyl-1-benzyl-D-histidyl-L-leucyl-N5-(di-aminomethylene)-L-ornithyl-N-ethyl-L-prolinamide.

As used herein, the term "hormone therapy agent" refers to anti-androgens (including steroidal anti-androgens and non-steroidal anti-androgens), estrogens, luteinizing hormone-releasing hormone (LHRH) agonists, and LHRH antagonists, as well as, hormonal ablation therapy. Some hormone therapy agents are compounds that inhibit the synthesis and/or conversion of testosterone, such as orteronel ("testosterone synthesis inhibitors"); whereas, other hormone therapy agents bind to the androgen receptor and thereby inhibit the binding of testosterone to the androgen receptor, such as Casodex ("androgen receptor inhibitor"). Exemplary hormone therapy agents include, but are not limited to, cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, and ganirelix.

As used herein, the term "izonsteride" refers to izonsteride and pharmaceutically acceptable salts thereof. Izonsteride includes ((4aR,10bR)-8-[(4-ethyl-1,3-benzothiazol-2-yl)sulfanyl]-4,10b-dimethyl-1,4,4a,5,6,10b-hexahydrobenzo[f]quinolin-3(2H)-one).

As used herein, the term "ketoconazole" refers to ketoconazole and pharmaceutically acceptable salts thereof, including ketoconazole oxalate. Ketoconazole includes Nizoral, Extina, Xolegel, and Kuric. Ketoconazole includes (1-[4-(4-{[(2R,4S)-2-(2,4-Dichlorophenyl)-2-(1H-imidazol-1-ylmethyl)-1,3-dioxolan-4-yl]methoxy}phenyl)piperazin-1-yl]ethan-1-one).

The term "L-39", as used herein, refers to L-39 and pharmaceutically acceptable salts thereof. L-39 includes L-39 cpd. L-39 includes (17-(5'-Isoxazolyl)androsta-4,16-dien-3-one).

As used herein, the term "leuprolide" refers to leuprolide and pharmaceutically acceptable salts thereof, including leuprolide acetate. Leuprolide includes leuprorelin, Lupron (including Lupron injection and Lupron depot), Viadur, Eligard, and Leupromer. Leuprolide includes 5-oxo-L-prolyl-L-histidyl-L-tryptophyl-L-seryl-L-tyrosyl-D-leucyl-L-leucyl-L-arginyl-N-ethyl-Lprolinamide acetate.

As used herein, the term "megestrol acetate" refers to megestrol acetate and pharmaceutically acceptable salts thereof. Megestrol acetate includes Megace and Megace ES. Megestrol acetate includes 17α-(acetyloxy)6-methylpregna-4,6-diene-3,20-dione.

As used herein, the term "N-butylbenzenesulfonamide" refers to N-butylbenzene-sulfonamide and pharmaceutically acceptable salts thereof. N-butylbenzenesulfonamide includes Plasthall and Plastonomoll. N-butylbenzenesulfonamide includes N-n-butylamide, N-butylbenzenesulfonamide, benzenesulfonic acide, benzenesulfonic acid butyl amide, and N-butylbenzenesulfonamide.

As used herein, the term "nilutamide" refers to nilutamide and pharmaceutically acceptable salts thereof. Nilutamide includes Nilandron and Anandron. Nilutamide includes 5,5-dimethyl-3-[4-nitro-3-(trifluoromethyl)phenyl] imidazolidine-2,4-dione.

As used herein, the term "nafarelin" refers to nafarelin and pharmaceutically acceptable salts thereof, including nafarelin acetate. Nafarelin includes Nacenyl, Synarel, Synrelina, Nafarelina, and (D-2-Nal6)-LHRH Nafarelin. Nafarelin includes (2R)—N-[(2R)-5-carbamimidamido-1-[(2S)-2-[(carbamoylmethyl)-carbamoyl]-pyrrolidin-1-yl]-1-oxopentan-2-yl]-2-[(2R)-2-[(2R)-2-[(2R)-3-hydroxy-2-[(2S)-2-[(2S)-3-(1H-imidazol-4-yl)-2-{[(2R)-5-oxopyrrolidin-2-yl]formamido}propanamido]-3-(1H-indol-3-yl)propanamido]propanamido]-3-(4-hydroxyphenyl)propanamido]-3-(naphthalen-2-yl)propanamido]-4-methylpentanamide.

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxy, trihalomethanesulfonyl, trihalomethanesulfonamido, amino, mono-substituted amino group and di-substituted amino group, and protected derivatives thereof.

The term "1,4-naphthoquinone analog" refers to a compound of Formula (I), (II), (III), or (IV), wherein $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined herein. 1,4-Naphthoquinone analog can also refer to any one or more of the following compounds:

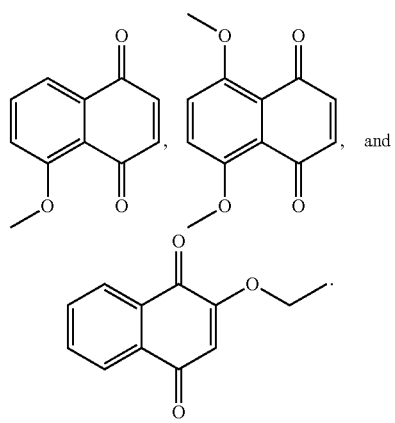

As used herein, the term "orteronel" refers to orteronel and pharmaceutically acceptable salts thereof. Orteronel includes TAK-700. Orteronel includes 6-(7-Hydroxy-6,7-dihydro-5H-pyrrolo[1,2-c]imidazol-7-yl)-N-methyl-naphthalene-2-carboxamide.

The term "pharmaceutically acceptable salt" refers to a salt of a compound that does not cause significant irritation to an organism to which it is administered and does not abrogate the biological activity and properties of the compound. In some alternatives, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be diastereomerically pure, diastereomerically enriched, or may be stereoisomeric mixtures. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

The term "pharmaceutical composition" refers to a mixture of a compound disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid and salicylic acid. Pharmaceutical compositions will generally be tailored to the specific intended route of administration.

The term "physiologically acceptable" defines a carrier, diluent or excipient that does not abrogate the biological activity and properties of the compound.

As used herein, the term "prochloraz" refers to prochloraz and pharmaceutically acceptable salts thereof, including prochloraz amine, prochloraz copper, prochloraz zinc, and prochloraz manganese salts. Prochloraz includes Pesnatal and JMPR 2001. Prochloraz includes (N-propyl-N-[2-(2,4,6-trichlorophenoxy)-ethyl]imidazole-1-carboxamide) and N-propyl-N-[2-(2,4,6-trichlorophenoxy)ethyl]-1H-imidazole-1-carboxamide.

As used herein, a "subject" refers to an animal that is the object of treatment, observation or experiment. "Animal" includes cold- and warm-blooded vertebrates, and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some alternative, the subject is human.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy.

The term "therapeutically effective amount" is used to indicate an amount of an active compound, or pharmaceutical agent, that elicits the biological or medicinal response indicated. For example, a therapeutically effective amount of compound can be the amount needed to prevent, alleviate or ameliorate symptoms of disease or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors that those skilled in the medical arts will recognize.

As used herein, the term "triptorelin" refers to triptorelin and pharmaceutically acceptable salts thereof, including triptorelin acetate and triptorelin pamoate. Triptorelin includes Trelstar, Decapeptyl, Diphereline, Gonapeptyl, and Variopeptyl. Triptorelin includes 5-oxo-D-prolyl-L-histidyl-L-tryptophyl-L-seryl-L-tyrosyl-3-(1H-indol-2-yl)-L-alanyl-leucyl-L-arginyl-L-prolylglycinamide.

As used herein, the term "turosteride" refers to turosteride and pharmaceutically acceptable salts thereof. Turosteride includes FCE-26073. Turosteride includes ((4aR,4bS,6aS,7S,9aS,9bS,11aR)-1,4a,6a-trimethyl-2-oxo-N-(propan-2-yl)-N-(propan-2-ylcarbamoyl)hexadecahydro-1H-indeno[5,4-f]quinoline-7-carboxamide), and 1-(4-methyl-3-oxo-4-aza-5-alpha-androstane-17-beta-carbonyl)-1,3-diisopropylurea.

As used herein, the term "vinclozolin" refers to vinclozolin and pharmaceutically acceptable salts thereof. Vinclozolin includes Ronilan, Curalan, Vorlan, and Touche. Vinclozolin includes ((RS)-3-(3,5-dichlorophenyl)-5-methyl-5-vinyloxazolidine-2,4-dione).

The term "VT-464", as used herein, refers to VT-464 and pharmaceutically acceptable salts thereof, including VT-464 racemate and VT-464 R enantiomer. VT-464 refers to the non-steroidal selective CYP17A1 inhibitor developed by Viamet Pharmaceuticals.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. The section below describes some of the compounds that can be used to treat cancer, or inhibit or delay the growth of cancer cells, especially prostate cancer cells alone or in combination with one or more androgen deprivation therapies (e.g., castration, hormonal castration, hormonal ablation, or hormone therapy).

II. Compounds of Formulae (I), (II), (III), and (IV)

Some alternatives disclosed herein relate to a compound of Formula (I), a pharmaceutically acceptable salt thereof, and methods of using these compounds with and without a hormone therapy agent, as described herein, to inhibit, delay, treat, or prevent prostate cancer cell growth or prostate cancer in a subject in need thereof. Formula (I):

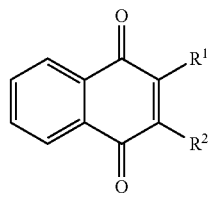

(I)

wherein: $R^1$ can be —O—$R^3$ or —$NR^4R^5$;

$R^2$ can be selected from hydrogen, halogen, and —O—$R^3$;

$R^3$ is an optionally substituted aryl, wherein the aryl is optionally substituted with one to five groups independently selected from —OH, —COOH, —$NR^6R^7$, halogen, nitro, cyano, $C_{1-6}$ alkyl, $C_{1-6}$ alkoxy, $C_{1-6}$ haloalkoxy, $C_6$-$C_{14}$ aryloxy, $C_6$-$C_{14}$ aralkyloxy, $C_6$-$C_{14}$ aralkyl, —(C=O)—$C_{1-6}$ alkyl, —(C=O)—O—$C_{1-6}$ alkyl, —N—(C=O)—$C_{1-6}$ alkyl, $C_{1-6}$ alkyl-N($R^6$)($R^7$), —O(C=O)—NH—$C_{1-6}$ alkyl, and —O(C=O)—NH—$C_{1-6}$ haloalkyl;

$R^4$ and $R^5$ can be independently selected from hydrogen, —(C=O)—$C_{1-6}$ alkyl, and an optionally substituted aryl, wherein the aryl is optionally substituted with one to five groups independently selected from halogen, $C_{1-6}$ alkyl, $C_{1-6}$ haloalkyl, $C_{1-6}$ alkoxy, $C_{1-6}$ haloalkoxy, $C_6$-$C_{14}$ aryloxy, $C_6$-$C_{14}$ aralkyloxy, $C_6$-$C_{14}$ aralkyl, —(C=O)—$C_{1-6}$ alkyl, —$SO_2N$—C(=O)—$C_{1-6}$ alkyl, and —$SO_2NH_2$;

$R^6$ and $R^7$ can be independently selected from hydrogen and an optionally substituted $C_{1-6}$ alkyl.

In some alternatives, $R^1$ can be —O—$R^3$. In some alternatives, $R^1$ can be —$NR^4R^5$. In some alternatives, $R^2$ can be hydrogen. In some alternatives, $R^2$ can be halogen. In some alternatives, $R^2$ can be chloro. In some alternatives, $R^2$ can be bromo. In some alternatives, $R^2$ can be fluoro. In some alternatives, $R^2$ can be iodo. In some alternatives, $R^2$ can be —O—$R^3$.

In some alternatives, $R^3$ can be an unsubstituted aryl. In some alternatives, $R^3$ can be a substituted aryl, wherein the aryl is substituted with one to five groups. In some alternatives, $R^3$ can be a substituted aryl, wherein the aryl is substituted with one group. In some alternatives, $R^3$ can be a substituted aryl, wherein the aryl is substituted with two groups. In some alternatives, $R^3$ can be a substituted aryl, wherein the aryl is substituted with three groups. In some alternatives, $R^3$ can be a substituted aryl, wherein the aryl is substituted with four groups. In some alternatives, $R^3$ can be a substituted aryl, wherein the aryl is substituted with five groups. In some alternatives, $R^3$ can be a substituted or unsubstituted phenyl group. In some alternatives, $R^3$ can be a substituted or unsubstituted naphthyl group.

In some alternatives, when $R^3$ is a substituted aryl, the aryl group can be substituted with one to five —OH substituents. In some alternatives, $R^3$ is a substituted aryl, wherein the aryl group can be substituted with one to five —COOH substituents. In some alternatives, $R^3$ is a substituted aryl, wherein the aryl group is optionally substituted with one to five substituents independently selected from —$NR^6R^7$. In some alternatives, $R^3$ is a substituted aryl, wherein the aryl group is optionally substituted with one to five substituents independently selected from halogen. In some alternatives, $R^3$ is a substituted aryl, wherein the aryl group is optionally substituted with one to five substituents independently selected from nitro or cyano. In some alternatives, $R^3$ is a substituted aryl, wherein the aryl group is optionally substituted with one to five substituents independently selected from $C_{1-6}$ alkyl. In some alternatives, $R^3$ is a substituted aryl, wherein the aryl group is optionally substituted with one to five substituents independently selected from $C_{1-6}$ alkoxy. In some alternatives, $R^3$ is a substituted aryl, wherein the aryl group is optionally substituted with one to five substituents independently selected from $C_{1-6}$ haloalkoxy. In some alternatives, $R^3$ is a substituted aryl, wherein the aryl group is optionally substituted with one to five substituents independently selected from $C_6$-$C_{14}$ aryloxy. In some alternatives, $R^3$ is a substituted aryl, wherein the aryl group is optionally substituted with one to five substituents independently selected from $C_6$-$C_{14}$ aralkyloxy.

In some alternatives, when $R^3$ is a substituted aryl, the aryl group is optionally substituted with one to five substituents independently selected from $C_6$-$C_{14}$ aralkyl. In some alternatives, $R^3$ is a substituted aryl, wherein the aryl group is optionally substituted with one to five substituents independently selected from —(C=O)—$C_{1-6}$ alkyl. In some alternatives, $R^3$ is a substituted aryl, wherein the aryl group is optionally substituted with one to five substituents independently selected from —(C=O)—O—$C_{1-6}$ alkyl. In some alternatives, $R^3$ is a substituted aryl, wherein the aryl group is optionally substituted with one to five substituents independently selected from —N—(C=O)—$C_{1-6}$ alkyl. In some alternatives, $R^3$ is a substituted aryl, wherein the aryl group is optionally substituted with one to five substituents independently selected from —$C_{1-6}$ alkyl-N($R^6$)($R^7$). In some alternatives, $R^3$ is a substituted aryl, wherein the aryl group is optionally substituted with one to five substituents independently selected from —O(C=O)—NH—$C_{1-6}$ alkyl. In some alternatives, $R^3$ is a substituted aryl, wherein the aryl group is optionally substituted with one to five substituents independently selected from —O(C=O)—NH—$C_{1-6}$ haloalkyl.

In some alternatives, $R^4$ and $R^5$ can be the same. In some alternatives, $R^4$ and $R^5$ can be different. In some alternatives, $R^4$ can be hydrogen. In some alternatives, $R^4$ can be an unsubstituted aryl. In some alternatives, $R^4$ can be —(C=O)—$C_{1-6}$ alkyl. In some alternatives, $R^4$ can be a substituted aryl, wherein the aryl is substituted with one to five groups. In some alternatives, $R^4$ can be a substituted aryl, wherein the aryl is substituted with one group. In some alternatives, $R^4$ can be a substituted aryl, wherein the aryl is substituted with two groups. In some alternatives, $R^4$ can be a substituted aryl, wherein the aryl is substituted with three groups. In some alternatives, $R^4$ can be a substituted aryl, wherein the aryl is substituted with four groups. In some alternatives, $R^4$ can be a substituted aryl, wherein the aryl is substituted with five groups. In some alternatives, the aryl group for $R^4$ can be a phenyl group.

In some alternatives, when $R^4$ is a substituted aryl, the aryl group is substituted with one to five substituents independently selected from flouro, chloro, bromo and iodo. In some alternatives, when $R^4$ is a substituted aryl, the aryl group is substituted with one to five substituents independently selected from $C_{1-6}$ alkyl. In some alternatives, when $R^4$ is a substituted aryl, the aryl group is substituted with one to five substituents independently selected from $C_{1-6}$ haloalkyl. In some alternatives, $R^4$ is a substituted aryl, wherein the aryl group is substituted with one to five substituents independently selected from $C_{1-6}$ alkoxy. In some alternatives, $R^4$ is a substituted aryl, wherein the aryl group is substituted with one to five substituents independently selected from $C_{1-6}$ haloalkoxy. In some alternatives, $R^4$ is a substituted aryl, wherein the aryl group is substituted with one to five substituents independently selected from $C_6$-$C_{14}$ aryloxy. In some alternatives, $R^4$ is a substituted aryl, wherein the aryl group is substituted with one to five substituents independently selected from $C_6$-$C_{14}$ aralkyloxy. In some alternatives, $R^4$ is a substituted aryl, wherein the aryl group is substituted with one to five substituents independently selected from $C_6$-$C_{14}$ aralkyl. In some alternatives, $R^4$ is a substituted aryl, wherein the aryl group is substituted with one to five substituents independently selected from —(C=O)—$C_{1-6}$ alkyl. In some alternatives, $R^4$ is a substituted aryl, wherein the aryl group is substituted with one to five substituents independently selected from —$SO_2$N—C(=O)—$C_{1-6}$ alkyl. In some alternatives, $R^4$ is a substituted aryl, wherein the aryl group is substituted with one to five substituents independently selected from —$SO_2NH_2$.

In some alternatives, $R^5$ can be hydrogen. In some alternatives, $R^5$ can be —(C=O)—$C_{1-6}$ alkyl. In some alternatives, $R^5$ can be an unsubstituted aryl. In some alternatives, $R^5$ can be a substituted aryl, wherein the aryl is substituted with one to five groups. In some alternatives, $R^5$ can be a substituted aryl, wherein the aryl is substituted with one group. In some alternatives, $R^5$ can be a substituted aryl, wherein the aryl is substituted with two groups. In some alternatives, $R^5$ can be a substituted aryl, wherein the aryl is substituted with three groups. In some alternatives, $R^5$ can be a substituted aryl, wherein the aryl is substituted with four groups. In some alternatives, $R^5$ can be a substituted aryl, wherein the aryl is substituted with five groups. In some alternatives, the aryl group for $R^5$ can be a phenyl group.

In some alternatives, when $R^5$ is a substituted aryl, the aryl group is substituted with one to five substituents independently selected from flouro, chloro, bromo and iodo. In some alternatives, when $R^5$ is a substituted aryl, the aryl group is optionally substituted with one to five substituents independently selected from $C_{1-6}$ alkyl. In some alternatives, when $R^5$ is a substituted aryl, the aryl group is substituted with one to five substituents independently selected from $C_{1-6}$ haloalkyl. In some alternatives, $R^5$ is a substituted aryl, wherein the aryl group is substituted with one to five substituents independently selected from $C_{1-6}$ alkoxy. In some alternatives, $R^5$ is a substituted aryl, wherein the aryl group is substituted with one to five substituents independently selected from $C_{1-6}$ haloalkoxy. In some alternatives, $R^5$ is a substituted aryl, wherein the aryl group is substituted with one to five substituents independently selected from $C_6$-$C_{14}$ aryloxy. In some alternatives, $R^5$ is a substituted aryl, wherein the aryl group is substituted with one to five substituents independently selected from $C_6$-$C_{14}$ aralkyloxy. In some alternatives, $R^5$ is a substituted aryl, wherein the aryl group is substituted with one to five substituents independently selected from $C_6$-$C_{14}$ aralkyl. In some alternatives, $R^5$ is a substituted aryl, wherein the aryl group is substituted with one to five substituents independently selected from —(C=O)—$C_{1-6}$ alkyl. In some alternatives, $R^5$ is a substituted aryl, wherein the aryl group is substituted with one to five substituents independently selected from —$SO_2$N—C(=O)—$C_{1-6}$ alkyl. In some alternatives, $R^5$ is a substituted aryl, wherein the aryl group is substituted with one to five substituents independently selected from —$SO_2NH_2$.

In some alternatives, $R^6$ and $R^7$ can be the same. In some alternatives, $R^6$ and $R^7$ can be different. In some alternatives, $R^6$ can be hydrogen. In some alternatives, $R^6$ can be an unsubstituted $C_{1-6}$ alkyl. In some alternatives, $R^6$ can be a substituted $C_{1-6}$ alkyl. In some alternatives, $R^7$ can be hydrogen. In some alternatives, $R^7$ can be an unsubstituted $C_{1-6}$ alkyl. In some alternatives, $R^7$ can be a substituted $C_{1-6}$ alkyl. Examples of optionally substituted $C_{1-6}$-alkyls include optionally substituted variants of the following: methyl, ethyl, n-propyl, isopropyl, n-butyl, isobutyl, tert-butyl, pentyl (branched and straight-chained), and hexyl (branched and straight-chained).

In some alternatives $R^1$ can be —O—$R^3$, $R^2$ can be hydrogen, and $R^3$ can be an unsubstituted aryl. In some alternatives, $R^1$ can be —O-phenyl and $R^2$ can be hydrogen. In some alternatives, $R^1$ can be —O-naphthyl and $R^2$ can be hydrogen.

In some alternatives $R^1$ can be —O—$R^3$, $R^2$ can be hydrogen, and $R^3$ can be a substituted aryl. In some alternatives $R^1$ can be —O—$R^3$, $R^2$ can be hydrogen, and $R^3$ can be phenyl substituted with one to five halogens. In some alternatives $R^1$ can be —O—$R^3$, $R^2$ can be hydrogen, and $R^3$ can be 2,4,6-trifluorophenyl. In some alternatives $R^1$ can be —O—$R^3$, $R^2$ can be hydrogen, and $R^3$ can be 2,3,4,5,6-pentafluorophenyl. In some alternatives $R^1$ can be —O—$R^3$, $R^2$ can be hydrogen, and $R^3$ can be 4-chlorophenyl. In some alternatives $R^1$ can be —O—$R^3$, $R^2$ can be hydrogen, and $R^3$ can be 3,5-difluorophenyl.

In some alternatives $R^1$ can be —O—$R^3$, $R^2$ can be hydrogen, and $R^3$ can be phenyl substituted with one to five $C_{1-6}$ alkyl groups. In some alternatives $R^1$ can be —O—$R^3$, $R^2$ can be hydrogen, and $R^3$ can be 3-methylphenyl.

In some alternatives $R^1$ can be —O—$R^3$, $R^2$ can be hydrogen, and $R^3$ can be phenyl substituted with one to five substituents, wherein the substituents are independently selected from halogen and $C_{1-6}$ alkyl. In some alternatives $R^1$ can be —O—$R^3$, $R^2$ can be hydrogen, and $R^3$ can be 4-chloro-2-methylphenyl. In some alternatives $R^1$ can be —O—$R^3$, $R^2$ can be hydrogen, and $R^3$ can be 4-chloro-3-methylphenyl.

In some alternatives $R^1$ can be —O—$R^3$, $R^2$ can be hydrogen, and $R^3$ can be phenyl substituted with one to five —N—(C=O)—$C_{1-6}$ alkyl groups. In some alternatives $R^1$ can be —O—$R^3$, $R^2$ can be hydrogen, and $R^3$ can be 4-acetamidophenyl.

In some alternatives $R^1$ can be —O—$R^3$, $R^2$ can be hydrogen, and $R^3$ can be 4-hydroxyphenyl. In some alternatives $R^1$ can be —O—$R^3$, $R^2$ can be hydrogen, and $R^3$ can be 4-nitrophenyl.

In some alternatives $R^1$ can be —O—$R^3$, $R^2$ can be hydrogen, $R^3$ can be phenyl substituted with one to five —$C_{1-6}$ alkyl-N($R^6$)($R^7$) groups, and $R^6$ and $R^7$ are unsubstituted $C_{1-6}$ alkyl. In some alternatives $R^1$ can be —O—$R^3$, $R^2$ can be hydrogen, and $R^3$ can be 4-(2-dimethylaminoethyl)phenyl.

In some alternatives $R^1$ can be —O—$R^3$, $R^2$ can be hydrogen, and $R^3$ can be phenyl substituted with one to five $C_{1-6}$ alkoxy groups. In some alternatives $R^1$ can be —O—$R^3$, $R^2$ can be hydrogen, and $R^3$ can be 4-methoxyphenyl.

In some alternatives $R^1$ can be —O—$R^3$, $R^2$ can be hydrogen, and $R^3$ can be phenyl substituted with one to five $C_6$-$C_{14}$ aralkyloxy groups. In some alternatives $R^1$ can be —O—$R^3$, $R^2$ can be hydrogen, and $R^3$ can be 4-(benzyloxy)phenyl.

In some alternatives $R^1$ can be —O—$R^3$, $R^2$ can be hydrogen, and $R^3$ can be phenyl substituted with one to five substituents, wherein the substituents are independently selected from halogen and $C_6$-$C_{14}$ aralkyl. In some alternatives $R^1$ can be —O—$R^3$, $R^2$ can be hydrogen, and $R^3$ can be 2-benzyl-4-chlorophenyl.

In some alternatives $R^1$ can be —O—$R^3$, $R^2$ can be hydrogen, and $R^3$ can be phenyl substituted with one to five substituents, wherein the substituents are independently selected from halogen and $C_{1-6}$ alkoxy. In some alternatives $R^1$ can be —O—$R^3$, $R^2$ can be hydrogen, and $R^3$ can be 2-chloro-4-methoxyphenyl.

In some alternatives $R^1$ can be —O—$R^3$, $R^2$ can be halogen, and $R^3$ can be an unsubstituted aryl. In some alternatives $R^1$ can be —O—$R^3$, $R^2$ can be bromo, and $R^3$ can be phenyl.

In some alternatives $R^1$ can be —O—$R^3$, $R^2$ can be halogen, and $R^3$ can be a substituted aryl. In some alternatives $R^1$ can be —O—$R^3$, $R^2$ can be halogen, and $R^3$ can be a phenyl substituted with one to five halogens. In some alternatives $R^1$ can be —O—$R^3$, $R^2$ can be bromo, and $R^3$ can be 2,3,4,5,6-pentafluorophenyl. In some alternatives $R^1$ can be —O—$R^3$, $R^2$ can be halogen, and $R^3$ can be a phenyl substituted with one to five —(C=O)—O—$C_{1-6}$ alkyl groups. In some alternatives $R^1$ can be —O—$R^3$, $R^2$ can be bromo, and $R^3$ can be 2-(methoxycarbonyl)-phenyl.

In some alternatives $R^1$ and $R^2$ can each be —O—$R^3$, and $R^3$ can be an unsubstituted aryl. In some alternatives $R^1$ and $R^2$ can each be —O—$R^3$, and $R^3$ can be an unsubstituted aryl wherein the unsubstituted aryl $R^3$ of $R^1$ is different from the unsubstituted aryl $R^3$ of $R^2$. In some alternatives $R^1$ and $R^2$ can each be —O—$R^3$, and $R^3$ can be an unsubstituted aryl wherein the unsubstituted aryl $R^3$ can be the same for $R^1$ and $R^2$. In some alternatives $R^1$ and $R^2$ can each be —O—$R^3$, and $R^3$ can be phenyl.

In some alternatives $R^1$ and $R^2$ can each be —O—$R^3$, and $R^3$ can be a substituted aryl. In some alternatives $R^1$ and $R^2$ can each be —O—$R^3$, and $R^3$ can be a substituted aryl wherein the substituted aryl $R^3$ of $R^1$ is different from the substituted aryl $R^3$ of $R^2$. In some alternatives $R^1$ and $R^2$ can each be —O—$R^3$, and $R^3$ can be a substituted aryl wherein the substituted aryl $R^3$ can be the same for $R^1$ and $R^2$. In some alternatives $R^1$ and $R^2$ can each be —O—$R^3$, and $R^3$ can be phenyl substituted with one to five halogens. In some alternatives $R^1$ and $R^2$ can each be —O—$R^3$, and $R^3$ can be 2,4,6-trifluorophenyl. In some alternatives, $R^1$ and $R^2$ can each be —O—$R^3$, and $R^3$ can be 4-chlorophenyl. In some alternatives $R^1$ and $R^2$ can each be —O—$R^3$, and $R^3$ can be perfluorophenyl. In some alternatives $R^1$ and $R^2$ can each be —O—$R^3$, and $R^3$ can be 3,5-difluorophenyl.

In some alternatives $R^1$ and $R^2$ can each be —O—$R^3$, and $R^3$ can be phenyl substituted with one to five substituents, wherein the substituents are independently selected from halogen and $C_1$-$C_6$ alkyl. In some alternatives $R^1$ and $R^2$ can each be —O—$R^3$, and $R^3$ can be 4-chloro-2-methylphenyl.

In some alternatives $R^1$ and $R^2$ can each be —O—$R^3$, and $R^3$ can be phenyl substituted with one to five —N—(C=O)—$C_{1-6}$ alkyl groups. In some alternatives $R^1$ and $R^2$ can each be —O—$R^3$, and $R^3$ can be 4-acetamidophenyl.

In some alternatives $R^1$ and $R^2$ can each be —O—$R^3$, and $R^3$ can be 4-hydroxyphenyl. In some alternatives $R^1$ and $R^2$ can each be —O—$R^3$, and $R^3$ can be 4-aminophenyl. In some alternatives $R^1$ and $R^2$ can each be —O—$R^3$, and $R^3$ can be 4-nitrophenyl.

In some alternatives $R^1$ and $R^2$ can each be —O—$R^3$, and $R^3$ can be phenyl substituted with one to five $C_{1-6}$ alkyl groups. In some alternatives $R^1$ and $R^2$ can each be —O—$R^3$, and $R^3$ can be 3-methylphenyl.

In some alternatives $R^1$ and $R^2$ can each be —O—$R^3$, and $R^3$ can be phenyl substituted with one to five $C_{1-6}$ alkoxy groups. In some alternatives $R^1$ and $R^2$ can each be —O—$R^3$, and $R^3$ can be 4-methoxyphenyl. In some alternatives, $R^1$ and $R^2$ can each be —O—$R^3$, and $R^3$ can be phenyl substituted with one to five $C_6$-$C_{14}$ aralkyloxy groups. In some alternatives $R^1$ and $R^2$ can each be —O—$R^3$, and $R^3$ can be 4-(benzyloxy)phenyl.

In some alternatives $R^1$ and $R^2$ can each be —O—$R^3$, and $R^3$ can be phenyl substituted with one to five —O(C=O)—NH—$C_{1-6}$ haloalkyl groups. In some alternatives $R^1$ and $R^2$ can each be —O—$R^3$, and $R^3$ can be 4-((2-chloroethyl)carbamoyloxy)phenyl.

In some alternatives $R^1$ can be —N$R^4R^5$, $R^2$ can be hydrogen, $R^4$ can be hydrogen, and $R^5$ can be an unsubstituted aryl. In some alternatives $R^1$ can be —N$R^4R^5$, $R^2$ can be hydrogen, $R^4$ can be hydrogen, and $R^5$ can be phenyl.

In some alternatives $R^1$ can be —N$R^4R^5$, $R^2$ can be hydrogen, $R^4$ can be hydrogen, and $R^5$ can be a substituted aryl. In some alternatives $R^1$ can be —N$R^4R^5$, $R^2$ can be hydrogen, $R^4$ can be hydrogen, and $R^5$ can be phenyl substituted with one to five halogens. In some alternatives $R^1$ can be —N$R^4R^5$, $R^2$ can be hydrogen, $R^4$ can be hydrogen, and $R^5$ can be 3,5-difluorophenyl. In some alternatives $R^1$ can be —N$R^4R^5$, $R^2$ can be hydrogen, $R^4$ can be hydrogen, and $R^5$ can be 4-chlorophenyl. In some alternatives $R^1$ can be —N$R^4R^5$, $R^2$ can be hydrogen, $R^4$ can be hydrogen, and $R^5$ can be phenyl substituted with one to five $C_{1-6}$ alkyl groups. In some alternatives $R^1$ can be —N$R^4R^5$, $R^2$ can be hydrogen, $R^4$ can be hydrogen, and $R^5$ can be p-tolyl. In some alternatives $R^1$ can be —N$R^4R^5$, $R^2$ can be hydrogen, $R^4$ can be hydrogen, and $R^5$ can be phenyl substituted with one to five $C_{1-6}$ haloalkyl groups. In some alternatives $R^1$ can be —N$R^4R^5$, $R^2$ can be hydrogen, $R^4$ can be hydrogen, and $R^5$ can be 4-(trifluoromethyl)phenyl. In some alternatives $R^1$ can be —N$R^4R^5$, $R^2$ can be hydrogen, $R^4$ can be hydrogen, and $R^5$ can be phenyl substituted with one to five $C_{1-6}$ haloalkoxy groups. In some alternatives $R^1$ can be —N$R^4R^5$, $R^2$ can be hydrogen, $R^4$ can be hydrogen, and $R^5$ can be 4-(trifluoromethoxy)phenyl. In some alternatives $R^1$ can be —N$R^4R^5$, $R^2$ can be hydrogen, $R^4$ can be hydrogen, and $R^5$ can be phenyl substituted with one to five —SO$_2$N—C(=O)—$C_{1-6}$ alkyl groups. In some alternatives $R^1$ can be —N$R^4R^5$, $R^2$ can be hydrogen, $R^4$ can be hydrogen, and $R^5$ can be phenyl substituted with one to five —SO$_2$N—C(=O)—CH$_3$. In some alternatives $R^1$ can be —N$R^4R^5$, $R^2$ can be hydrogen, $R^4$ can be hydrogen, and $R^5$ can be phenyl substituted with one to five —SO$_2$NH$_2$.

In some alternatives $R^1$ can be —N$R^4R^5$, $R^2$ can be hydrogen, $R^4$ can be hydrogen, and $R^5$ can be a $C_{1-6}$ haloalkoxy. In some alternatives $R^1$ can be —N$R^4R^5$, $R^2$ can be hydrogen, $R^4$ can be hydrogen, and $R^5$ can be 4-trifluoromethoxyphenyl.

In some alternatives $R^1$ can be —N$R^4R^5$, $R^2$ can be halogen, $R^4$ can be hydrogen, and $R^5$ can be —(C=O)—$C_{1-6}$ alkyl. In some alternatives $R^1$ can be —N$R^4R^5$, $R^2$ can be chloro, $R^4$ can be hydrogen, and $R^5$ can be acetyl.

In some alternatives R¹ can be —NR⁴R⁵, R² can be halogen, R⁴ can be —(C=O)—C₁₋₆ alkyl, and R⁵ can be —(C=O)—C₁₋₆ alkyl. In some alternatives R¹ can be —NR⁴R⁵, R² can be chloro, R⁴ can be acetyl, and R⁵ can be acetyl.

In some alternatives R¹ can be —NR⁴R⁵, R² can be —O—R³, R³ can be an unsubstituted aryl, R⁴ can be hydrogen, and R⁵ can be —(C=O)—C₁₋₆ alkyl. In some alternatives R¹ can be —NR⁴R⁵, R² can be —O—R³, R³ can be phenyl, R⁴ can be hydrogen, and R⁵ can be acetyl.

In some alternatives R¹ can be —NR⁴R⁵, R² can be —O—R³, R³ can be a substituted aryl, R⁴ can be hydrogen, and R⁵ can be —(C=O)—C₁₋₆ alkyl. In some alternatives R¹ can be —NR⁴R⁵, R² can be —O—R³, R³ can be phenyl substituted with one to five halogens, R⁴ can be hydrogen, and R⁵ can be —(C=O)—C₁₋₆ alkyl. In some alternatives R¹ can be —NR⁴R⁵, R² can be —O—R³, R³ can be 4-chlorophenyl, R⁴ can be hydrogen, and R⁵ can be acetyl. In some alternatives R¹ can be —NR⁴R⁵, R² can be —O—R³, R³ can be 3,5-difluorophenyl, R⁴ can be hydrogen, and R⁵ can be acetyl.

In some alternatives R¹ can be —NR⁴R⁵, R² can be —O—R³, R³ can be phenyl substituted with one to five —N—(C=O)—C₁₋₆ alkyl groups, R⁴ can be hydrogen, and R⁵ can be —(C=O)—C₁₋₆ alkyl. In some alternatives R¹ can be —NR⁴R⁵, R² can be —O—R³, R³ can be 4-acetamidophenyl, R⁴ can be hydrogen, and R⁵ can be acetyl.

In some alternatives R¹ can be —NR⁴R⁵, R² can be —O—R³, R³ can be phenyl substituted with one to five C₁₋₆ alkoxy groups, R⁴ can be hydrogen, and R⁵ can be —(C=O)—C₁₋₆ alkyl. In some alternatives R¹ can be —NR⁴R⁵, R² can be —O—R³, R³ can be 4-methoxyphenyl, R⁴ can be hydrogen, and R⁵ can be acetyl.

In some alternatives R¹ can be —NR⁴R⁵, R² can be —O—R³, R³ can be phenyl substituted with one to five C₆-C₁₄ aralkyloxy groups, R⁴ can be hydrogen, and R⁵ can be —(C=O)—C₁₋₆ alkyl. In some alternatives R¹ can be —NR⁴R⁵, R² can be —O—R³, R³ can be 4-(benzyloxy)phenyl, R⁴ can be hydrogen, and R⁵ can be acetyl.

Examples of compound of Formula (I) include, but ere not limited to the following:

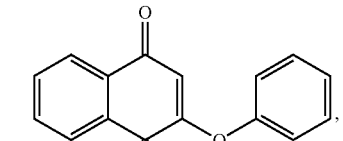

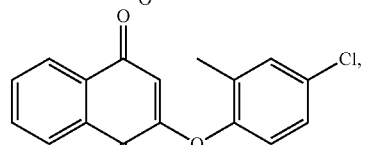

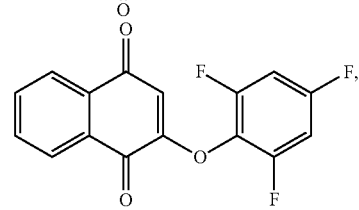

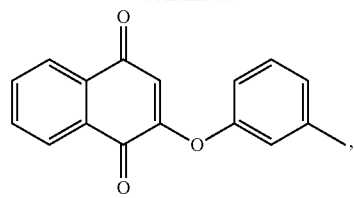

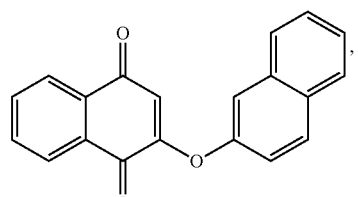

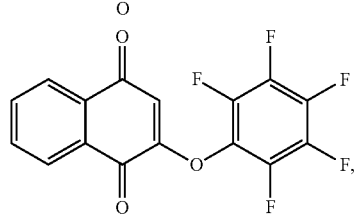

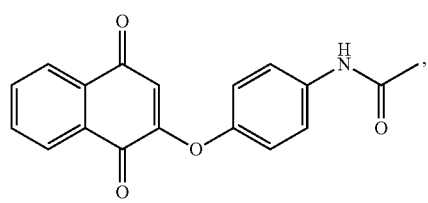

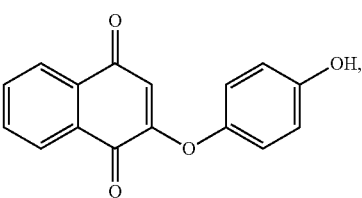

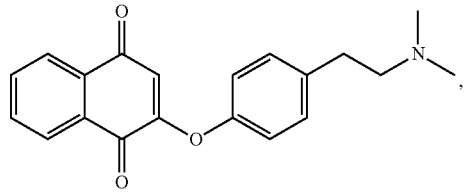

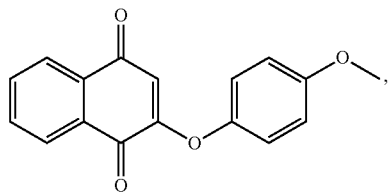

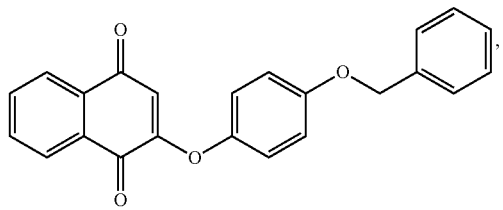

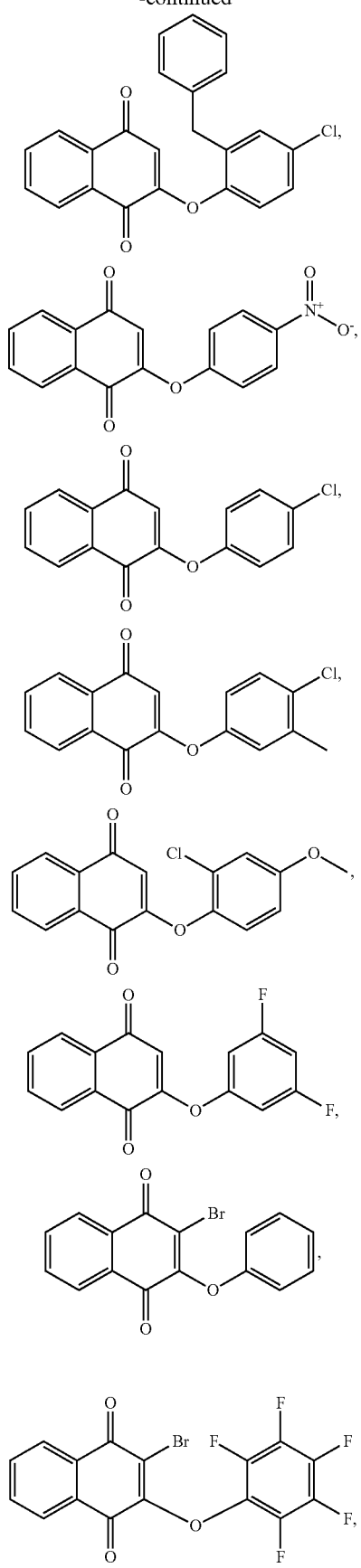
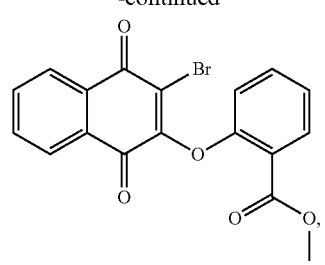
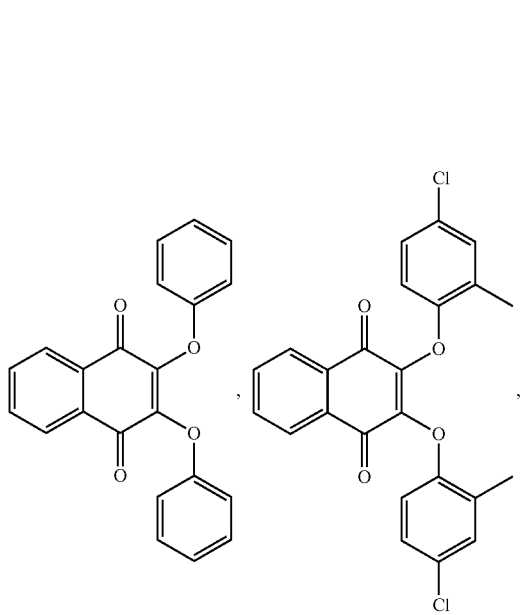
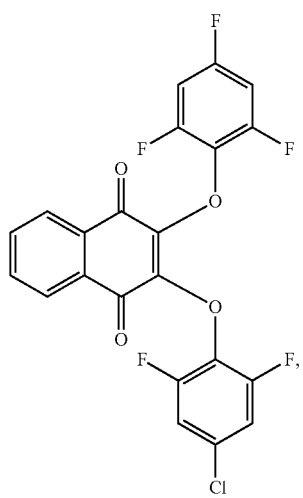

-continued
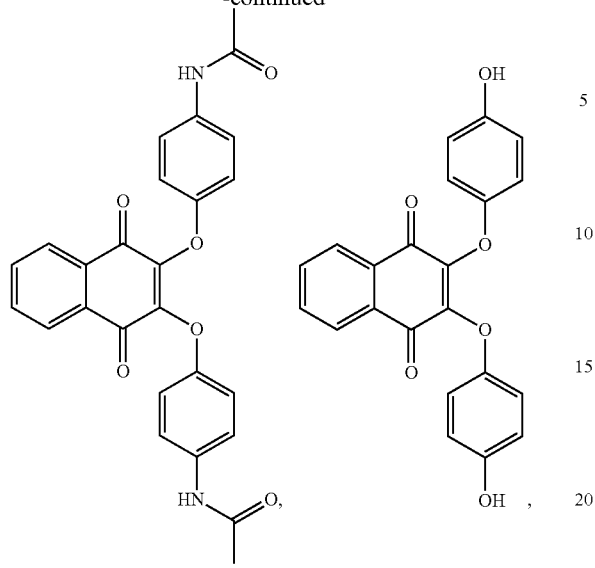
-continued
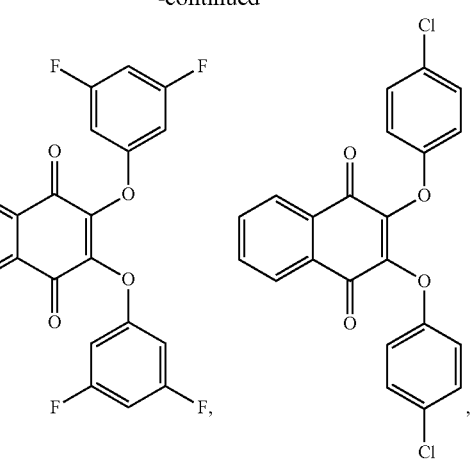
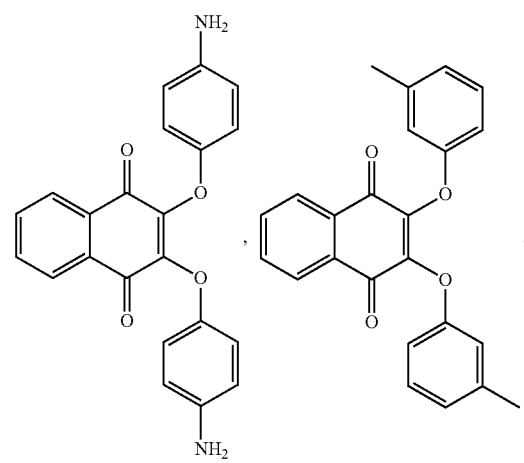
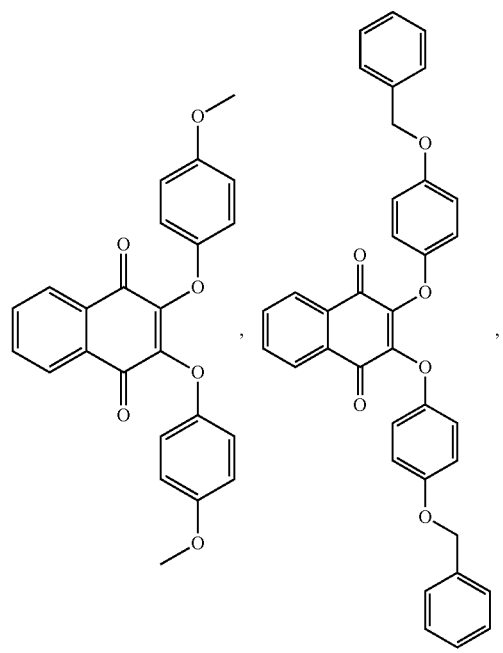

-continued
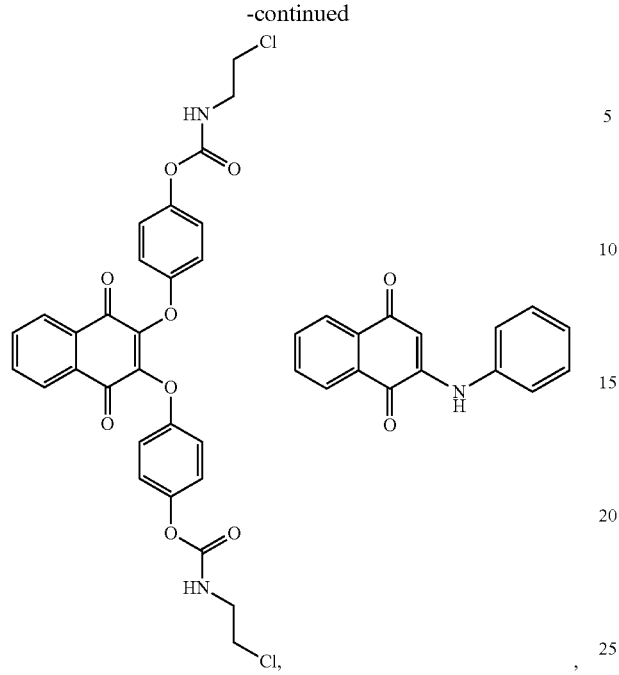
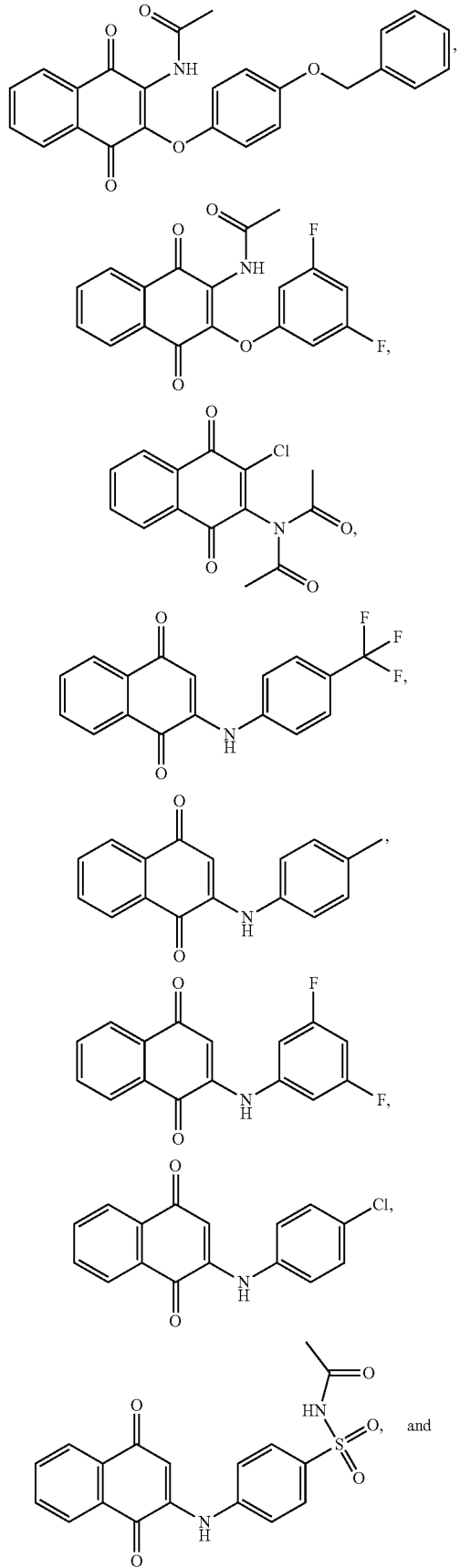

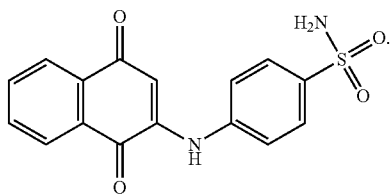

Some alternatives disclosed herein relate to a compound of Formula (II), a pharmaceutically acceptable salt thereof, and methods of using these compounds with and without a hormone therapy agent, as described herein, to inhibit, delay, ameliorate, treat, or prevent prostate cancer cell growth or prostate cancer in a subject in need thereof. Formula (II):

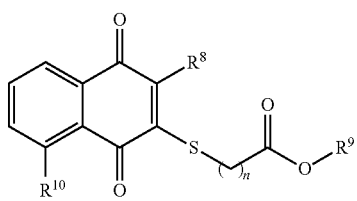

(II)

wherein: $R^8$ can be hydrogen or $C_{1-6}$ alkyl;

$R^9$ can be hydrogen or $C_{1-6}$ alkyl;

$R^{10}$ can be selected from hydrogen, —OH, and —COOH; and n is an integer selected from 1 to 6.

In some alternatives, $R^8$ can be hydrogen. In some alternatives, $R^8$ can be $C_{1-6}$ alkyl. In some alternatives, $R^9$ can be hydrogen. In some alternatives, $R^9$ can be $C_{1-6}$ alkyl. In some alternatives, $R^{10}$ can be hydrogen. In some alternatives, $R^{10}$ can be —OH. In some alternatives, $R^{10}$ can be —COOH.

In some alternatives $R^8$ can be $C_{1-6}$ alkyl, $R^9$ can be $C_{1-6}$ alkyl, $R^{10}$ can be —OH, and n=1. In some alternatives $R^8$ can be methyl, $R^9$ can be methyl, $R^{10}$ can be —OH, and n=1.

Examples of compound of Formula (II) include, but are not limited to the following:

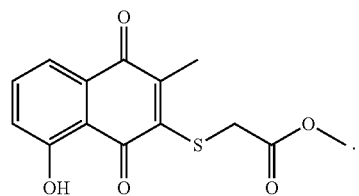 [SMILES: COC(=O)CSC1=C(C)C(=O)c2cccc(O)c2C1=O]

Some alternatives disclosed herein relate to a compound of Formula (III), a pharmaceutically acceptable salt thereof, and methods of using these compounds with and without a hormone therapy agent, as described herein, to inhibit, delay, treat, or prevent prostate cancer cell growth or prostate cancer in a subject in need thereof. Formula (III):

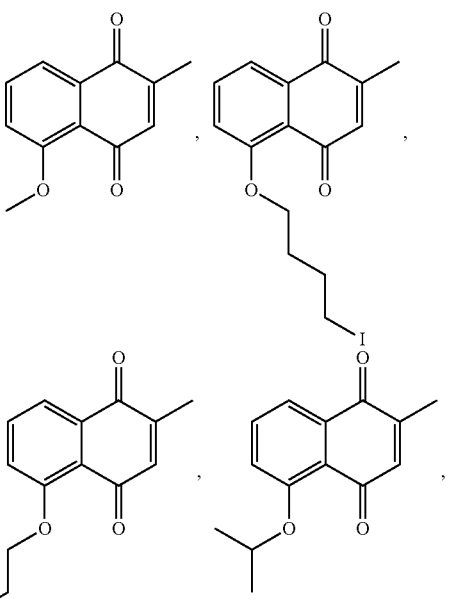

(III)

wherein: $R^{11}$ can be selected from $C_{1-6}$ alkyl, $C_{1-6}$ haloalkyl, —(C=O)—$C_{1-6}$ alkyl, and —(C=O)—$C_{1-6}$ haloalkyl.

In some alternatives, $R^{11}$ can be $C_{1-6}$ alkyl. In some alternatives, $R^{11}$ can be methyl. In some alternatives, $R^{11}$ can be isopropyl. In some alternatives, $R^{11}$ can be $C_{1-6}$ haloalkyl. In some alternatives, $R^{11}$ can be 4-iodobutyl. In some alternatives, $R^{11}$ can be 4-iodopropyl. In some alternatives, $R^{11}$ can be —(C=O)—$C_{1-6}$ alkyl. In some alternatives, $R^{11}$ can be —(C=O)-methyl. In some alternatives, $R^{11}$ can be —(C=O)—$C_{1-6}$ haloalkyl. In some alternatives, $R^{11}$ can be —(C=O)-iodomethyl.

Examples of compound of Formula (III) include, but are not limited to the following:

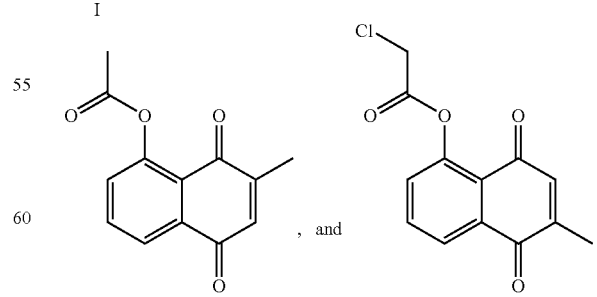

, and

Some alternatives disclosed herein relate to a compound of Formula (IV), a pharmaceutically acceptable salt thereof, and methods of using these compounds with and without a hormone therapy agent, as described herein, to inhibit, delay, treat, or prevent prostate-cancer cell growth or prostate cancer in a subject in need thereof. Formula (IV):

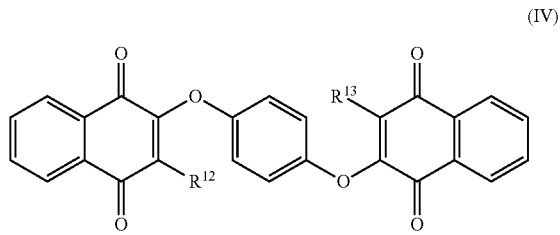

(IV)

wherein: $R^{12}$ and $R^{13}$ can be independently selected from hydrogen, halogen, $C_{1-6}$ alkyl, and —NH—(C=O)—($C_{1-6}$ alkyl).

In some alternatives, $R^{12}$ and $R^{13}$ can be the same. In some alternatives, $R^{12}$ and $R^{13}$ can be different. In some alternatives, $R^{12}$ and $R^{13}$ can each be hydrogen. In some alternatives, $R^{12}$ and $R^{13}$ can each be halogen. In some alternatives, $R^{12}$ can be bromo and $R^{13}$ can be bromo. In some alternatives, $R^{12}$ and $R^{13}$ can each be $C_{1-6}$ alkyl. In some alternatives, $R^{12}$ and $R^{13}$ can each be —NH—(C=O)—($C_{1-6}$ alkyl). In some alternatives, $R^{12}$ can be —NH—(C=O)-methyl and $R^{13}$ can be —NH—(C=O)-methyl.

Examples of compound of Formula (IV) include, but are not limited to the following:

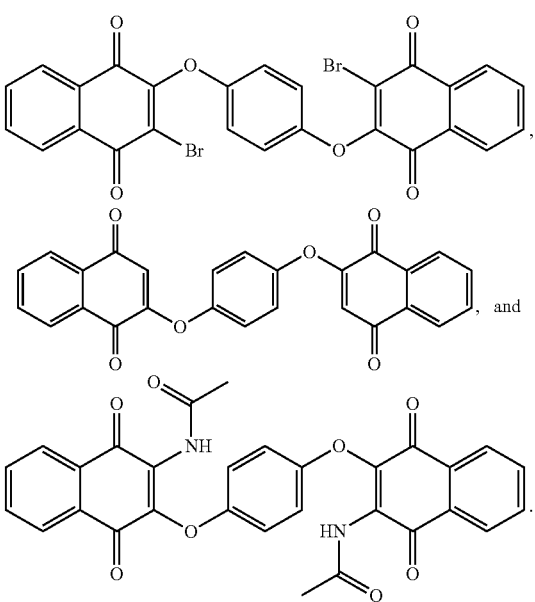

The section below describes some of the conventional therapies that can be used to inhibit, ameliorate, or delay prostate cancer cell growth and/or treat, ameliorate or prevent prostate cancer. It should be understood that the inventive therapies described herein can be performed with and without any of the conventional therapies for prostate cancer including any one or more of the therapies described in the following section.

III. Prostate Cancer

There were an estimated 192,280 new cases of prostate cancer diagnosed in the U.S. in 2009 and an estimated 27,360 deaths. About 90% of patients with advanced disease will develop bone metastases, associated with severe pain, loss of mobility, and spinal cord compression. Other affected organs may include the liver, lungs and brain. Advanced prostate cancer is resistant to hormone therapy, radiation and conventional chemotherapy. Although the 5-year survival rate is close to 100% for local disease, it drops to 30% for advanced cancer.

In the initial stages, prostate tumor growth is androgen dependent. Androgens are used by prostate cancer cells for both proliferation as well as regulation, and are vital for maintaining the growth and survival of the cancer cell. The main androgen that circulates is testosterone, which is mainly produced in the testes. Extragonadal sources of androgen synthesis do, however, exist and may play a role in the development of castration-resistant forms of prostate cancer. Generally, androgen dependent prostate cancer therapy focuses on minimizing testicular synthesis of androgens with luteinizing hormone releasing hormone ("LHRH") agonists or antagonists. Some therapies also focus on modulating the androgen receptor itself, or its downstream signaling pathway.

Androgen dependent prostate cancer will eventually progress into castration-resistant prostate cancer ("CRPC"). Although these patients are "androgen insensitive," researchers have discovered that androgen-responsive genes are still expressed, implying that the androgen-receptor signaling pathway may still be an important target in CRPC patients. Schweizer et al., *Therapeutic Advances in Urology*, 4(4), 167-178.

There have been some advances in the treatment of prostate cancer recently, including new surgical approaches and improvements in radiotherapy. For example:

1) In 1986, surgeons developed a technique (using da Vinci Prostatectomy) that allowed the removal of the prostate while minimizing nerve damage, thereby decreasing adverse side effects.

2) In addition, clinical researchers improved a long-established radiotherapy technique known as brachytherapy, which involves the implantation of a small amount of radioactive material (seeds) into the prostate. This radiation therapy method is an effective treatment for early-stage prostate cancer.

3) There have also been advances in hormonal therapy for prostate cancer including the development of gonadotropin-releasing hormone (GnRH) agonists, which inhibit the ability of the pituitary gland to stimulate the testes to make testosterone.

4) Advances have also been made in chemotherapy for prostate cancer. In 2004, results from two large NCI-sponsored clinical trials showed that use of the drug docetaxel could prolong the survival of men who had advanced prostate cancer that no longer responded to hormonal therapy.

Unfortunately, should the prostate-specific antigen (PSA) level remain above zero after radical prostatectomy is performed, with conventional therapy or with advanced therapy using da Vinci Prostatectomy, this indicates that the prostate cancer has spread outside the capsule, i.e., disseminated disease, and to date, there is no curable treatment for this.

Thus, all current hormonal, as well as, chemotherapy treatment regimens for such disseminated androgen dependent prostate cancers are palliative. Subsequently, even if there have been advances in the treatment of prostate cancer, finding new strategies for treatment of disseminated disease remains a crucial challenge. The section below provides more details on the use of compounds of Formulae (I), (II), (III), and (IV) to inhibit, ameliorate, or delay the growth of cancer cells, in particular prostate cancer cells.

IV. Compounds of Formulae (I), (II), (III), and (IV) as Anticancer Agents

The compounds disclosed herein, such as compounds of Formulae (I), (II), (III), and (IV), have significant and unexpected anti-cancer properties. Without wishing to be bound by theory, it is contemplated that the primary mechanism of cytotoxic action of compounds of Formulae (I), (II), (III), and (IV) is due to redox-cycling and electrophilic arylation. Such compounds can be reduced by electron transfer from flavoprotein to a semiquinone radical, which can, in turn; reduce oxygen to superoxide. The resulting superoxide can consequently be converted into hydrogen peroxide, hydroxyl radicals, and/or peroxynitrite, all of which are highly reactive oxygen species (ROS) with potent cytotoxic and tumoricidal effects.

While still not wishing to be bound by theory, an additional antitumor mechanism of compounds of Formulae (I), (II), (III), and (IV) can involve direct arylation of intracellular thiols leading to depletion of glutathione (GSH). Depletion of GSH may ultimately result in alkylation of cellular macromolecules and in their inactivation. Moreover, it has been shown that low dose concentrations of a naphthoquinone analog (5 µmol/L) can inhibit expression of multiple molecular targets, including protein kinase Cq (PKCq), phosphatidylinositol 3-kinase (PI3K), AKT, activation of transcription factors activator protein-1 (AP-1), nuclear factor-κB (NF-κB), and signal transducer and activator of transcription 3 (Stat3) in prostate carcinoma cells. Such activities may contribute to the tumoricidal effects of compounds of Formulae (I), (II), (III), and (IV).

Moreover, while still not wishing to be bound by theory, an additional antitumor mechanism of compounds of Formulae (I), (II), (III), and (IV) can involve inhibition of microtubule polymerization and binding to tubulin. Because one of the defining characteristics of cancer cells is a significantly increased rate of cell cycle entry and/or mitosis, cancer cells are more vulnerable to agents that affect microtubule polymerization than normal cells. It has been shown that a naphthoquinone analog recognizes the colchicine binding site of tubulin and also Inhibits in vitro tubulin polymerization. See Acharya et al., *Biochemistry* 2008, 47(3), 7838-45.

Compounds of Formulae (I), (II), (III), and (IV) can result in slower growth of androgen independent prostate cancer, and that the mechanism behind the slower growth may be due to apoptosis of prostate tumor cells. Compounds of Formulae (I), (II), (III), and (IV) can induce cell cycle entry, mitosis, and/or apoptosis of androgen-dependent cancer cells.

It is contemplated that several compounds of Formulae (I), (II), (III), and (IV) have anti-cancer activity and that this anti-cancer activity, especially with respect to prostate cancer, can be significantly and unexpectedly improved (e.g., synergy can be obtained) when the compounds are provided in conjunction with a blockade of testosterone/androgen/ DHT (e.g., castration or a hormone treatment therapy, such as hormonal ablation). For example, it is believed that the administration of a compound of Formula (I), (II), (III), or (IV) to a subject in need thereof will effectively inhibit the growth of prostate cancer cells and thereby reduce the incidence of fatal prostate cancer. The combination of such a compound with an antioxidant, such as ascorbic acid, alpha lipoic acid, n-acetyl cysteine (NAC), lycopene, tocopherol, tocotrienol, or others may also be beneficial. The combination of such a compound and mitomycin C can also be beneficial in treating subjects with advanced solid tumors, advanced lung cancer, and advanced gastrointestinal cancer. By administering a combination of a compound of Formula (I), (II), (III), or (IV) and an antioxidant or plurality of antioxidants, such as vitamin C, to subjects having prostate cancer, it is contemplated that a reduction in tumor cell numbers and PSA (prostate cancer specific antigen) will be obtained.

Alternatively or in addition, it is contemplated that several compounds of Formulae (I), (II), (III), and (IV) have anti-cancer activity and that this anti-cancer activity, especially with respect to prostate cancer, can be significantly improved (e.g., synergy can be obtained) when the compounds are provided in conjunction with certain hormonal therapy agents, described in more detail below. It is believed that compounds of Formulae (I), (II), (III), and (IV) interact with the androgen receptor or heat shock proteins that are in communication with the androgen receptor. Accordingly, it is preferred that compounds of Formulae (I), (II), (III), and (IV) are provided in combination or in co-administration with a testosterone synthesis inhibitor that does not interact with or bind to the androgen receptor (e.g., a testosterone synthesis inhibitor that does not bind to the androgen receptor, such as orteronel or VT-464).

It is contemplated herein that a significantly improved inhibition of prostate cancer cell growth can be obtained when castration, hormonal castration, hormonal ablation, or hormone therapy are provided during the time a patient receives the combination of antioxidant (e.g., ascorbic acid) with a compound of Formula (I), (II), (III), or (IV). Provided herein is an improved method for treating a subject suffering from prostate cancer with a compound of Formula (I), (II), (III), or (IV) and androgen ablation therapy to subjects with PSA values above zero after radical prostatectomy, i.e., when they have androgen-dependent disseminated disease. Today there is no cure for this and patients currently receive only palliative treatment, including hormone therapy alone.

It is contemplated that the compounds of Formulae (I), (II), (III), and (IV) are highly oxidative and induce oxidative stress in cells. Accordingly, such compounds can be used to inhibit or ameliorate prostate cancer cell growth and that a significantly improved inhibition or amelioration of prostate cancer cell growth can be obtained when castration, hormonal castration, hormonal ablation, or hormone therapy are provided before, during, and/or after the time a patient receives such compounds.

It is contemplated that a compound of Formula (I), (II), (III), or (IV) can be used to inhibit or ameliorate prostate cancer cell growth and that a significantly improved inhibition or amelioration of prostate cancer cell growth can be obtained when castration, hormonal castration, hormonal ablation, or hormone therapy are provided before, during, and/or after the time a patient receives the compound.

As mentioned above, although providing a subject that has cancer (e.g., prostate cancer) with one or more compounds of Formulae (I), (II), (III), and (IV) alone or in a combination of compounds of Formulae (I), (II), (III), and (IV) can inhibit the growth of cancerous cells, a significantly improved inhibition of cancer cell growth (e.g., prostate cancer cell growth) can be obtained by providing one or more of the compounds of Formulae (I), (II), (III), and (IV), separately or in a mixture, co-administration, or combination, in conjunction with a therapy that reduces the androgen levels of the patient and/or disrupts androgen receptor signaling (e.g., castration, hormonal castration, hormonal ablation, or hormone therapy). That is, some alternatives include methods of inhibiting cancer cell growth (e.g., prostate cancer cell growth or progression of prostate cancer disease) or treating or preventing a cancer (e.g., prostate cancer), wherein a subject having a cancer (e.g., prostate cancer) is provided one or more compounds of Formulae (I), (II), (III), and (IV) (e.g., 2-(phenylamino)naphthalene-1,4-dione) while reducing the amount of androgens in the subject (e.g., providing castration, hormonal castration, hormonal ablation, or hormone therapy). Optionally, the inhibition of cancer (e.g., prostate cancer) or a marker thereof (e.g., PSA) is evaluated during or after the treatment (e.g., after the combination of a compound of Formula (I), (II), (III), or (IV) and hormone therapy is provided). Stated differently, some alternatives include a combination of one or more of the compounds of Formulae (I), (II), (III), and (IV), formulated for administration separately or together, and an androgen deprivation therapy (e.g., castration, hormonal castration, hormonal ablation, or hormone therapy) for use in inhibiting, ameliorating or delaying the growth of prostate cancer cells or treating or preventing prostate cancer. The section below describes some of the approaches that can be used to deplete the levels of androgen in the subject so as to provide the treatments and treatment protocols described above.

V. Hormone Therapy

Hormone therapy for treating prostate cancer, or inhibiting or delaying prostate cancer cell growth, can also be called androgen deprivation therapy (ADT), chemical castration, or androgen ablation therapy. Androgens can fuel the growth of prostatic cells, including both healthy prostatic cells and cancerous prostatic cells. In some alternatives, a subject suffering from prostate cancer is provided with a hormone therapy agent that reduces the subject's androgen levels.

Without wishing to be bound by theory, FIG. 1 illustrates the steroid/androgen synthesis pathway. In FIG. 1, cholesterol is converted to pregnenolone, which then undergoes conversion along the mineralcortioid biosynthesis pathway to progesterone, 11-deoxycorticosterone, and corticosterone (and then to 18-hydroxycorticosterone and aldosterone, not pictured). The conversion to corticosterone occurs via the enzyme 11β-hydroxylase. 11β-hydroxylase is also featured in the glucocorticoid pathway. For the glucocorticoid biosynthesis pathway, pregnenolone or progesterone is converted via the 17α-hydroxylase activity of cytochrome P450-17 ("CYP17") to either 17α-hydroxypregnenolone or 17α-hydroxyprogesterone. 17α-hydroxyprogesterone is converted to 11-deoxycortisol, which in turn is converted to cortisol by 11β-hydroxylase. CYP17 is also featured in the androgen biosynthesis pathway. CYP17, utilizing its 17,20-lyase activity, converts 17α-hydroxypregnenolone to dehydroepiandrosterone ("DHEA") and 17α-hydroxyprogesterone to adostenedione. Adostenedione, in turn, is converted to testosterone by 17β-hydroxysteroid dehydrogenase, while testosterone is converted to dihydrotestosterone ("DHT") by 5α-reductase.

In some alternatives, a hormonal therapy agent is provided to a patient to selectively inhibit the androgen biosynthesis pathway. Selective inhibition of this pathway is desirable given that a patient receiving such an agent will not require hormone replacement therapy. Hormone replacement therapy is often required when non-selective hormonal therapy agents, such as abiraterone are provided, resulting in the inhibition of mineralocorticoid biosynthesis and/or glucocorticoid biosynthesis. Such inhibition may afford side effects, causes the patient to take additional drugs, reduce patient compliance, and/or impair the patient's quality of life. Additionally, it is contemplated that some non-selective hormonal therapy agents, such as abiraterone, might be expected to interfere with or counteract the anti-cancer potential of 1,4-naphthoquinone analogs, for example, by competing with 1,4-naphthoquinone analogs for binding to the androgen receptor or heat shock proteins associated with the androgen receptor. Therefore, it is surprising that the naphthoquinone analogs disclosed herein can be used in combination with abiraterone.

In some alternatives, a hormonal therapy agent is provided to a patient to selectively inhibit the 17,20-lyase activity of CYP17. Such inhibition will result in the selective decrease of DHEA and androstenedione production, while not affecting mineralocorticoid biosynthesis and glucocorticoid biosynthesis. Indeed, selectivity targeting CYP17's 17,20-lyase activity, while leaving the 17α-hydroxylase activity of CYP17 relatively undisturbed should afford limited side effects and be less likely to require the concomitant administration of a hormone replacement, such as prednisone.

Inhibitors of 17,20-lyase activity of cytochrome P450-17 ("CYP-17") are known in the art. Steroid-type inhibitors of 17,20-lyase activity are disclosed in, for example, WO 92/15404, WO 93/20097, EP-A 288053, and EP-A 413270, such compounds being incorporated herein by reference. Non-steroid-type compounds are disclosed in, for example, in WO94/27989, WO96/14090, WO97/00257; WO95/09157; U.S. Pat. No. 5,491,161; WO99/18075; WO99/54309; WO03/027085; and EP0724591, such compounds being expressly incorporated herein by reference in their entireties. Additional compounds include, but are not limited to, compounds disclosed in U.S. Pat. Nos. 8,236,962; 8,263,635; and U.S. Patent Application No. 20100305078; the compounds described therein being expressly incorporated herein by reference in their entireties.

Specific examples of selective 17,20-lyase inhibitors for use in certain alternatives include 6-(7-hydroxy-6,7-dihydro-5H-pyrrolo[1,2-c]imidazole-7-yl)-2-naphthamide; 6-(7-hydroxy-6,7-dihydro-5H-pyrrolo[1,2-c]imidazole-7-yl)-N-methyl-2-naphthamide; N-ethyl-6-(7-hydroxy-6,7-dihydro-5H-pyrrolo[1,2-c]imidazole-7-yl)-2-naphthamide; N-cyclopropyl-6-(7-hydroxy-6,7-dihydro-5H-pyrrolo[1,2-c]imidazole-7-yl)-2-naphthamide; 6-(7-hydroxy-6,7-dihydro-5H-pyrrolo[1,2-c]imidazole-7-yl)-N-isopropyl-2-naphthamide; N,N-diisopropyl-6-(7-hydroxy-6,7-dihydro-5H-pyrrolo[1,2-c]imidazole-7-yl)-2-naphthamide; 6-[1-hydroxy-1-(1-methyl-1H-imidazol-5-yl)ethyl]-N-methyl-naphthalene-2-carboxamide; 6-(6,7-dihydro-5H-pyrrolo[1,2-c]imidazole-7-yl)-N-methyl-2-naphthamide; and 6-(7-hydroxy-6,7-dihydro-6,6-dimethyl-5H-pyrrolo[1,2-c]imidazole-7-yl)-N-isopropyl-2-naphthamide. See Kaku et al., Bioorg. Med. Chem. (2011) 19, 6383-99.

Moreover, preferred examples of selective 17,20-lyase inhibitors include orteronel and VT-464. See Kaku et al., Bioorg. Med. Chem. (2011) 19, 6383-99; Eisner et al. J. Clin. Oncol. "VT-464: A novel, selective inhibitor of P450c17 (CYP17)-17,20 lyase for castration-refractory prostate cancer (CRPC).

One of skill in the art can readily determine additional examples of selective 17,20-lyase inhibitors by screening inhibitors of CYP17 for both 17,20-lyase inhibition and hydroxylase inhibition, such as 17α-hydroxylase inhibition. In some alternatives, a compound is a selective inhibitor if there is a 5-fold difference between lyase and hydroxylase inhibition. In other alternatives, a selective inhibitor will have an inhibition that is at least or equal to a 10, 20, 30, 50, or 100-fold difference or any fold difference in between these numbers. Methods to determine selective inhibition are known in the art.

In some alternatives, a hormonal therapy agent is selected from the group consisting of cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, and ganirelix or any combination thereof.

In other alternatives, the hormonal therapy agent is selected from the group consisting of enzalutamide; ARN-509; vinclozolin; galeterone; ketoconazole; L-39; VT-464; orteronel; aminoglutethimide; prochloraz; dutasteride; izonsteride; turosteride; epristeride; genisterin; gossypol; equol; 18β-glycyrrhetinic acid; altraric acid; N-butylbenzene-sulfonamide; and 3,3'-diindolylmethane or any combination thereof. In other alternatives, the hormonal therapy agent is selected from the group consisting of enzalutamide; ARN-509; and vinclozolin or any combination thereof. In other alternatives, the hormonal therapy agent is selected from the group consisting of galeterone; L-39; VT-464; orteronel; aminoglutethimide; and prochloraz or any combination thereof. In other alternatives, the hormonal therapy agent is selected from the group consisting of dutasteride; izonsteride; turosteride; and epristeride or any combination thereof. In other alternatives, the hormonal therapy agent is selected from the group consisting of genisterin; gossypol; equol; 18β-glycyrrhetinic acid; altraric acid; N-butylbenzene-sulfonamide; and 3,3'-diindolylmethane or any combination thereof. In other alternatives, the hormonal therapy agent is selected from the group consisting of deslorelin; nafarelin; cetrorelix; and ganirelix or any combination thereof. In other alternatives, the hormonal therapy agent is selected from the group consisting of degarelix, abiraterone, degarelix, and dutasteride.

In some alternatives, the hormonal therapy agent is a luteinizing hormone-releasing hormone (LHRH) antagonist or agonist. In some alternatives, the hormonal therapy agent is a gonadotropin-releasing hormone agonist. In some alternatives, the hormonal therapy agent is a gonadotropin-releasing hormone agonist selected from deslorelin or nafarelin or a combination thereof. In some alternatives, the hormonal therapy agent is a gonadotropin-releasing hormone antagonist. In some alternatives, the hormonal therapy agent is a gonadotropin-releasing hormone antagonist selected from cetrorelix or ganirelix or a combination thereof.

In some alternatives, one or more of the hormone therapy agents described above are administered to the patient before administering a compound of Formula (I), (II), (III), or (IV). In other alternatives, one or more of the hormone therapy agents described above are administered to the patient after administering a compound of Formula (I), (II), (III), or (IV). In other alternatives, one or more of the hormone therapy agents described above are concurrently (within a few hours) administered to the patient with a compound of Formula (I), (II), (III), or (IV).

In some alternatives, the androgen that is decreased in the subject is testosterone, dihydrotestosterone (DHT), androsterone, androstenediol, androstenedione, dehydroepiandrosterone (DHEA), and/or dehydroepiandrosterone sulfate (DHEA-S). In some alternatives, a subject's serum testosterone level is decreased with one or more anti-androgen agents or androgen ablation agents. Preferably, the androgen deprivation therapy is provided during a period in which one or more compounds of Formulae (I), (II), (III), and (IV) are provided. In some alternatives, androgen deprivation therapy reduces the production of testosterone in a patient. In some embodiments, androgen deprivation therapy reduces the production of one or more hormones selected from testosterone, dihydrotestosterone (DHT), androsterone, androstenediol, androstenedione, dehydroepiandrosterone (DHEA), and dehydroepiandrosterone sulfate (DHEA-S).

In some alternatives, a subject suffering from prostate cancer is classified or identified as a subject in need of a therapy for prostate cancer and said subject is provided a hormone therapy agent that reduces the subject's androgen levels while said subject is receiving one or more compounds of Formulas (I), (II), (III), and (IV). Optionally, the inhibition in prostate cancer cell growth or an inhibition in prostate cancer advancement is evaluated. Optionally, the delaying prostate cancer cell growth or delaying prostate cancer advancement is evaluated. A subject can be identified as one in need of a therapy for prostate cancer using conventional clinical pathology including, biopsy, CT scan, MRI, digital examination, Gleason score, or PSA level. A patient may receive a PET scan, which evaluate the activity of the tumor cells (glucose metabolism). Similarly, the inhibition or delay of cancer cell growth in said subject after receiving the treatment can be evaluated using conventional clinical pathology including, biopsy, CT scan, MRI, digital examination, Gleason score, or PSA level.

In some alternatives, the hormone therapy agent that can be used with any one or more of the methods or treatments described herein is selected from the group consisting of an antiandrogen (including steroidal antiandrogens and nonsteroidal antiandrogens), an estrogen, a luteinizing hormone-releasing hormone (LHRH) agonist, and a LHRH antagonist or any combination thereof. Steroidal antiandrogen agents include, but are not limited to, cyproterone acetate and finasteride. Nonsteroidal antiandrogens include, but are not limited to, flutamide, nilutamide and bicalutamide. Estrogen agents include, but are not limited to, diethylstilbestrol (DES), megestrol acetate, fosfestrol, and estamustine phosphate. LHRH agonist agents include, but are not limited to, leuprolide, triptorelin, goserelin, histrelin and buserelin. LHRH antagonist agents include, but are not limited to, abarelix and degarelix. Desirably, one or more of the compounds selected from the group consisting of cyproterone acetate, finasteride, flutamide, abiraterone, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, and ganirelix or any combination thereof are used in the methods and treatments (compositions) described herein, wherein one or more of the compounds of Formulae (I), (II), (III), and (IV) (e.g., a compound of Table 1) are provided before, during, and/or after providing said cyproterone acetate, finasteride, flutamide, abiraterone, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, or ganirelix or any combination thereof.

As mentioned above, prostate cancer can be treated by hormone, therapy agents, however; hormone therapy agents alone can result in the development of castration-resistant prostate cancer (CRPC). For example, hormonal therapy can initially deliver a response in a subject suffering from prostate cancer, however, the return of hormone-refractory tumors invariably prevents long-term patient survival. More effective strategies are needed to extend life expectancy and improve the quality of life for patients with advanced prostate cancer. Accordingly, some aspects disclosed herein concern methods for ameliorating or inhibiting or reducing or delaying the onset of castration-resistant prostate cancer (CRPC) or treatments (e.g., compositions used for the purpose of ameliorating or inhibiting or reducing or delaying the onset of CRPC), whereby one or more of the compounds of Formulae (I), (II), (III), and (IV) are provided before, during and/or after providing cyproterone acetate, finasteride, abiraterone, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, or ganirelix or any combination thereof. Optionally, the inhibition in prostate cancer cell growth, an inhibition in prostate cancer advancement, or delaying the onset of CRPC is evaluated before during or after the therapy. Optionally, a patient with prostate cancer is classified as a subject in need of an agent that ameliorates, reduces, delays, or inhibits the onset of CRPC prior to receiving one or more of the combination therapies described herein. A subject can be identified as one in need of a therapy for prostate cancer using conventional clinical pathology including, biopsy, CT scan, PET scan, MRI, digital examination, Gleason score, or PSA level.

VI. Combination Therapies

In some alternatives, the compounds disclosed herein, such as a compound of Formula (I), (II), (III), or (IV) (e.g., a compound of Table 1), or a pharmaceutically acceptable salt thereof, or a pharmaceutical composition that includes a compound described herein, can be used in combination with one or more hormone therapy agents. Some alternatives disclosed herein relate to a method of ameliorating or treating a neoplastic disease that can include administering or providing to a subject suffering from a neoplastic disease a therapeutically effective amount of one or more compounds described herein (e.g., a compound of Formula (I), (II), (III), or (IV), or a pharmaceutically acceptable salt thereof), in combination with one or more additional agents, including hormone therapy agents (referred to as "combination therapy").

Examples of additional agents that can be used in combination with a compound of Formula (I), (II), (III), or (IV), or a pharmaceutically acceptable salt thereof, or a pharmaceutical composition that includes a compound of Formula (I), (II), (III), or (IV), or a pharmaceutically acceptable salt thereof, include, but are not limited to, agents that can decrease the subject's serum androgen levels (e.g., cyproterone acetate, abiraterone, finasteride, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, or ganirelix or any combination thereof).

In some alternatives, the neoplastic disease can be cancer. In some alternatives, the neoplastic disease can be a tumor such as a solid tumor or metastasis. In an alternative, the neoplastic disease can be prostate cancer, such as stage I, stage II, stage III or stage IV prostate cancer and in some alternatives, the prostate cancer can be CRPC, prostate cancer that has extended beyond the outer condensed fibromuscular band, also known as the capsule, or metastasis stemming from prostate cancer. In some alternatives, the prostate cancer is androgen dependent. Therefore, in some alternatives, a compound of Formula (I), (II), (III), or (IV), or a pharmaceutically acceptable salt thereof, or a pharmaceutical composition that includes a compound of Formula (I), (II), (III), or (IV), or a pharmaceutically acceptable salt thereof, is used in combination with one or more hormone therapy agents for the use in treating, inhibiting, delaying, or ameliorating progression of prostate cancer, such as stage I, stage II, stage III or stage IV prostate cancer growth of prostate cancer cells, or for inhibiting or preventing the onset of androgen-dependent prostate cancer, or for decreasing the size of a prostate tumor, or for inhibiting the onset of metastasis associated with prostate cancer. In some alternatives, a compound of Formula (I), (II), (III), or (IV), or a pharmaceutically acceptable salt thereof, or a pharmaceutical composition that includes a compound of Formula (I), (II), (III), or (IV), or a pharmaceutically acceptable salt thereof, is used in combination with one or more hormone therapy agents for the use in increasing the survival rate of a patient suffering from prostate cancer.

In some alternatives, a compound of Formula (I), (II), (III), or (IV), or a pharmaceutically acceptable salt thereof, or a pharmaceutical composition that includes a compound of Formula (I), (II), (III), or (IV), or a pharmaceutically acceptable salt thereof, is used in combination with surgical orchiectomy and/or one or more of the hormone therapy agents (e.g. cyproterone acetate, finasteride, abiraterone, flutamide, nilutamide, bicalutamide, diethylstilbestrol (DES), megestrol acetate, fosfestrol, estamustine phosphate, leuprolide, triptorelin, goserelin, histrelin, buserelin, abarelix, degarelix, orteronel, VT-464, enzalutamide, ARN-509, vinclozolin, galeterone, ketoconazole, L-39, aminoglutethimide, prochloraz, dutasteride, izonsteride, turosteride, epristeride, genisterin, gossypol, equol, 18β-glycyrrhetinic acid, altraric acid, N-butylbenzene-sulfonamide, 3,3'-diindolylmethane, deslorelin, nafarelin, cetrorelix, or ganirelix or any combination thereof) for the use in increasing the survival rate of a patient suffering from CRPC. In some alternatives, a compound of Formula (I), (II), (III), or (IV), or a pharmaceutically acceptable salt thereof, or a pharmaceutical composition that includes a compound of Formula (I), (II), (III), or (IV), or a pharmaceutically acceptable salt thereof, is used in combination with one or more hormone therapy agents for the use in reducing the size of a tumor or further expansion of cancer cells in a patient suffering from prostate cancer, such as stage I, stage II, stage III or stage IV prostate cancer. Some alternatives involve methods for inducing remission of prostate cancer, such as stage I, stage II, stage III or stage IV prostate cancer, whereby one or more of the compounds of Formulae (I), (II), (III), and (IV) are provided before, during and/or after providing a hormone therapy agent to a subject suffering from prostate cancer. In some alternatives, the methods disclosed herein can result in complete remission of prostate cancer, such as stage I, stage II, stage III or stage IV prostate cancer. In some alternatives, the methods can result in partial remission of prostate cancer; such as stage I, stage II, stage III or stage IV prostate cancer.

Normal serum testosterone ranges between 1000-300 ng/dL. In some alternatives, a subject is provided a combination therapy, as described herein, whereby a reduction in the treated subject's serum testosterone level to at least about ≤80, ≤70, ≤60, ≤50, ≤40, ≤30, ≤20, or ≤10 ng/dL is obtained. In some alternatives, a subject is provided a combination therapy that reduces the subject's serum testosterone level to at least about ≤50 ng/dL. In some alternatives, a subject is treated with a combination therapy that results in a reduction in the subject's serum testosterone level to at least about ≤20 ng/dL. In some alternatives, a subject is treated with a combination therapy, as described herein, that reduces the subject's serum testosterone level to at least about or any number in between the range of 120-70, 100-60, 80-40, 70-30, 50-20, 40-10, 30-10, or 20-10 ng/dL. In some alternatives, a subject is treated with a combination therapy that produces a reduction in the subject's serum testosterone level to about ≤95%, ≤90%, ≤80%, ≤70%, ≤60%, or ≤50% that of a healthy male. In some alternatives, a subject is treated with a combination therapy that results in a reduction in the subject's serum testosterone level to the range of at least about or any number in between the range of about 5-20%, 10-30%, 20-40%, 30-50%, 40-60%, or 50-70% that of a healthy male. In some alternatives, a subject is treated with a combination therapy that results in a reduction in the subject's serum testosterone level to the range of at least about or any number in between the range of about 1-2%, 2-4%, 1-5%, 4-6%, 4-8%, or 5-10% that of a healthy male.

Intermittent hormonal therapy (IHT) is an alternative to continuous hormonal therapy, which may delay progression of hormone-refractory disease (i.e., CRPC). For example, intermittent therapy can be used for a period of 6 months on, followed by a period of 6 months off. In some alternatives, one or more hormonal therapy agents is provided for one month on, followed by one month off. In some alternatives, one or more therapy agents are provided for three months on, followed by three months off. Accordingly, one or more of the compounds of Formula (I), (II), III) or (IV), can be provided before, during and/or after administering one or more hormonal therapy agents, as described above, so as to reduce or inhibit or delay the onset of CRPC.

A non-limiting list of example combination of compounds described herein (such as compounds of Formulae (I), (II), (III), and (IV)), or a pharmaceutically acceptable salt thereof, or a pharmaceutical composition that includes a compound described herein, with one or more hormonal therapy agents are provided in Tables 1 and 2. Table 1 provides a shorthand name for each compound (e.g., "F01") and a shorthand name for each therapy (e.g., "AT01"). Each numbered 'X' compound in Table 2 has a corresponding compound structure provided in Table 1. Likewise, each numbered 'Y' therapy in Table 2 has a corresponding therapy provided in Table 1. Therefore, each "X:Y" entry in Table 2 provides an example of a combination of a compound and a therapy that can be used to treat a subject suffering from prostate cancer. For example, the combination designated as "F02:AT04" in Table 2 provides a combination of

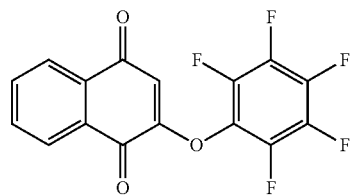 [SMILES: O=C1C=C(Oc2c(F)c(F)c(F)c(F)c2F)C(=O)c2ccccc21]

2-(2,3,4,5,6-pentafluorophenoxy)-1,4-naphthoquinone and flutamide that can be used to treat a subject suffering from prostate cancer, such as stage I, stage II, stage III or stage IV prostate cancer. Each of the combinations provided in Table 2 can be used with one, two, three or more additional agents described herein.

TABLE 1

Exemplary compounds and therapies of the present disclosure.

| Compound | | Additional Therapy | |
|---|---|---|---|
| 2-phenoxy-1,4-naphthoquinone | (R1) (F01) | cyproterone acetate | (AT01) |

TABLE 1-continued

Exemplary compounds and therapies of the present disclosure.

| Compound | | Additional Therapy | |
|---|---|---|---|
| 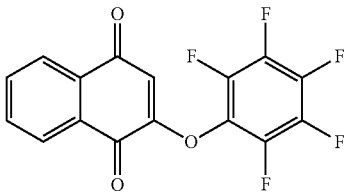<br>2-(2,3,4,5,6-pentafluorophenoxy)-1,4-naphthoquinone (R2) | (F02) | finasteride | (AT02) |
| 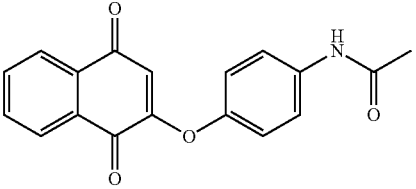<br>2-(4-acetamidophenoxy)-1,4-naphthoquinone (R3) | (F03) | bicalutamide | (AT03) |
| 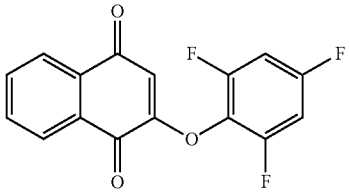<br>2-(2,4,6-trifluorophenoxy)-1,4-naphthoquinone (R4) | (F04) | flutamide | (AT04) |
| 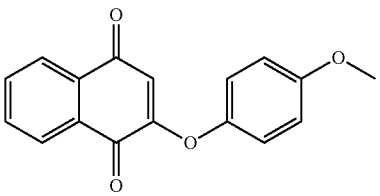<br>2-(4-methoxyphenoxy)-1,4-naphthoquinone (R5) | (F05) | nilutamide | (AT05) |
| 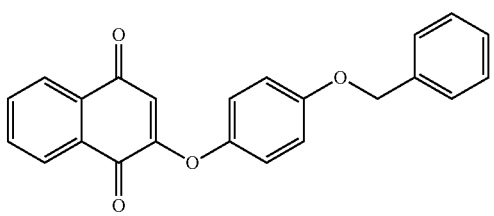<br>2-(4-benzyloxy)phenoxy)-1,4-naphthoquinone (R6) | (F06) | abiraterone | (AT06) |
| 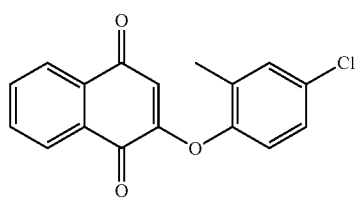<br>2-(4-chloro-2-methylphenoxy)-1,4-naphthoquinone (R7) | (F07) | diethyl-<br>stilbestrol<br>(DES) | (AT07) |

TABLE 1-continued

Exemplary compounds and therapies of the present disclosure.

| Compound | | Additional Therapy | |
|---|---|---|---|
| 2-(3-methylphenoxy)-1,4-naphthoquinone (R8) | (F08) | megestrol acetate | (AT08) |
| 2-(naphthalene-2-yloxy)-1,4-naphthoquinone (R9) | (F09) | fosfestrol | (AT09) |
| 2-(4-hydroxyphenoxy)-1,4-naphthoquinone (R10) | (F10) | estamustine phosphate | (AT10) |
| 2-(4-(2-dimethylaminoethyl)phenoxy)-1,4-naphthoquinone (R11) | (F11) | leuprolide | (AT11) |
| 2-(4-nitrophenoxy)naphthalene-1,4-dione (R12) | (F12) | triptorelin | (AT12) |

TABLE 1-continued

Exemplary compounds and therapies of the present disclosure.

| Compound | | Additional Therapy | |
|---|---|---|---|
| 2-(2-benzyl-4-chlorophenoxy)naphthalene-1,4-dione (R13) | (F13) | goserelin | (AT13) |
| 2-(4-chlorophenoxy)naphthalene-1,4-dione (R16) | (F14) | histrelin | (AT14) |
| 2-(4-chloro-3-methylphenoxy)naphthalene-1,4-dione (R14) | (F15) | buserelin | (AT15) |
| 2-(2-chloro-4-methoxyphenoxy)naphthalene-1,4-dione (R15) | (F16) | abarelix | (AT16) |
| 2-(3,5-difluorophenoxy)naphthalene-1,4-dione (R17) | (F17) | degarelix | (AT17) |

TABLE 1-continued
Exemplary compounds and therapies of the present disclosure.
| Compound | Additional Therapy | |
|---|---|---|
| 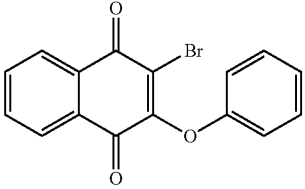<br>2-bromo-3-phenoxy-1,4-naphthoquinone (Y4) | (F18) surgical orchiectomy | (AT18) |
| 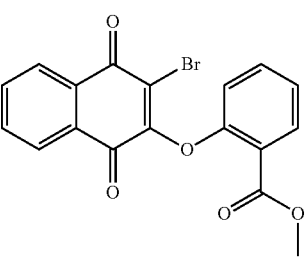<br>methyl 3-bromo-1,4-naphthoquinon-2-yl-salicylate (Y12) | (F19) VT-464 | (AT19) |
| 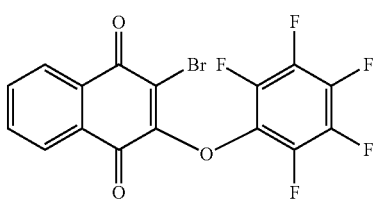<br>2-bromo-3-(2,3,4,5,6-pentafluorophenoxy)-1,4-naphthoquinone | (F20) enzalutamide | (AT20) |
| 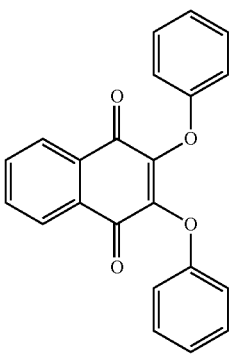<br>2,3-diphenoxy-1,4-naphthoquinone (B9) | (F21) ARN-509 | (AT21) |

TABLE 1-continued

Exemplary compounds and therapies of the present disclosure.

| Compound | | Additional Therapy | |
|---|---|---|---|
| 2,3-bis(2,4,6-trifluorophenoxy)naphthalene-1,4-dione (B10) | (F22) | vinclozolin | (AT22) |
| 2,3-bis(4-chloro-2-methylphenoxy)-1,4-naphthoquinone (B11) | (F23) | galeterone | (AT23) |
| 2,3-bis(4-hydroxyphenoxy)-1,4-naphthoquinone (B12) | (F24) | ketoconazole | (AT24) |

TABLE 1-continued

Exemplary compounds and therapies of the present disclosure.

| Compound | Additional Therapy | |
|---|---|---|
| N,N'-(((1,4-dioxo-1,4-dihydronaphthalene-2,3-diyl)bis(oxy))bis(4,1-phenylene))diacetamide (B14) | (F25) L-39 | (AT25) |
| 2,3-bis(m-tolyloxy)naphthalene-1,4-dione (B15) | (F26) aminoglutethimide | (AT26) |
| 2,3-bis(perfluorophenoxy)naphthalene-1,4-dione (B16) | (F27) prochloraz | (AT27) |

TABLE 1-continued
Exemplary compounds and therapies of the present disclosure.
| Compound | | Additional Therapy | |
|---|---|---|---|
| 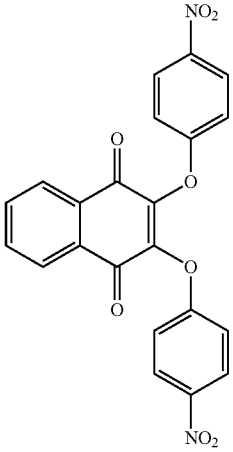 2,3-bis(4-nitrophenoxy)naphthalene-1,4-dione (B17) | (F28) | dutasteride | (AT28) |
| 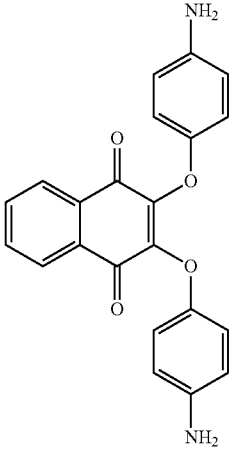 2,3-bis(4-aminophenoxy)-1,4-naphthoquinone | (F29) | izonsteride | (AT29) |
| 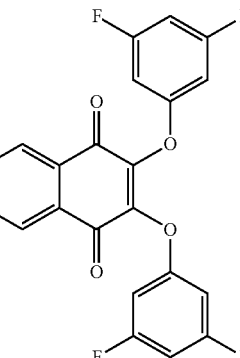 2,3-bis(3,5-difluorophenoxy)naphthalene-1,4-dione | (F30) | turosteride | (AT30) |

TABLE 1-continued
Exemplary compounds and therapies of the present disclosure.
| Compound | | Additional Therapy | |
|---|---|---|---|
| 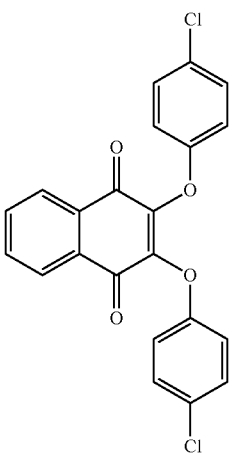{br}2,3-bis(4-chlorophenoxy)naphthalene-1,4-dione | (F31) | epristeride | (AT31) |
| 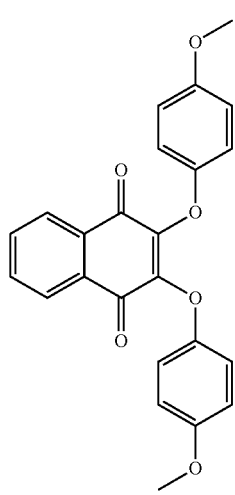{br}2,3-bis(4-methoxyphenoxy)naphthalene-1,4-dione | (F32) | genisterin | (AT32) |

TABLE 1-continued
Exemplary compounds and therapies of the present disclosure.
| Compound | | Additional Therapy | |
|---|---|---|---|
| 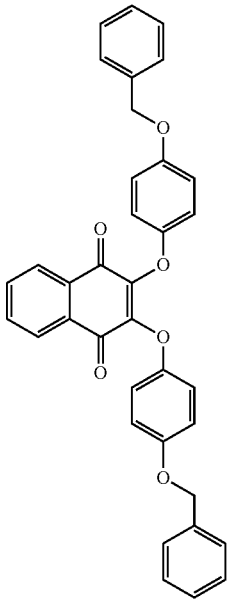
2,3-bis(4-(benzyloxy)phenoxy)naphthalene-1,4-dione | (F33) | gossypol | (AT33) |
| 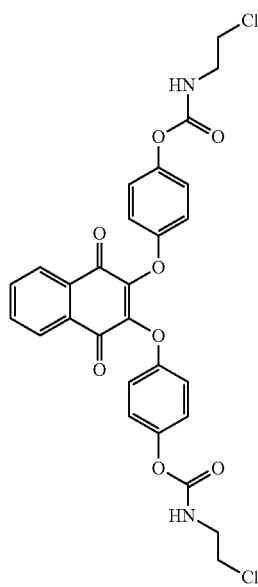
2,3-bis(4-((2-chloroethyl)carbamoyloxy)phenoxy)-1,4-naphthoquinone (N5) | (F34) | equol | (AT34) |
| 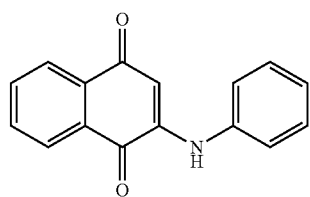
2-(phenylamino)naphthalene-1,4-dione (W1) | (F35) | 18β-glycyrrhetinic acid | (AT35) |

TABLE 1-continued

Exemplary compounds and therapies of the present disclosure.

| Compound | | Additional Therapy | |
|---|---|---|---|
| 2-((4-(trifluoromethoxy)phenyl)amino)naphthalene-1,4-dione | (F36) | altraric acid | (AT36) |
| 2-N-acetylamino-3-chloro-1,4-naphthoquinone | (F37) | N-butylbenzene-sulfonamide | (AT37) |
| N-(1,4-dioxo-3-phenoxy-1,4-dihydronaphthalen-2-yl)acetamide | (F38) | 3,3'-diindolyl-methane | (AT38) |
| N-(3-(4-chlorophenoxy)-1,4-dioxo-1,4-dihydronaphthalen-2-yl)acetamide | (F39) | deslorelin | (AT39) |
| N-(4-((3-acetamido-1,4-dioxo-1,4-dihydronaphthalen-2-yl)oxy)phenyl)acetamide | (F40) | nafarelin | (AT40) |

TABLE 1-continued

Exemplary compounds and therapies of the present disclosure.

| Compound | | Additional Therapy | |
|---|---|---|---|
| 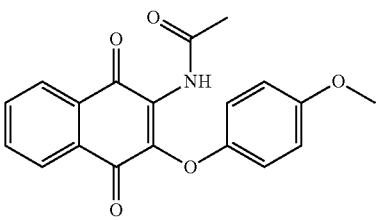 N-(3-(4-methoxyphenoxy)-1,4-dioxo-1,4-dihydronaphthalen-2-yl)acetamide | (F41) | cetrorelix | (AT41) |
| 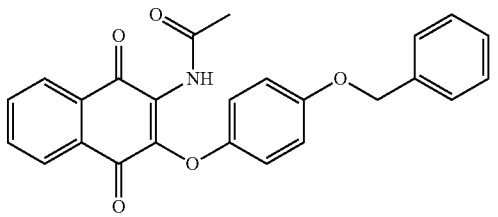 N-(3-(4-(benzyloxy)phenoxy)-1,4-dioxo-1,4-dihydronaphthalen-2-yl)acetamide | (F42) | ganirelix | (AT42) |
| 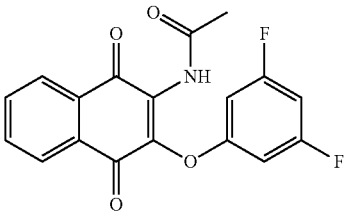 N-(3-(3,5-difluorophenoxy)-1,4-dioxo-1,4-dihydronaphthalen-2-yl)acetamide | (F43) | orteronel | (AT43) |
| 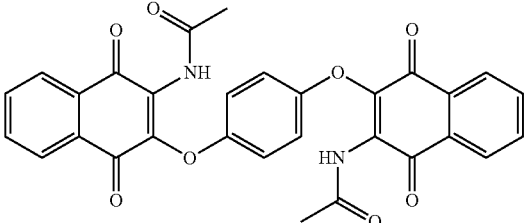 N,N'-((1,4-phenylenebis(oxy))bis(1,4-dioxo-1,4-dihydronaphthalene-3,2-diyl))diacetamide | (F44) | | |
| 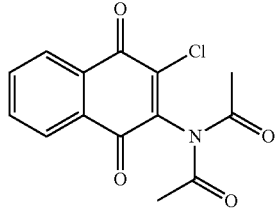 [SMILES: CC(=O)N(C(C)=O)C1=C(Cl)C(=O)c2ccccc2C1=O] | (F45) | | |

TABLE 1-continued

Exemplary compounds and therapies of the present disclosure.

| Compound | Additional Therapy |
|---|---|
| Methyl 2-((8-hydroxy-3-methyl-1,4-dioxo-1,4-dihydronaphthalen-2-yl)thio)acetate | (F46) |
| 5-methoxy-2-methyl-1,4-naphthoquinone | (F47) |
| 5-(4-iodobutoxy)-2-methyl-1,4-naphthoquinone | (F48) |
| 5-(3-iodopropoxy)-2-methyl-1,4-naphthoquinone | (F49) |
| 5-isopropoxy-2-methyl-1,4-naphthoquinone | (F50) |

TABLE 1-continued
Exemplary compounds and therapies of the present disclosure.
| Compound | Additional Therapy |
|---|---|
| 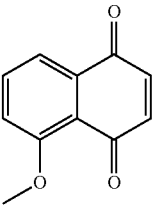<br>5-methoxy-1,4-naphthoquinone (F51) | |
| 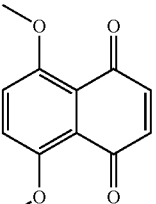<br>5,8-dimethoxy-1,4-naphthoquinone (F52) | |
| 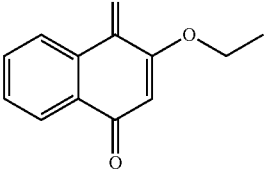<br>2-ethoxy-1,4-naphthoquinone (F53) | |
| 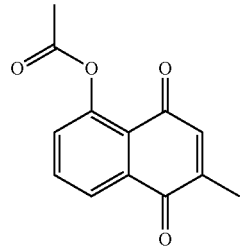<br>6-methyl-5,8-dioxo-5,8-dihydronaphthalen-1-yl acetate (F54) | |
| 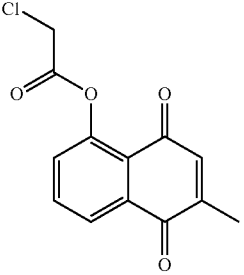<br>6-methyl-5,8-dioxo-5,8-dihydronaphthalen-1-yl 2-chloroacetate (F55) | |

TABLE 1-continued

Exemplary compounds and therapies of the present disclosure.

| Compound | Additional Therapy |
|---|---|
| 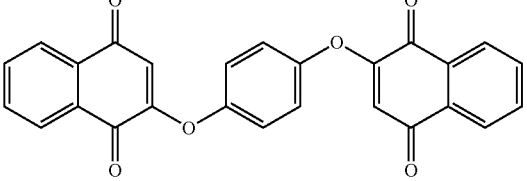<br>2,2'-(1,4-phenylenebis(oxy))bis(naphthalene-1,4-dione) (G1) (F56) | |
| 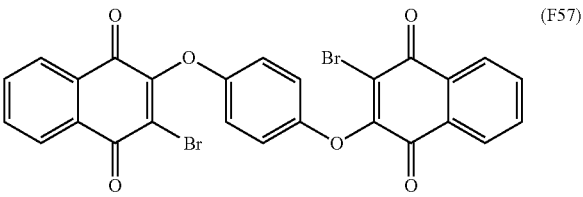<br>3,3'-(1,4-phenylenebis(oxy))bis(2-bromonaphthalene-1,4-dione) (G6) (F57) | |
| 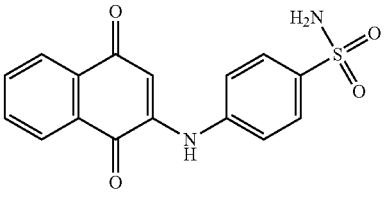<br>4-((1,4-dioxo-1,4-dihydronaphthalen-2-yl)amino)benzenesulfonamide (F58) | |
| 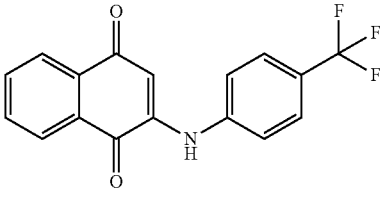<br>2-((4-(trifluoromethyl)phenyl)amino)naphthalene-1,4-dione (F59) | |
| 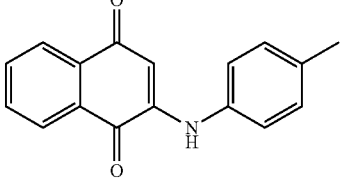<br>2-(p-tolylamino)naphthalene-1,4-dione (F60) | |
| 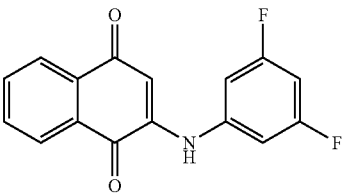<br>2-((3,5-difluorophenyl)amino)naphthalene-1,4-dione (F61) | |

TABLE 1-continued

Exemplary compounds and therapies of the present disclosure.

| Compound | Additional Therapy |
|---|---|
| 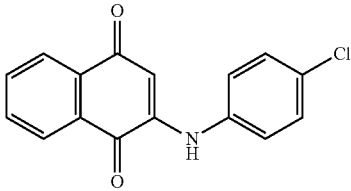<br>2-((4-chlorophenyl)amino)naphthalene-1,4-dione | (F62) |
| 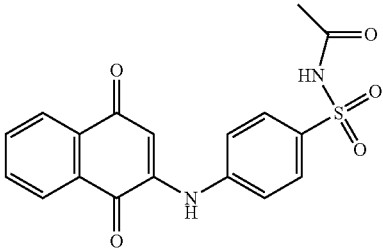<br>N-((4-(((1,4-dioxo-1,4-dihydronaphthalen-2-yl)amino)phenyl)sulfonyl)acetamide | (F63) |

TABLE 2

| X:Y | X:Y | X:Y | X:Y | X:Y | X:Y | X:Y |
|---|---|---|---|---|---|---|
| F01:AT01 | F02:AT01 | F03:AT01 | F04:AT01 | F05:AT01 | F06:AT01 | F07:AT01 |
| F01:AT02 | F02:AT02 | F03:AT02 | F04:AT02 | F05:AT02 | F06:AT02 | F07:AT02 |
| F01:AT03 | F02:AT03 | F03:AT03 | F04:AT03 | F05:AT03 | F06:AT03 | F07:AT03 |
| F01:AT04 | F02:AT04 | F03:AT04 | F04:AT04 | F05:AT04 | F06:AT04 | F07:AT04 |
| F01:AT05 | F02:AT05 | F03:AT05 | F04:AT05 | F05:AT05 | F06:AT05 | F07:AT05 |
| F01:AT06 | F02:AT06 | F03:AT06 | F04:AT06 | F05:AT06 | F06:AT06 | F07:AT06 |
| F01:AT07 | F02:AT07 | F03:AT07 | F04:AT07 | F05:AT07 | F06:AT07 | F07:AT07 |
| F01:AT08 | F02:AT08 | F03:AT08 | F04:AT08 | F05:AT08 | F06:AT08 | F07:AT08 |
| F01:AT09 | F02:AT09 | F03:AT09 | F04:AT09 | F05:AT09 | F06:AT09 | F07:AT09 |
| F01:AT10 | F02:AT10 | F03:AT10 | F04:AT10 | F05:AT10 | F06:AT10 | F07:AT10 |
| F01:AT11 | F02:AT11 | F03:AT11 | F04:AT11 | F05:AT11 | F06:AT11 | F07:AT11 |
| F01:AT12 | F02:AT12 | F03:AT12 | F04:AT12 | F05:AT12 | F06:AT12 | F07:AT12 |
| F01:AT13 | F02:AT13 | F03:AT13 | F04:AT13 | F05:AT13 | F06:AT13 | F07:AT13 |
| F01:AT14 | F02:AT14 | F03:AT14 | F04:AT14 | F05:AT14 | F06:AT14 | F07:AT14 |
| F01:AT15 | F02:AT15 | F03:AT15 | F04:AT15 | F05:AT15 | F06:AT15 | F07:AT15 |
| F01:AT16 | F02:AT16 | F03:AT16 | F04:AT16 | F05:AT16 | F06:AT16 | F07:AT16 |
| F01:AT17 | F02:AT17 | F03:AT17 | F04:AT17 | F05:AT17 | F06:AT17 | F07:AT17 |
| F01:AT18 | F02:AT18 | F03:AT18 | F04:AT18 | F05:AT18 | F06:AT18 | F07:AT18 |
| F01:AT19 | F02:AT19 | F03:AT19 | F04:AT19 | F05:AT19 | F06:AT19 | F07:AT19 |
| F01:AT20 | F02:AT20 | F03:AT20 | F04:AT20 | F05:AT20 | F06:AT20 | F07:AT20 |
| F01:AT21 | F02:AT21 | F03:AT21 | F04:AT21 | F05:AT21 | F06:AT21 | F07:AT21 |
| F01:AT22 | F02:AT22 | F03:AT22 | F04:AT22 | F05:AT22 | F06:AT22 | F07:AT22 |
| F01:AT23 | F02:AT23 | F03:AT23 | F04:AT23 | F05:AT23 | F06:AT23 | F07:AT23 |
| F01:AT24 | F02:AT24 | F03:AT24 | F04:AT24 | F05:AT24 | F06:AT24 | F07:AT24 |
| F01:AT25 | F02:AT25 | F03:AT25 | F04:AT25 | F05:AT25 | F06:AT25 | F07:AT25 |
| F01:AT26 | F02:AT26 | F03:AT26 | F04:AT26 | F05:AT26 | F06:AT26 | F07:AT26 |
| F01:AT27 | F02:AT27 | F03:AT27 | F04:AT27 | F05:AT27 | F06:AT27 | F07:AT27 |
| F01:AT28 | F02:AT28 | F03:AT28 | F04:AT28 | F05:AT28 | F06:AT28 | F07:AT28 |
| F01:AT29 | F02:AT29 | F03:AT29 | F04:AT29 | F05:AT29 | F06:AT29 | F07:AT29 |
| F01:AT30 | F02:AT30 | F03:AT30 | F04:AT30 | F05:AT30 | F06:AT30 | F07:AT30 |
| F01:AT31 | F02:AT31 | F03:AT31 | F04:AT31 | F05:AT31 | F06:AT31 | F07:AT31 |
| F01:AT32 | F02:AT32 | F03:AT32 | F04:AT32 | F05:AT32 | F06:AT32 | F07:AT32 |
| F01:AT33 | F02:AT33 | F03:AT33 | F04:AT33 | F05:AT33 | F06:AT33 | F07:AT33 |
| F01:AT34 | F02:AT34 | F03:AT34 | F04:AT34 | F05:AT34 | F06:AT34 | F07:AT34 |
| F01:AT35 | F02:AT35 | F03:AT35 | F04:AT35 | F05:AT35 | F06:AT35 | F07:AT35 |
| F01:AT36 | F02:AT36 | F03:AT36 | F04:AT36 | F05:AT36 | F06:AT36 | F07:AT36 |
| F01:AT37 | F02:AT37 | F03:AT37 | F04:AT37 | F05:AT37 | F06:AT37 | F07:AT37 |
| F01:AT38 | F02:AT38 | F03:AT38 | F04:AT38 | F05:AT38 | F06:AT38 | F07:AT38 |
| F01:AT39 | F02:AT39 | F03:AT39 | F04:AT39 | F05:AT39 | F06:AT39 | F07:AT39 |
| F01:AT40 | F02:AT40 | F03:AT40 | F04:AT40 | F05:AT40 | F06:AT40 | F07:AT40 |
| F01:AT41 | F02:AT41 | F03:AT41 | F04:AT41 | F05:AT41 | F06:AT41 | F07:AT41 |
| F01:AT42 | F02:AT42 | F03:AT42 | F04:AT42 | F05:AT42 | F06:AT42 | F07:AT42 |

TABLE 2-continued

| X:Y | X:Y | X:Y | X:Y | X:Y | X:Y | X:Y |
|---|---|---|---|---|---|---|
| F01:AT43 | F02:AT43 | F03:AT43 | F04:AT43 | F05:AT43 | F06:AT43 | F07:AT43 |
| F08:AT01 | F09:AT01 | F10:AT01 | F11:AT01 | F12:AT01 | F13:AT01 | F14:AT01 |
| F08:AT02 | F09:AT02 | F10:AT02 | F11:AT02 | F12:AT02 | F13:AT02 | F14:AT02 |
| F08:AT03 | F09:AT03 | F10:AT03 | F11:AT03 | F12:AT03 | F13:AT03 | F14:AT03 |
| F08:AT04 | F09:AT04 | F10:AT04 | F11:AT04 | F12:AT04 | F13:AT04 | F14:AT04 |
| F08:AT05 | F09:AT05 | F10:AT05 | F11:AT05 | F12:AT05 | F13:AT05 | F14:AT05 |
| F08:AT06 | F09:AT06 | F10:AT06 | F11:AT06 | F12:AT06 | F13:AT06 | F14:AT06 |
| F08:AT07 | F09:AT07 | F10:AT07 | F11:AT07 | F12:AT07 | F13:AT07 | F14:AT07 |
| F08:AT08 | F09:AT08 | F10:AT08 | F11:AT08 | F12:AT08 | F13:AT08 | F14:AT08 |
| F08:AT09 | F09:AT09 | F10:AT09 | F11:AT09 | F12:AT09 | F13:AT09 | F14:AT09 |
| F08:AT10 | F09:AT10 | F10:AT10 | F11:AT10 | F12:AT10 | F13:AT10 | F14:AT10 |
| F08:AT11 | F09:AT11 | F10:AT11 | F11:AT11 | F12:AT11 | F13:AT11 | F14:AT11 |
| F08:AT12 | F09:AT12 | F10:AT12 | F11:AT12 | F12:AT12 | F13:AT12 | F14:AT12 |
| F08:AT13 | F09:AT13 | F10:AT13 | F11:AT13 | F12:AT13 | F13:AT13 | F14:AT13 |
| F08:AT14 | F09:AT14 | F10:AT14 | F11:AT14 | F12:AT14 | F13:AT14 | F14:AT14 |
| F08:AT15 | F09:AT15 | F10:AT15 | F11:AT15 | F12:AT15 | F13:AT15 | F14:AT15 |
| F08:AT16 | F09:AT16 | F10:AT16 | F11:AT16 | F12:AT16 | F13:AT16 | F14:AT16 |
| F08:AT17 | F09:AT17 | F10:AT17 | F11:AT17 | F12:AT17 | F13:AT17 | F14:AT17 |
| F08:AT18 | F09:AT18 | F10:AT18 | F11:AT18 | F12:AT18 | F13:AT18 | F14:AT18 |
| F08:AT19 | F09:AT19 | F10:AT19 | F11:AT19 | F12:AT19 | F13:AT19 | F14:AT19 |
| F08:AT20 | F09:AT20 | F10:AT20 | F11:AT20 | F12:AT20 | F13:AT20 | F14:AT20 |
| F08:AT21 | F09:AT21 | F10:AT21 | F11:AT21 | F12:AT21 | F13:AT21 | F14:AT21 |
| F08:AT22 | F09:AT22 | F10:AT22 | F11:AT22 | F12:AT22 | F13:AT22 | F14:AT22 |
| F08:AT23 | F09:AT23 | F10:AT23 | F11:AT23 | F12:AT23 | F13:AT23 | F14:AT23 |
| F08:AT24 | F09:AT24 | F10:AT24 | F11:AT24 | F12:AT24 | F13:AT24 | F14:AT24 |
| F08:AT25 | F09:AT25 | F10:AT25 | F11:AT25 | F12:AT25 | F13:AT25 | F14:AT25 |
| F08:AT26 | F09:AT26 | F10:AT26 | F11:AT26 | F12:AT26 | F13:AT26 | F14:AT26 |
| F08:AT27 | F09:AT27 | F10:AT27 | F11:AT27 | F12:AT27 | F13:AT27 | F14:AT27 |
| F08:AT28 | F09:AT28 | F10:AT28 | F11:AT28 | F12:AT28 | F13:AT28 | F14:AT28 |
| F08:AT29 | F09:AT29 | F10:AT29 | F11:AT29 | F12:AT29 | F13:AT29 | F14:AT29 |
| F08:AT30 | F09:AT30 | F10:AT30 | F11:AT30 | F12:AT30 | F13:AT30 | F14:AT30 |
| F08:AT31 | F09:AT31 | F10:AT31 | F11:AT31 | F12:AT31 | F13:AT31 | F14:AT31 |
| F08:AT32 | F09:AT32 | F10:AT32 | F11:AT32 | F12:AT32 | F13:AT32 | F14:AT32 |
| F08:AT33 | F09:AT33 | F10:AT33 | F11:AT33 | F12:AT33 | F13:AT33 | F14:AT33 |
| F08:AT34 | F09:AT34 | F10:AT34 | F11:AT34 | F12:AT34 | F13:AT34 | F14:AT34 |
| F08:AT35 | F09:AT35 | F10:AT35 | F11:AT35 | F12:AT35 | F13:AT35 | F14:AT35 |
| F08:AT36 | F09:AT36 | F10:AT36 | F11:AT36 | F12:AT36 | F13:AT36 | F14:AT36 |
| F08:AT37 | F09:AT37 | F10:AT37 | F11:AT37 | F12:AT37 | F13:AT37 | F14:AT37 |
| F08:AT38 | F09:AT38 | F10:AT38 | F11:AT38 | F12:AT38 | F13:AT38 | F14:AT38 |
| F08:AT39 | F09:AT39 | F10:AT39 | F11:AT39 | F12:AT39 | F13:AT39 | F14:AT39 |
| F08:AT40 | F09:AT40 | F10:AT40 | F11:AT40 | F12:AT40 | F13:AT40 | F14:AT40 |
| F08:AT41 | F09:AT41 | F10:AT41 | F11:AT41 | F12:AT41 | F13:AT41 | F14:AT41 |
| F08:AT42 | F09:AT42 | F10:AT42 | F11:AT42 | F12:AT42 | F13:AT42 | F14:AT42 |
| F08:AT43 | F09:AT43 | F10:AT43 | F11:AT43 | F12:AT43 | F13:AT43 | F14:AT43 |
| F15:AT01 | F16:AT01 | F17:AT01 | F18:AT01 | F19:AT01 | F20:AT01 | F21:AT01 |
| F15:AT02 | F16:AT02 | F17:AT02 | F18:AT02 | F19:AT02 | F20:AT02 | F21:AT02 |
| F15:AT03 | F16:AT03 | F17:AT03 | F18:AT03 | F19:AT03 | F20:AT03 | F21:AT03 |
| F15:AT04 | F16:AT04 | F17:AT04 | F18:AT04 | F19:AT04 | F20:AT04 | F21:AT04 |
| F15:AT05 | F16:AT05 | F17:AT05 | F18:AT05 | F19:AT05 | F20:AT05 | F21:AT05 |
| F15:AT06 | F16:AT06 | F17:AT06 | F18:AT06 | F19:AT06 | F20:AT06 | F21:AT06 |
| F15:AT07 | F16:AT07 | F17:AT07 | F18:AT07 | F19:AT07 | F20:AT07 | F21:AT07 |
| F15:AT08 | F16:AT08 | F17:AT08 | F18:AT08 | F19:AT08 | F20:AT08 | F21:AT08 |
| F15:AT09 | F16:AT09 | F17:AT09 | F18:AT09 | F19:AT09 | F20:AT09 | F21:AT09 |
| F15:AT10 | F16:AT10 | F17:AT10 | F18:AT10 | F19:AT10 | F20:AT10 | F21:AT10 |
| F15:AT11 | F16:AT11 | F17:AT11 | F18:AT11 | F19:AT11 | F20:AT11 | F21:AT11 |
| F15:AT12 | F16:AT12 | F17:AT12 | F18:AT12 | F19:AT12 | F20:AT12 | F21:AT12 |
| F15:AT13 | F16:AT13 | F17:AT13 | F18:AT13 | F19:AT13 | F20:AT13 | F21:AT13 |
| F15:AT14 | F16:AT14 | F17:AT14 | F18:AT14 | F19:AT14 | F20:AT14 | F21:AT14 |
| F15:AT15 | F16:AT15 | F17:AT15 | F18:AT15 | F19:AT15 | F20:AT15 | F21:AT15 |
| F15:AT16 | F16:AT16 | F17:AT16 | F18:AT16 | F19:AT16 | F20:AT16 | F21:AT16 |
| F15:AT17 | F16:AT17 | F17:AT17 | F18:AT17 | F19:AT17 | F20:AT17 | F21:AT17 |
| F15:AT18 | F16:AT18 | F17:AT18 | F18:AT18 | F19:AT18 | F20:AT18 | F21:AT18 |
| F15:AT19 | F16:AT19 | F17:AT19 | F18:AT19 | F19:AT19 | F20:AT19 | F21:AT19 |
| F15:AT20 | F16:AT20 | F17:AT20 | F18:AT20 | F19:AT20 | F20:AT20 | F21:AT20 |
| F15:AT21 | F16:AT21 | F17:AT21 | F18:AT21 | F19:AT21 | F20:AT21 | F21:AT21 |
| F15:AT22 | F16:AT22 | F17:AT22 | F18:AT22 | F19:AT22 | F20:AT22 | F21:AT22 |
| F15:AT23 | F16:AT23 | F17:AT23 | F18:AT23 | F19:AT23 | F20:AT23 | F21:AT23 |
| F15:AT24 | F16:AT24 | F17:AT24 | F18:AT24 | F19:AT24 | F20:AT24 | F21:AT24 |
| F15:AT25 | F16:AT25 | F17:AT25 | F18:AT25 | F19:AT25 | F20:AT25 | F21:AT25 |
| F15:AT26 | F16:AT26 | F17:AT26 | F18:AT26 | F19:AT26 | F20:AT26 | F21:AT26 |
| F15:AT27 | F16:AT27 | F17:AT27 | F18:AT27 | F19:AT27 | F20:AT27 | F21:AT27 |
| F15:AT28 | F16:AT28 | F17:AT28 | F18:AT28 | F19:AT28 | F20:AT28 | F21:AT28 |
| F15:AT29 | F16:AT29 | F17:AT29 | F18:AT29 | F19:AT29 | F20:AT29 | F21:AT29 |
| F15:AT30 | F16:AT30 | F17:AT30 | F18:AT30 | F19:AT30 | F20:AT30 | F21:AT30 |
| F15:AT31 | F16:AT31 | F17:AT31 | F18:AT31 | F19:AT31 | F20:AT31 | F21:AT31 |
| F15:AT32 | F16:AT32 | F17:AT32 | F18:AT32 | F19:AT32 | F20:AT32 | F21:AT32 |
| F15:AT33 | F16:AT33 | F17:AT33 | F18:AT33 | F19:AT33 | F20:AT33 | F21:AT33 |
| F15:AT34 | F16:AT34 | F17:AT34 | F18:AT34 | F19:AT34 | F20:AT34 | F21:AT34 |

TABLE 2-continued

| X:Y | X:Y | X:Y | X:Y | X:Y | X:Y | X:Y |
|---|---|---|---|---|---|---|
| F15:AT35 | F16:AT35 | F17:AT35 | F18:AT35 | F19:AT35 | F20:AT35 | F21:AT35 |
| F15:AT36 | F16:AT36 | F17:AT36 | F18:AT36 | F19:AT36 | F20:AT36 | F21:AT36 |
| F15:AT37 | F16:AT37 | F17:AT37 | F18:AT37 | F19:AT37 | F20:AT37 | F21:AT37 |
| F15:AT38 | F16:AT38 | F17:AT38 | F18:AT38 | F19:AT38 | F20:AT38 | F21:AT38 |
| F15:AT39 | F16:AT39 | F17:AT39 | F18:AT39 | F19:AT39 | F20:AT39 | F21:AT39 |
| F15:AT40 | F16:AT40 | F17:AT40 | F18:AT40 | F19:AT40 | F20:AT40 | F21:AT40 |
| F15:AT41 | F16:AT41 | F17:AT41 | F18:AT41 | F19:AT41 | F20:AT41 | F21:AT41 |
| F15:AT42 | F16:AT42 | F17:AT42 | F18:AT42 | F19:AT42 | F20:AT42 | F21:AT42 |
| F15:AT43 | F16:AT43 | F17:AT43 | F18:AT43 | F19:AT43 | F20:AT43 | F21:AT43 |
| F22:AT01 | F23:AT01 | F24:AT01 | F25:AT01 | F26:AT01 | F27:AT01 | F28:AT01 |
| F22:AT02 | F23:AT02 | F24:AT02 | F25:AT02 | F26:AT02 | F27:AT02 | F28:AT02 |
| F22:AT03 | F23:AT03 | F24:AT03 | F25:AT03 | F26:AT03 | F27:AT03 | F28:AT03 |
| F22:AT04 | F23:AT04 | F24:AT04 | F25:AT04 | F26:AT04 | F27:AT04 | F28:AT04 |
| F22:AT05 | F23:AT05 | F24:AT05 | F25:AT05 | F26:AT05 | F27:AT05 | F28:AT05 |
| F22:AT06 | F23:AT06 | F24:AT06 | F25:AT06 | F26:AT06 | F27:AT06 | F28:AT06 |
| F22:AT07 | F23:AT07 | F24:AT07 | F25:AT07 | F26:AT07 | F27:AT07 | F28:AT07 |
| F22:AT08 | F23:AT08 | F24:AT08 | F25:AT08 | F26:AT08 | F27:AT08 | F28:AT08 |
| F22:AT09 | F23:AT09 | F24:AT09 | F25:AT09 | F26:AT09 | F27:AT09 | F28:AT09 |
| F22:AT10 | F23:AT10 | F24:AT10 | F25:AT10 | F26:AT10 | F27:AT10 | F28:AT10 |
| F22:AT11 | F23:AT11 | F24:AT11 | F25:AT11 | F26:AT11 | F27:AT11 | F28:AT11 |
| F22:AT12 | F23:AT12 | F24:AT12 | F25:AT12 | F26:AT12 | F27:AT12 | F28:AT12 |
| F22:AT13 | F23:AT13 | F24:AT13 | F25:AT13 | F26:AT13 | F27:AT13 | F28:AT13 |
| F22:AT14 | F23:AT14 | F24:AT14 | F25:AT14 | F26:AT14 | F27:AT14 | F28:AT14 |
| F22:AT15 | F23:AT15 | F24:AT15 | F25:AT15 | F26:AT15 | F27:AT15 | F28:AT15 |
| F22:AT16 | F23:AT16 | F24:AT16 | F25:AT16 | F26:AT16 | F27:AT16 | F28:AT16 |
| F22:AT17 | F23:AT17 | F24:AT17 | F25:AT17 | F26:AT17 | F27:AT17 | F28:AT17 |
| F22:AT18 | F23:AT18 | F24:AT18 | F25:AT18 | F26:AT18 | F27:AT18 | F28:AT18 |
| F22:AT19 | F23:AT19 | F24:AT19 | F25:AT19 | F26:AT19 | F27:AT19 | F28:AT19 |
| F22:AT20 | F23:AT20 | F24:AT20 | F25:AT20 | F26:AT20 | F27:AT20 | F28:AT20 |
| F22:AT21 | F23:AT21 | F24:AT21 | F25:AT21 | F26:AT21 | F27:AT21 | F28:AT21 |
| F22:AT22 | F23:AT22 | F24:AT22 | F25:AT22 | F26:AT22 | F27:AT22 | F28:AT22 |
| F22:AT23 | F23:AT23 | F24:AT23 | F25:AT23 | F26:AT23 | F27:AT23 | F28:AT23 |
| F22:AT24 | F23:AT24 | F24:AT24 | F25:AT24 | F26:AT24 | F27:AT24 | F28:AT24 |
| F22:AT25 | F23:AT25 | F24:AT25 | F25:AT25 | F26:AT25 | F27:AT25 | F28:AT25 |
| F22:AT26 | F23:AT26 | F24:AT26 | F25:AT26 | F26:AT26 | F27:AT26 | F28:AT26 |
| F22:AT27 | F23:AT27 | F24:AT27 | F25:AT27 | F26:AT27 | F27:AT27 | F28:AT27 |
| F22:AT28 | F23:AT28 | F24:AT28 | F25:AT28 | F26:AT28 | F27:AT28 | F28:AT28 |
| F22:AT29 | F23:AT29 | F24:AT29 | F25:AT29 | F26:AT29 | F27:AT29 | F28:AT29 |
| F22:AT30 | F23:AT30 | F24:AT30 | F25:AT30 | F26:AT30 | F27:AT30 | F28:AT30 |
| F22:AT31 | F23:AT31 | F24:AT31 | F25:AT31 | F26:AT31 | F27:AT31 | F28:AT31 |
| F22:AT32 | F23:AT32 | F24:AT32 | F25:AT32 | F26:AT32 | F27:AT32 | F28:AT32 |
| F22:AT33 | F23:AT33 | F24:AT33 | F25:AT33 | F26:AT33 | F27:AT33 | F28:AT33 |
| F22:AT34 | F23:AT34 | F24:AT34 | F25:AT34 | F26:AT34 | F27:AT34 | F28:AT34 |
| F22:AT35 | F23:AT35 | F24:AT35 | F25:AT35 | F26:AT35 | F27:AT35 | F28:AT35 |
| F22:AT36 | F23:AT36 | F24:AT36 | F25:AT36 | F26:AT36 | F27:AT36 | F28:AT36 |
| F22:AT37 | F23:AT37 | F24:AT37 | F25:AT37 | F26:AT37 | F27:AT37 | F28:AT37 |
| F22:AT38 | F23:AT38 | F24:AT38 | F25:AT38 | F26:AT38 | F27:AT38 | F28:AT38 |
| F22:AT39 | F23:AT39 | F24:AT39 | F25:AT39 | F26:AT39 | F27:AT39 | F28:AT39 |
| F22:AT40 | F23:AT40 | F24:AT40 | F25:AT40 | F26:AT40 | F27:AT40 | F28:AT40 |
| F22:AT41 | F23:AT41 | F24:AT41 | F25:AT41 | F26:AT41 | F27:AT41 | F28:AT41 |
| F22:AT42 | F23:AT42 | F24:AT42 | F25:AT42 | F26:AT42 | F27:AT42 | F28:AT42 |
| F22:AT43 | F23:AT43 | F24:AT43 | F25:AT43 | F26:AT43 | F27:AT43 | F28:AT43 |
| F29:AT01 | F30:AT01 | F31:AT01 | F32:AT01 | F33:AT01 | F34:AT01 | F35:AT01 |
| F29:AT02 | F30:AT02 | F31:AT02 | F32:AT02 | F33:AT02 | F34:AT02 | F35:AT02 |
| F29:AT03 | F30:AT03 | F31:AT03 | F32:AT03 | F33:AT03 | F34:AT03 | F35:AT03 |
| F29:AT04 | F30:AT04 | F31:AT04 | F32:AT04 | F33:AT04 | F34:AT04 | F35:AT04 |
| F29:AT05 | F30:AT05 | F31:AT05 | F32:AT05 | F33:AT05 | F34:AT05 | F35:AT05 |
| F29:AT06 | F30:AT06 | F31:AT06 | F32:AT06 | F33:AT06 | F34:AT06 | F35:AT06 |
| F29:AT07 | F30:AT07 | F31:AT07 | F32:AT07 | F33:AT07 | F34:AT07 | F35:AT07 |
| F29:AT08 | F30:AT08 | F31:AT08 | F32:AT08 | F33:AT08 | F34:AT08 | F35:AT08 |
| F29:AT09 | F30:AT09 | F31:AT09 | F32:AT09 | F33:AT09 | F34:AT09 | F35:AT09 |
| F29:AT10 | F30:AT10 | F31:AT10 | F32:AT10 | F33:AT10 | F34:AT10 | F35:AT10 |
| F29:AT11 | F30:AT11 | F31:AT11 | F32:AT11 | F33:AT11 | F34:AT11 | F35:AT11 |
| F29:AT12 | F30:AT12 | F31:AT12 | F32:AT12 | F33:AT12 | F34:AT12 | F35:AT12 |
| F29:AT13 | F30:AT13 | F31:AT13 | F32:AT13 | F33:AT13 | F34:AT13 | F35:AT13 |
| F29:AT14 | F30:AT14 | F31:AT14 | F32:AT14 | F33:AT14 | F34:AT14 | F35:AT14 |
| F29:AT15 | F30:AT15 | F31:AT15 | F32:AT15 | F33:AT15 | F34:AT15 | F35:AT15 |
| F29:AT16 | F30:AT16 | F31:AT16 | F32:AT16 | F33:AT16 | F34:AT16 | F35:AT16 |
| F29:AT17 | F30:AT17 | F31:AT17 | F32:AT17 | F33:AT17 | F34:AT17 | F35:AT17 |
| F29:AT18 | F30:AT18 | F31:AT18 | F32:AT18 | F33:AT18 | F34:AT18 | F35:AT18 |
| F29:AT19 | F30:AT19 | F31:AT19 | F32:AT19 | F33:AT19 | F34:AT19 | F35:AT19 |
| F29:AT20 | F30:AT20 | F31:AT20 | F32:AT20 | F33:AT20 | F34:AT20 | F35:AT20 |
| F29:AT21 | F30:AT21 | F31:AT21 | F32:AT21 | F33:AT21 | F34:AT21 | F35:AT21 |
| F29:AT22 | F30:AT22 | F31:AT22 | F32:AT22 | F33:AT22 | F34:AT22 | F35:AT22 |
| F29:AT23 | F30:AT23 | F31:AT23 | F32:AT23 | F33:AT23 | F34:AT23 | F35:AT23 |
| F29:AT24 | F30:AT24 | F31:AT24 | F32:AT24 | F33:AT24 | F34:AT24 | F35:AT24 |
| F29:AT25 | F30:AT25 | F31:AT25 | F32:AT25 | F33:AT25 | F34:AT25 | F35:AT25 |
| F29:AT26 | F30:AT26 | F31:AT26 | F32:AT26 | F33:AT26 | F34:AT26 | F35:AT26 |

TABLE 2-continued

| X:Y | X:Y | X:Y | X:Y | X:Y | X:Y | X:Y |
|---|---|---|---|---|---|---|
| F29:AT27 | F30:AT27 | F31:AT27 | F32:AT27 | F33:AT27 | F34:AT27 | F35:AT27 |
| F29:AT28 | F30:AT28 | F31:AT28 | F32:AT28 | F33:AT28 | F34:AT28 | F35:AT28 |
| F29:AT29 | F30:AT29 | F31:AT29 | F32:AT29 | F33:AT29 | F34:AT29 | F35:AT29 |
| F29:AT30 | F30:AT30 | F31:AT30 | F32:AT30 | F33:AT30 | F34:AT30 | F35:AT30 |
| F29:AT31 | F30:AT31 | F31:AT31 | F32:AT31 | F33:AT31 | F34:AT31 | F35:AT31 |
| F29:AT32 | F30:AT32 | F31:AT32 | F32:AT32 | F33:AT32 | F34:AT32 | F35:AT32 |
| F29:AT33 | F30:AT33 | F31:AT33 | F32:AT33 | F33:AT33 | F34:AT33 | F35:AT33 |
| F29:AT34 | F30:AT34 | F31:AT34 | F32:AT34 | F33:AT34 | F34:AT34 | F35:AT34 |
| F29:AT35 | F30:AT35 | F31:AT35 | F32:AT35 | F33:AT35 | F34:AT35 | F35:AT35 |
| F29:AT36 | F30:AT36 | F31:AT36 | F32:AT36 | F33:AT36 | F34:AT36 | F35:AT36 |
| F29:AT37 | F30:AT37 | F31:AT37 | F32:AT37 | F33:AT37 | F34:AT37 | F35:AT37 |
| F29:AT38 | F30:AT38 | F31:AT38 | F32:AT38 | F33:AT38 | F34:AT38 | F35:AT38 |
| F29:AT39 | F30:AT39 | F31:AT39 | F32:AT39 | F33:AT39 | F34:AT39 | F35:AT39 |
| F29:AT40 | F30:AT40 | F31:AT40 | F32:AT40 | F33:AT40 | F34:AT40 | F35:AT40 |
| F29:AT41 | F30:AT41 | F31:AT41 | F32:AT41 | F33:AT41 | F34:AT41 | F35:AT41 |
| F29:AT42 | F30:AT42 | F31:AT42 | F32:AT42 | F33:AT42 | F34:AT42 | F35:AT42 |
| F29:AT43 | F30:AT43 | F31:AT43 | F32:AT43 | F33:AT43 | F34:AT43 | F35:AT43 |
| F36:AT01 | F37:AT01 | F38:AT01 | F39:AT01 | F40:AT01 | F41:AT01 | F42:AT01 |
| F36:AT02 | F37:AT02 | F38:AT02 | F39:AT02 | F40:AT02 | F41:AT02 | F42:AT02 |
| F36:AT03 | F37:AT03 | F38:AT03 | F39:AT03 | F40:AT03 | F41:AT03 | F42:AT03 |
| F36:AT04 | F37:AT04 | F38:AT04 | F39:AT04 | F40:AT04 | F41:AT04 | F42:AT04 |
| F36:AT05 | F37:AT05 | F38:AT05 | F39:AT05 | F40:AT05 | F41:AT05 | F42:AT05 |
| F36:AT06 | F37:AT06 | F38:AT06 | F39:AT06 | F40:AT06 | F41:AT06 | F42:AT06 |
| F36:AT07 | F37:AT07 | F38:AT07 | F39:AT07 | F40:AT07 | F41:AT07 | F42:AT07 |
| F36:AT08 | F37:AT08 | F38:AT08 | F39:AT08 | F40:AT08 | F41:AT08 | F42:AT08 |
| F36:AT09 | F37:AT09 | F38:AT09 | F39:AT09 | F40:AT09 | F41:AT09 | F42:AT09 |
| F36:AT10 | F37:AT10 | F38:AT10 | F39:AT10 | F40:AT10 | F41:AT10 | F42:AT10 |
| F36:AT11 | F37:AT11 | F38:AT11 | F39:AT11 | F40:AT11 | F41:AT11 | F42:AT11 |
| F36:AT12 | F37:AT12 | F38:AT12 | F39:AT12 | F40:AT12 | F41:AT12 | F42:AT12 |
| F36:AT13 | F37:AT13 | F38:AT13 | F39:AT13 | F40:AT13 | F41:AT13 | F42:AT13 |
| F36:AT14 | F37:AT14 | F38:AT14 | F39:AT14 | F40:AT14 | F41:AT14 | F42:AT14 |
| F36:AT15 | F37:AT15 | F38:AT15 | F39:AT15 | F40:AT15 | F41:AT15 | F42:AT15 |
| F36:AT16 | F37:AT16 | F38:AT16 | F39:AT16 | F40:AT16 | F41:AT16 | F42:AT16 |
| F36:AT17 | F37:AT17 | F38:AT17 | F39:AT17 | F40:AT17 | F41:AT17 | F42:AT17 |
| F36:AT18 | F37:AT18 | F38:AT18 | F39:AT18 | F40:AT18 | F41:AT18 | F42:AT18 |
| F36:AT19 | F37:AT19 | F38:AT19 | F39:AT19 | F40:AT19 | F41:AT19 | F42:AT19 |
| F36:AT20 | F37:AT20 | F38:AT20 | F39:AT20 | F40:AT20 | F41:AT20 | F42:AT20 |
| F36:AT21 | F37:AT21 | F38:AT21 | F39:AT21 | F40:AT21 | F41:AT21 | F42:AT21 |
| F36:AT22 | F37:AT22 | F38:AT22 | F39:AT22 | F40:AT22 | F41:AT22 | F42:AT22 |
| F36:AT23 | F37:AT23 | F38:AT23 | F39:AT23 | F40:AT23 | F41:AT23 | F42:AT23 |
| F36:AT24 | F37:AT24 | F38:AT24 | F39:AT24 | F40:AT24 | F41:AT24 | F42:AT24 |
| F36:AT25 | F37:AT25 | F38:AT25 | F39:AT25 | F40:AT25 | F41:AT25 | F42:AT25 |
| F36:AT26 | F37:AT26 | F38:AT26 | F39:AT26 | F40:AT26 | F41:AT26 | F42:AT26 |
| F36:AT27 | F37:AT27 | F38:AT27 | F39:AT27 | F40:AT27 | F41:AT27 | F42:AT27 |
| F36:AT28 | F37:AT28 | F38:AT28 | F39:AT28 | F40:AT28 | F41:AT28 | F42:AT28 |
| F36:AT29 | F37:AT29 | F38:AT29 | F39:AT29 | F40:AT29 | F41:AT29 | F42:AT29 |
| F36:AT30 | F37:AT30 | F38:AT30 | F39:AT30 | F40:AT30 | F41:AT30 | F42:AT30 |
| F36:AT31 | F37:AT31 | F38:AT31 | F39:AT31 | F40:AT31 | F41:AT31 | F42:AT31 |
| F36:AT32 | F37:AT32 | F38:AT32 | F39:AT32 | F40:AT32 | F41:AT32 | F42:AT32 |
| F36:AT33 | F37:AT33 | F38:AT33 | F39:AT33 | F40:AT33 | F41:AT33 | F42:AT33 |
| F36:AT34 | F37:AT34 | F38:AT34 | F39:AT34 | F40:AT34 | F41:AT34 | F42:AT34 |
| F36:AT35 | F37:AT35 | F38:AT35 | F39:AT35 | F40:AT35 | F41:AT35 | F42:AT35 |
| F36:AT36 | F37:AT36 | F38:AT36 | F39:AT36 | F40:AT36 | F41:AT36 | F42:AT36 |
| F36:AT37 | F37:AT37 | F38:AT37 | F39:AT37 | F40:AT37 | F41:AT37 | F42:AT37 |
| F36:AT38 | F37:AT38 | F38:AT38 | F39:AT38 | F40:AT38 | F41:AT38 | F42:AT38 |
| F36:AT39 | F37:AT39 | F38:AT39 | F39:AT39 | F40:AT39 | F41:AT39 | F42:AT39 |
| F36:AT40 | F37:AT40 | F38:AT40 | F39:AT40 | F40:AT40 | F41:AT40 | F42:AT40 |
| F36:AT41 | F37:AT41 | F38:AT41 | F39:AT41 | F40:AT41 | F41:AT41 | F42:AT41 |
| F36:AT42 | F37:AT42 | F38:AT42 | F39:AT42 | F40:AT42 | F41:AT42 | F42:AT42 |
| F36:AT43 | F37:AT43 | F38:AT43 | F39:AT43 | F40:AT43 | F41:AT43 | F42:AT43 |
| F43:AT01 | F44:AT01 | F45:AT01 | F46:AT01 | F47:AT01 | F48:AT01 | F49:AT01 |
| F43:AT02 | F44:AT02 | F45:AT02 | F46:AT02 | F47:AT02 | F48:AT02 | F49:AT02 |
| F43:AT03 | F44:AT03 | F45:AT03 | F46:AT03 | F47:AT03 | F48:AT03 | F49:AT03 |
| F43:AT04 | F44:AT04 | F45:AT04 | F46:AT04 | F47:AT04 | F48:AT04 | F49:AT04 |
| F43:AT05 | F44:AT05 | F45:AT05 | F46:AT05 | F47:AT05 | F48:AT05 | F49:AT05 |
| F43:AT06 | F44:AT06 | F45:AT06 | F46:AT06 | F47:AT06 | F48:AT06 | F49:AT06 |
| F43:AT07 | F44:AT07 | F45:AT07 | F46:AT07 | F47:AT07 | F48:AT07 | F49:AT07 |
| F43:AT08 | F44:AT08 | F45:AT08 | F46:AT08 | F47:AT08 | F48:AT08 | F49:AT08 |
| F43:AT09 | F44:AT09 | F45:AT09 | F46:AT09 | F47:AT09 | F48:AT09 | F49:AT09 |
| F43:AT10 | F44:AT10 | F45:AT10 | F46:AT10 | F47:AT10 | F48:AT10 | F49:AT10 |
| F43:AT11 | F44:AT11 | F45:AT11 | F46:AT11 | F47:AT11 | F48:AT11 | F49:AT11 |
| F43:AT12 | F44:AT12 | F45:AT12 | F46:AT12 | F47:AT12 | F48:AT12 | F49:AT12 |
| F43:AT13 | F44:AT13 | F45:AT13 | F46:AT13 | F47:AT13 | F48:AT13 | F49:AT13 |
| F43:AT14 | F44:AT14 | F45:AT14 | F46:AT14 | F47:AT14 | F48:AT14 | F49:AT14 |
| F43:AT15 | F44:AT15 | F45:AT15 | F46:AT15 | F47:AT15 | F48:AT15 | F49:AT15 |
| F43:AT16 | F44:AT16 | F45:AT16 | F46:AT16 | F47:AT16 | F48:AT16 | F49:AT16 |
| F43:AT17 | F44:AT17 | F45:AT17 | F46:AT17 | F47:AT17 | F48:AT17 | F49:AT17 |
| F43:AT18 | F44:AT18 | F45:AT18 | F46:AT18 | F47:AT18 | F48:AT18 | F49:AT18 |

TABLE 2-continued

| X:Y | X:Y | X:Y | X:Y | X:Y | X:Y | X:Y |
|---|---|---|---|---|---|---|
| F43:AT19 | F44:AT19 | F45:AT19 | F46:AT19 | F47:AT19 | F48:AT19 | F49:AT19 |
| F43:AT20 | F44:AT20 | F45:AT20 | F46:AT20 | F47:AT20 | F48:AT20 | F49:AT20 |
| F43:AT21 | F44:AT21 | F45:AT21 | F46:AT21 | F47:AT21 | F48:AT21 | F49:AT21 |
| F43:AT22 | F44:AT22 | F45:AT22 | F46:AT22 | F47:AT22 | F48:AT22 | F49:AT22 |
| F43:AT23 | F44:AT23 | F45:AT23 | F46:AT23 | F47:AT23 | F48:AT23 | F49:AT23 |
| F43:AT24 | F44:AT24 | F45:AT24 | F46:AT24 | F47:AT24 | F48:AT24 | F49:AT24 |
| F43:AT25 | F44:AT25 | F45:AT25 | F46:AT25 | F47:AT25 | F48:AT25 | F49:AT25 |
| F43:AT26 | F44:AT26 | F45:AT26 | F46:AT26 | F47:AT26 | F48:AT26 | F49:AT26 |
| F43:AT27 | F44:AT27 | F45:AT27 | F46:AT27 | F47:AT27 | F48:AT27 | F49:AT27 |
| F43:AT28 | F44:AT28 | F45:AT28 | F46:AT28 | F47:AT28 | F48:AT28 | F49:AT28 |
| F43:AT29 | F44:AT29 | F45:AT29 | F46:AT29 | F47:AT29 | F48:AT29 | F49:AT29 |
| F43:AT30 | F44:AT30 | F45:AT30 | F46:AT30 | F47:AT30 | F48:AT30 | F49:AT30 |
| F43:AT31 | F44:AT31 | F45:AT31 | F46:AT31 | F47:AT31 | F48:AT31 | F49:AT31 |
| F43:AT32 | F44:AT32 | F45:AT32 | F46:AT32 | F47:AT32 | F48:AT32 | F49:AT32 |
| F43:AT33 | F44:AT33 | F45:AT33 | F46:AT33 | F47:AT33 | F48:AT33 | F49:AT33 |
| F43:AT34 | F44:AT34 | F45:AT34 | F46:AT34 | F47:AT34 | F48:AT34 | F49:AT34 |
| F43:AT35 | F44:AT35 | F45:AT35 | F46:AT35 | F47:AT35 | F48:AT35 | F49:AT35 |
| F43:AT36 | F44:AT36 | F45:AT36 | F46:AT36 | F47:AT36 | F48:AT36 | F49:AT36 |
| F43:AT37 | F44:AT37 | F45:AT37 | F46:AT37 | F47:AT37 | F48:AT37 | F49:AT37 |
| F43:AT38 | F44:AT38 | F45:AT38 | F46:AT38 | F47:AT38 | F48:AT38 | F49:AT38 |
| F43:AT39 | F44:AT39 | F45:AT39 | F46:AT39 | F47:AT39 | F48:AT39 | F49:AT39 |
| F43:AT40 | F44:AT40 | F45:AT40 | F46:AT40 | F47:AT40 | F48:AT40 | F49:AT40 |
| F43:AT41 | F44:AT41 | F45:AT41 | F46:AT41 | F47:AT41 | F48:AT41 | F49:AT41 |
| F43:AT42 | F44:AT42 | F45:AT42 | F46:AT42 | F47:AT42 | F48:AT42 | F49:AT42 |
| F43:AT43 | F44:AT43 | F45:AT43 | F46:AT43 | F47:AT43 | F48:AT43 | F49:AT43 |
| F50:AT01 | F51:AT01 | F52:AT01 | F53:AT01 | F54:AT01 | F55:AT01 | F56:AT01 |
| F50:AT02 | F51:AT02 | F52:AT02 | F53:AT02 | F54:AT02 | F55:AT02 | F56:AT02 |
| F50:AT03 | F51:AT03 | F52:AT03 | F53:AT03 | F54:AT03 | F55:AT03 | F56:AT03 |
| F50:AT04 | F51:AT04 | F52:AT04 | F53:AT04 | F54:AT04 | F55:AT04 | F56:AT04 |
| F50:AT05 | F51:AT05 | F52:AT05 | F53:AT05 | F54:AT05 | F55:AT05 | F56:AT05 |
| F50:AT06 | F51:AT06 | F52:AT06 | F53:AT06 | F54:AT06 | F55:AT06 | F56:AT06 |
| F50:AT07 | F51:AT07 | F52:AT07 | F53:AT07 | F54:AT07 | F55:AT07 | F56:AT07 |
| F50:AT08 | F51:AT08 | F52:AT08 | F53:AT08 | F54:AT08 | F55:AT08 | F56:AT08 |
| F50:AT09 | F51:AT09 | F52:AT09 | F53:AT09 | F54:AT09 | F55:AT09 | F56:AT09 |
| F50:AT10 | F51:AT10 | F52:AT10 | F53:AT10 | F54:AT10 | F55:AT10 | F56:AT10 |
| F50:AT11 | F51:AT11 | F52:AT11 | F53:AT11 | F54:AT11 | F55:AT11 | F56:AT11 |
| F50:AT12 | F51:AT12 | F52:AT12 | F53:AT12 | F54:AT12 | F55:AT12 | F56:AT12 |
| F50:AT13 | F51:AT13 | F52:AT13 | F53:AT13 | F54:AT13 | F55:AT13 | F56:AT13 |
| F50:AT14 | F51:AT14 | F52:AT14 | F53:AT14 | F54:AT14 | F55:AT14 | F56:AT14 |
| F50:AT15 | F51:AT15 | F52:AT15 | F53:AT15 | F54:AT15 | F55:AT15 | F56:AT15 |
| F50:AT16 | F51:AT16 | F52:AT16 | F53:AT16 | F54:AT16 | F55:AT16 | F56:AT16 |
| F50:AT17 | F51:AT17 | F52:AT17 | F53:AT17 | F54:AT17 | F55:AT17 | F56:AT17 |
| F50:AT18 | F51:AT18 | F52:AT18 | F53:AT18 | F54:AT18 | F55:AT18 | F56:AT18 |
| F50:AT19 | F51:AT19 | F52:AT19 | F53:AT19 | F54:AT19 | F55:AT19 | F56:AT19 |
| F50:AT20 | F51:AT20 | F52:AT20 | F53:AT20 | F54:AT20 | F55:AT20 | F56:AT20 |
| F50:AT21 | F51:AT21 | F52:AT21 | F53:AT21 | F54:AT21 | F55:AT21 | F56:AT21 |
| F50:AT22 | F51:AT22 | F52:AT22 | F53:AT22 | F54:AT22 | F55:AT22 | F56:AT22 |
| F50:AT23 | F51:AT23 | F52:AT23 | F53:AT23 | F54:AT23 | F55:AT23 | F56:AT23 |
| F50:AT24 | F51:AT24 | F52:AT24 | F53:AT24 | F54:AT24 | F55:AT24 | F56:AT24 |
| F50:AT25 | F51:AT25 | F52:AT25 | F53:AT25 | F54:AT25 | F55:AT25 | F56:AT25 |
| F50:AT26 | F51:AT26 | F52:AT26 | F53:AT26 | F54:AT26 | F55:AT26 | F56:AT26 |
| F50:AT27 | F51:AT27 | F52:AT27 | F53:AT27 | F54:AT27 | F55:AT27 | F56:AT27 |
| F50:AT28 | F51:AT28 | F52:AT28 | F53:AT28 | F54:AT28 | F55:AT28 | F56:AT28 |
| F50:AT29 | F51:AT29 | F52:AT29 | F53:AT29 | F54:AT29 | F55:AT29 | F56:AT29 |
| F50:AT30 | F51:AT30 | F52:AT30 | F53:AT30 | F54:AT30 | F55:AT30 | F56:AT30 |
| F50:AT31 | F51:AT31 | F52:AT31 | F53:AT31 | F54:AT31 | F55:AT31 | F56:AT31 |
| F50:AT32 | F51:AT32 | F52:AT32 | F53:AT32 | F54:AT32 | F55:AT32 | F56:AT32 |
| F50:AT33 | F51:AT33 | F52:AT33 | F53:AT33 | F54:AT33 | F55:AT33 | F56:AT33 |
| F50:AT34 | F51:AT34 | F52:AT34 | F53:AT34 | F54:AT34 | F55:AT34 | F56:AT34 |
| F50:AT35 | F51:AT35 | F52:AT35 | F53:AT35 | F54:AT35 | F55:AT35 | F56:AT35 |
| F50:AT36 | F51:AT36 | F52:AT36 | F53:AT36 | F54:AT36 | F55:AT36 | F56:AT36 |
| F50:AT37 | F51:AT37 | F52:AT37 | F53:AT37 | F54:AT37 | F55:AT37 | F56:AT37 |
| F50:AT38 | F51:AT38 | F52:AT38 | F53:AT38 | F54:AT38 | F55:AT38 | F56:AT38 |
| F50:AT39 | F51:AT39 | F52:AT39 | F53:AT39 | F54:AT39 | F55:AT39 | F56:AT39 |
| F50:AT40 | F51:AT40 | F52:AT40 | F53:AT40 | F54:AT40 | F55:AT40 | F56:AT40 |
| F50:AT41 | F51:AT41 | F52:AT41 | F53:AT41 | F54:AT41 | F55:AT41 | F56:AT41 |
| F50:AT42 | F51:AT42 | F52:AT42 | F53:AT42 | F54:AT42 | F55:AT42 | F56:AT42 |
| F50:AT43 | F51:AT43 | F52:AT43 | F53:AT43 | F54:AT43 | F55:AT43 | F56:AT43 |
| F57:AT01 | F58:AT01 | F59:AT01 | F60:AT01 | F61:AT01 | F62:AT01 | F63:AT01 |
| F57:AT02 | F58:AT02 | F59:AT02 | F60:AT02 | F61:AT02 | F62:AT02 | F63:AT02 |
| F57:AT03 | F58:AT03 | F59:AT03 | F60:AT03 | F61:AT03 | F62:AT03 | F63:AT03 |
| F57:AT04 | F58:AT04 | F59:AT04 | F60:AT04 | F61:AT04 | F62:AT04 | F63:AT04 |
| F57:AT05 | F58:AT05 | F59:AT05 | F60:AT05 | F61:AT05 | F62:AT05 | F63:AT05 |
| F57:AT06 | F58:AT06 | F59:AT06 | F60:AT06 | F61:AT06 | F62:AT06 | F63:AT06 |
| F57:AT07 | F58:AT07 | F59:AT07 | F60:AT07 | F61:AT07 | F62:AT07 | F63:AT07 |
| F57:AT08 | F58:AT08 | F59:AT08 | F60:AT08 | F61:AT08 | F62:AT08 | F63:AT08 |
| F57:AT09 | F58:AT09 | F59:AT09 | F60:AT09 | F61:AT09 | F62:AT09 | F63:AT09 |
| F57:AT10 | F58:AT10 | F59:AT10 | F60:AT10 | F61:AT10 | F62:AT10 | F63:AT10 |

TABLE 2-continued

| X:Y | X:Y | X:Y | X:Y | X:Y | X:Y | X:Y |
|---|---|---|---|---|---|---|
| F57:AT11 | F58:AT11 | F59:AT11 | F60:AT11 | F61:AT11 | F62:AT11 | F63:AT11 |
| F57:AT12 | F58:AT12 | F59:AT12 | F60:AT12 | F61:AT12 | F62:AT12 | F63:AT12 |
| F57:AT13 | F58:AT13 | F59:AT13 | F60:AT13 | F61:AT13 | F62:AT13 | F63:AT13 |
| F57:AT14 | F58:AT14 | F59:AT14 | F60:AT14 | F61:AT14 | F62:AT14 | F63:AT14 |
| F57:AT15 | F58:AT15 | F59:AT15 | F60:AT15 | F61:AT15 | F62:AT15 | F63:AT15 |
| F57:AT16 | F58:AT16 | F59:AT16 | F60:AT16 | F61:AT16 | F62:AT16 | F63:AT16 |
| F57:AT17 | F58:AT17 | F59:AT17 | F60:AT17 | F61:AT17 | F62:AT17 | F63:AT17 |
| F57:AT18 | F58:AT18 | F59:AT18 | F60:AT18 | F61:AT18 | F62:AT18 | F63:AT18 |
| F57:AT19 | F58:AT19 | F59:AT19 | F60:AT19 | F61:AT19 | F62:AT19 | F63:AT19 |
| F57:AT20 | F58:AT20 | F59:AT20 | F60:AT20 | F61:AT20 | F62:AT20 | F63:AT20 |
| F57:AT21 | F58:AT21 | F59:AT21 | F60:AT21 | F61:AT21 | F62:AT21 | F63:AT21 |
| F57:AT22 | F58:AT22 | F59:AT22 | F60:AT22 | F61:AT22 | F62:AT22 | F63:AT22 |
| F57:AT23 | F58:AT23 | F59:AT23 | F60:AT23 | F61:AT23 | F62:AT23 | F63:AT23 |
| F57:AT24 | F58:AT24 | F59:AT24 | F60:AT24 | F61:AT24 | F62:AT24 | F63:AT24 |
| F57:AT25 | F58:AT25 | F59:AT25 | F60:AT25 | F61:AT25 | F62:AT25 | F63:AT25 |
| F57:AT26 | F58:AT26 | F59:AT26 | F60:AT26 | F61:AT26 | F62:AT26 | F63:AT26 |
| F57:AT27 | F58:AT27 | F59:AT27 | F60:AT27 | F61:AT27 | F62:AT27 | F63:AT27 |
| F57:AT28 | F58:AT28 | F59:AT28 | F60:AT28 | F61:AT28 | F62:AT28 | F63:AT28 |
| F57:AT29 | F58:AT29 | F59:AT29 | F60:AT29 | F61:AT29 | F62:AT29 | F63:AT29 |
| F57:AT30 | F58:AT30 | F59:AT30 | F60:AT30 | F61:AT30 | F62:AT30 | F63:AT30 |
| F57:AT31 | F58:AT31 | F59:AT31 | F60:AT31 | F61:AT31 | F62:AT31 | F63:AT31 |
| F57:AT32 | F58:AT32 | F59:AT32 | F60:AT32 | F61:AT32 | F62:AT32 | F63:AT32 |
| F57:AT33 | F58:AT33 | F59:AT33 | F60:AT33 | F61:AT33 | F62:AT33 | F63:AT33 |
| F57:AT34 | F58:AT34 | F59:AT34 | F60:AT34 | F61:AT34 | F62:AT34 | F63:AT34 |
| F57:AT35 | F58:AT35 | F59:AT35 | F60:AT35 | F61:AT35 | F62:AT35 | F63:AT35 |
| F57:AT36 | F58:AT36 | F59:AT36 | F60:AT36 | F61:AT36 | F62:AT36 | F63:AT36 |
| F57:AT37 | F58:AT37 | F59:AT37 | F60:AT37 | F61:AT37 | F62:AT37 | F63:AT37 |
| F57:AT38 | F58:AT38 | F59:AT38 | F60:AT38 | F61:AT38 | F62:AT38 | F63:AT38 |
| F57:AT39 | F58:AT39 | F59:AT39 | F60:AT39 | F61:AT39 | F62:AT39 | F63:AT39 |
| F57:AT40 | F58:AT40 | F59:AT40 | F60:AT40 | F61:AT40 | F62:AT40 | F63:AT40 |
| F57:AT41 | F58:AT41 | F59:AT41 | F60:AT41 | F61:AT41 | F62:AT41 | F63:AT41 |
| F57:AT42 | F58:AT42 | F59:AT42 | F60:AT42 | F61:AT42 | F62:AT42 | F63:AT42 |
| F57:AT43 | F58:AT43 | F59:AT43 | F60:AT43 | F61:AT43 | F62:AT43 | F63:AT43 |

The order of administration of a compound disclosed herein (such as a compound of Formula (I), (II), (III), or (IV)), or a pharmaceutically acceptable salt thereof, with one or more additional hormone therapy agent(s) can vary. In some alternatives, a compound of Formula (I), (II), (III), or (IV), or a pharmaceutically acceptable salt thereof, can be administered prior to all additional hormone therapy agents. In other alternatives, a compound of Formula (I), (II), (III), or (IV), or a pharmaceutically acceptable salt thereof, can be administered prior to at least one additional hormone therapy agent. In still other alternatives, a compound of Formula (I), (II), (III), or (IV), or a pharmaceutically acceptable salt thereof, can be administered concomitantly with one or more additional hormone therapy agent(s). In yet still other alternatives, a compound of Formula (I), (II), (III), or (IV), or a pharmaceutically acceptable salt thereof, can be administered subsequent to the administration of at least one additional hormone therapy agent. In some alternatives, a compound of Formula (I), (II), (III), or (IV), or a pharmaceutically acceptable salt thereof, can be administered subsequent to the administration of all additional hormone therapy agents.

In some alternatives, a subject suffering from prostate cancer is treated by surgical orchiectomy (i.e., removal of the testes). In some alternatives, a compound of Formula (I), (II), (III), or (IV), or a pharmaceutically acceptable salt thereof, can be administered after surgical orchiectomy. In some alternatives, a compound of Formula (I), (II), (III), or (IV), or a pharmaceutically acceptable salt thereof, can be administered before and after surgical orchiectomy.

In some alternatives, the compounds disclosed herein, such as a compound of Formula (I), (II), (III), or (IV), or a pharmaceutically acceptable salt thereof, or a pharmaceutical composition that includes a compound described herein, can be used in combination with one or more hormone therapy agents and in further combination with one or more statins. Statins are inhibitors of HMG-CoA reductase that can be administered to a subject to reduce testosterone/dihydrotestosterone levels. In some alternatives, a compound of Formula (I), (II), (III), or (IV), or a pharmaceutically acceptable salt thereof, or a pharmaceutical composition that includes a compound described herein, can be used in combination with one or more statins. In some alternatives, the one or more statins can be selected from among simvastatin (Zocor), atrovastatin (Lipitor), fluvastatin (Lescol), lovastatin (Mevacor, Altocor), pitavastatin (Livalo), pravastatin (Pravachol), or rosuvastatin (Crestor) or any combination thereof.

Determining and Evaluating Anti-Cancer Activity

Animal models are pivotal to further our understanding of the mechanisms of (progressive) growth of cancer. Currently used rodent tumor models; including transgenic tumor models, (using genetically modified mice susceptible to develop cancer), as well as implantation of human tumors under the skin in immunodeficient mice, do not sufficiently represent clinical cancer, especially with regard to metastasis and drug sensitivity. Preclinical tumor model systems employed to evaluate potential new treatment strategies should aim to represent the process and patterns of metastasis of their clinical counterparts as closely as possible.

A syngeneic pseudo-orthotopic in vivo model was developed to study the early steps of prostate cancer. Chambers are surgically placed into the dorsal skinfold of male mice. Briefly, male mice (25-30 g body weight) are anesthetized and placed on a heating pad. Two symmetrical titanium frames are implanted into the dorsal skinfold. A circular layer is excised from one of the skin layers. The underlying muscle and subcutaneous tissues are covered with a glass coverslip incorporated in one of the frames. After a recovery period of 2-3 days, stoma tissue and tumor cells are carefully placed in the chamber.

Tumor-derived cell lines can be grown directly in the chamber, corresponding to the traditional subcutaneous model. However, it was found that various minced tissues implanted in the chambers survive and revascularize, and that tumor-derived cell lines adapt to these various stroma after co-implantation, which points to this approach as an orthotopic model as well as a model for initial steps in metastasis.

For example, mouse prostate tissue can be grafted in the chamber. The graft develops its own vasculature and serve as orthotopic stroma for the tumor. A small number of prostate cancer cells (e.g., TRAMP-C2 cells derived from a TRAMP mouse) can be implanted on top of the prostate stroma. The tumor microenvironment can be important for the progression of different types of cancer, and orthotopic implantation of cancer cells can recapitulate human disease much more closely than subcutaneous implantation. Tumors can grow faster and develop better vasculature when the cancer cells are implanted into the relevant organ. Co-implanting mouse prostate cancer cells with prostate stroma can provide the tumor cells with an environment that better reflects the clinical disease compared to purely subcutaneous models. Re-vascularized stromal tissue and implanted tumors can remain viable for long periods of time using this method, for example, up to 90 days.

Phosphate and Tensin Homolog (PTEN) Deficient Model

Mouse cells derived from the PTEN (phosphatase and tensin homolog deleted in chromosome 10) deficient model of prostate cancer can be used to study prostate cancer. The tumor suppressor PTEN is one of the most frequently mutated genes in human prostate-cancer. Loss of PTEN can result in constitutively high PI3-kinase and Akt activities, which may lead to increased migration, invasiveness, cell proliferation and survival. Loss of PTEN can play a major role in the pathogenesis of human prostate cancer. Alteration of at least one PTEN allele is observed in approximately 60% of primary tumors. Loss of PTEN can be associated with higher Gleason scores and poor prognosis, cancer progression toward hormone-independence, resistance to chemotherapy or to radiotherapy, and bone metastasis. PTEN-deficient mice have an increased incidence of cancer, similarly to the human genetic predisposition to cancer known as Cowden syndrome, which is caused by germline mutation in the PTEN gene. In these respects, the PTEN-deficient model appears to mimic human development quite closely. Thus, heterozygous disruption of the PTEN gene can result in spontaneous development of tumors in several tissues and prostatic intraepithelial neoplasia (PIN) lesions in the prostate. Prostate-specific homozygous loss of PTEN can be sufficient to induce prostate tumors, which can progress into metastatic disease. Heterozygous loss of PTEN, on the other hand, can cause PIN with a late latency.

Germline homozygous deletion of PTEN may result in embryonic lethality due to PTEN ablation. This can be overcome through the conditional inactivation of the gene using the Cre-LoxP system. A transgenic mouse can be generated that displays expression of the Cre recombinase specifically in the epithelial cells of the prostate through the use of the prostate-specific probasin promoter (PB-Cre4 mice). By crossing these animals with mice that have floxed PTEN alleles, it can be possible to generate both heterozygous and homozygous mice in which PTEN is deleted specifically in the prostate epithelium. Progression of prostate cancer in this model is very similar to the progression of prostate cancer as observed in humans. For example, in this model epithelial hyperplasia was observed, followed by dysplasia, PIN, invasive adenocarcinoma, and finally metastases to the lymph nodes and to the lung. Similar to human cancer, the PTEN-null mice first regress following androgen ablation, and then become androgen-independent.

Epithelial cell lines can be derived from a prostate tumor dissected from a homozygous $PTEN^{L/L}$/PBCre+ mouse. At least two clonal cell lines (PTEN-P2 and PTEN-P8) are heterozygous $PTEN^{L/+}$. The remaining allele can be silenced by forced expression of the Cre recombinase in vitro (PTEN-CaP2 and PTEN-CaP8 cells). Loss of the second allele can increase anchorage-independent growth and confer tumorigenesis in vivo. Spontaneous androgen-independence can occur in vivo, even though the PTEN-CaP2 and PTEN-CaP8 cells express the androgen receptor.

The implementation of PTEN prostate cells in the animal models disclosed herein can be highly relevant to human prostate cancer, and can allow detailed observation of the growth and/or regression of prostate tumors in response to different treatment regimens. Implantation in syngeneic mice respects many aspects of normal tumor growth. For example, two pairs of mouse prostate cancer cells (PTEN-P2/8 and PTEN-CaP2/8) can facilitate examination of metastasis in a mouse model of prostate cancer that is relevant to human cancer.

IntraVital Microscopy (IVM)

IntraVital Microscopy (IVM) can be used to visualize tumors in animals and analyze various aspects of cancer physiology such as tumor vascularization, cell migration and metastasis. An advantage of IVM includes the real-time analysis of dynamic processes with single-cell resolution. IntraVital microscopy offers the possibility to follow tumor growth in a non-invasive, non-destructive manner. The application of IVM can be limited to animal models that bear visually accessible tumors. Therefore, the dorsal skinfold chamber model described above can be compatible with IVM. Using IVM can permit a number of parameters to be measured in living animals and as a function of time, including tumor growth, angiogenesis, infiltration by immune cells, tumor cell migration, mitosis (cell-division) and apoptosis (programmed cell death), all in the context of the host and in real time.

VIII. Pharmaceutical Compositions

Some alternatives described herein relate to a pharmaceutical composition, that can include a therapeutically effective amount of one or more compounds described herein, e.g., a compound of Formula (I), (II), (III), or (IV), or a pharmaceutically acceptable salt thereof, and/or a hormone therapy agent and a pharmaceutically acceptable carrier, diluent, excipient or combination thereof. In some alternatives, the pharmaceutical composition can include a single diastereomer of a compound of Formula (I), (II), (III), or (IV), or a pharmaceutically acceptable salt thereof, (for example, a single diastereomer is present in the pharmaceutical composition at a concentration of greater than 99% compared to the total concentration of the other diastereomers). In other alternatives, the pharmaceutical composition can include a mixture of diastereomers of a compound of Formula (I), (II), (III), or (IV), or a pharmaceutically acceptable salt thereof. For example, the pharmaceutical composition can include a concentration of one diastereomer of >about 50%, ≥60%, ≥70%, ≥80%, ≥90%, ≥95%, or ≥98%, as compared to the total concentration of the other diastereomers. In some alternatives, the pharmaceutical composition includes a racemic mixture of diastereomers of a compound of Formula (I), (II), (III), or (IV), or a pharmaceutically acceptable salt thereof.

Some alternatives described herein relate to a pharmaceutical composition that can include a therapeutically effective amount a compound of Formula (I), (II), (III), or (IV), an additional hormone therapy agent, and a pharmaceutically acceptable carrier, diluent, excipient or combination thereof. Some alternatives described herein relate to a pharmaceutical composition, that can include a therapeutically effective amount a compound of Formula (I), (II), (III), or (IV), and a pharmaceutically acceptable carrier, diluent, excipient or combination thereof. Some alternatives relate to a pharmaceutical composition that can include a therapeutically effective amount of a hormone therapy agent and a pharmaceutically acceptable carrier, diluent, excipient or combination thereof.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound and/or agent exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections.

One may also administer the compound and/or agent in a local rather than systemic manner, for example, via injection of the compound directly into the infected area, often in a depot or sustained release formulation. Furthermore, one may administer the compound and/or agent in a targeted drug delivery system, for example, in a liposome coated with a tissue-specific antibody. The liposomes will be targeted to and taken up selectively by the organ.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or agent described herein formulated in a compatible pharmaceutical carrier may also be prepared, placed in an appropriate container, and labeled for treatment of an indicated condition.

IX. Dosing

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials and in vitro studies.

The dosage may range broadly, depending upon the desired effects and the therapeutic indication. Alternatively, dosages may be based and calculated upon the surface area of the patient, as understood by those of skill in the art. Although the exact dosage will be determined on a drug-by-drag basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the subject. In some alternatives, an active ingredient will be administered for a period of continuous therapy, for example for a week or more, or for months or years. In some alternatives, an active ingredient can be administered one time per day.

Multiple doses of an active ingredient can be administered to a subject. For example, an active ingredient can be administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

In some alternatives, a compound of Formula (I), (II), (III) or (IV) or a pharmaceutically acceptable salt thereof, and a hormone therapy agent can be cyclically administered to a patient. Cycling therapy involves the administration of a first active ingredient for a period of time, followed by the administration of a second active ingredient for a period of time and repeating this sequential administration. Cycling therapy can reduce the development of resistance to one or more therapies, avoid or reduce the side effects of one or more therapies, and/or improve the efficacy of treatment. In some alternatives, a compound of Formula (I), (II), (III) or (IV) or a pharmaceutically acceptable salt thereof, and a hormone therapy agent are administered in a cycle of less than about 3 weeks, about once every two weeks, about once every 10 days, or about once every week. The number of cycles can be from about 1 to about 12 cycles, or from about 2 to about 10 cycles, or from about 2 to about 8 cycles.

In some alternatives, the active ingredient can be a compound of Formula (I), (II), (III), or (IV), or a pharmaceutically acceptable, salt thereof. In some alternatives, the active ingredient can be a hormone therapy agent. In some alternatives, both an active ingredient of a compound of Formula (I), (II), (III), or (IV), or a pharmaceutically acceptable salt thereof, and an active ingredient of a hormone therapy agent are administered to a subject.

The daily dosage regimen for an adult human patient may be the same or different for two active ingredients provided in combination. For example, a compound of Formula (I), (II), (III), or (IV) can be provided at a dose of between 0.01 mg and 3000 mg, while a hormone therapy agent can be provided at a dose of between 1 mg and 700 mg. The dosage or each active ingredient can be, independently, a single one or a series of two or more given in the course of one or more days, as is needed by the subject. In some alternatives, the active ingredients will be administered for a period of continuous therapy, for example for a week or more, or for months or years. In some alternatives, a compound of Formula (I), (II), (III), or (IV), or a pharmaceutically acceptable salt thereof, can be administered one time per day. In some alternatives, the hormone therapy agent can be administered once a week.

In instances where human dosages for active ingredients have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the active ingredients disclosed herein in amounts that exceed, or even far exceed, the above-stated, preferred dosage range in order to effectively and aggressively treat particularly aggressive diseases.

Dosage amount and interval may be adjusted individually to provide plasma levels of the active moiety that are sufficient to maintain the modulating effects, or minimal effective concentration (MEC). The MEC will vary for each active ingredient but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen that maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Active ingredients disclosed herein can be evaluated for efficacy and toxicity using known methods. For example, the toxicology of a particular active ingredient, or of a subset of the active ingredients, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular active ingredient may be established using several recognized methods, such as in vitro methods, animal models, or human clinical trials. When selecting a model to determine efficacy, the skilled artisan can be guided by the state of the art to choose an appropriate model, dose, route of administration and/or regime.

EXAMPLES

Additional alternatives are disclosed in further detail in the following examples, which are not in any way intended to limit the scope of the claims.

Example 1

General Procedure for Synthesis of 2-phenoxy-1,4-naphthoquinones

One millimole of 2-bromo-1,4-naphthoquinone dissolved in 20 ml of dry acetonitrile or THF was mixed with 1.2 mmol of corresponding phenol. N,N-diisopropylethylamine (1.2 mmol) was added and the mixture was refluxed for 30 minutes to 2 hours. The progress of the reaction was monitored by thin layer chromatography (TLC). Then the solvent was evaporated on a rotary evaporator and the product was purified by liquid chromatography on a silica gel column. The following compounds were synthesized according to this general procedure.

2-phenoxy-1,4-naphthoquinone (R1) (F01)

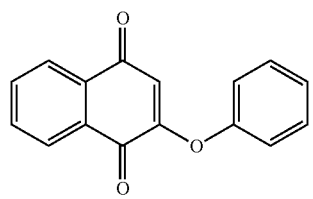 [SMILES: O=C1C=C(Oc2ccccc2)C(=O)c2ccccc21]

$^1$H NMR (500 MHz, DMSO-$d_6$), δ, ppm: 8.14-8.06 (m, 1H), 8.01-7.93 (m, 1H), 7.94-7.85 (m, 2H), 7.58-7.50 (m, 2H), 7.40-7.32 (m, 1H), 7.32-7.23 (m, 2H), 5.78 (s, 1H). ESI-MS, m/z: 251.2 [M+H]$^+$.

2-(2,3,4,5,6-pentafluorophenoxy)-1,4-naphthoquinone (R2) (F02)

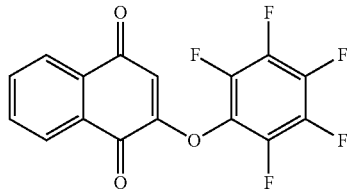 [SMILES: O=C1C=C(Oc2c(F)c(F)c(F)c(F)c2F)C(=O)c2ccccc21]

$^1$H NMR (500 MHz, DMSO-d$_6$), δ, ppm: 8.15-8.07 (m, 1H), 8.03-7.96 (m, 1H), 7.96-7.87 (m, 2H), 6.60 (t, J=1.0 Hz, 1H). ESI-MS, m/z: 340.7 [M]$^+$.

2-(4-acetamidophenoxy)-1,4-naphthoquinone (R3) (F03)

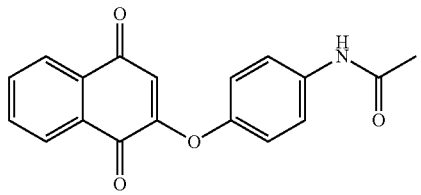 [SMILES: CC(=O)Nc1ccc(OC2=CC(=O)c3ccccc3C2=O)cc1]

$^1$H NMR (500 MHz, DMSO-d$_6$), δ, ppm: 10.10 (s, 1H), 8.13-8.05 (m, 1H), 8.00-7.93 (m, 1H), 7.93-7.84 (m, 2H), 7.74-7.67 (m, 2H), 7.24-7.17 (m, 2H), 5.77 (s, 1H), 2.06 (s, 3H). ESI-MS, m/z: 308.2 [M+H]$^+$.

2-(2,4,6-trifluorophenoxy)-1,4-naphthoquinone (R4) (F04)

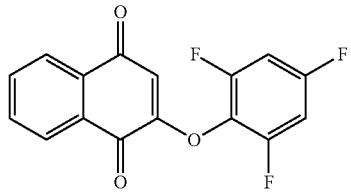 [SMILES: O=C1C=C(Oc2c(F)cc(F)cc2F)C(=O)c2ccccc21]

UV-VIS (MeOH) λ$_{max}$ (nm) (ε$_{max}$, dm$^3$·mol$^{-1}$·cm$^{-1}$): 240 (13,800), 245 (13,800), 263 (10,400), 331 (2,280). $^1$H NMR (500 MHz, DMSO-d$_6$), δ, ppm: 8.15-8.07 (m, 1H), 8.02-7.95 (m, 1H), 7.95-7.86 (m, 2H), 7.57-7.47 (m, 2H), 6.24 (d, J=1.1 Hz, 1H). ESI-MS, m/z: 327.1 [M+Na]$^+$.

2-(4-methoxyphenoxy)-1,4-naphthoquinone (R5) (F05)

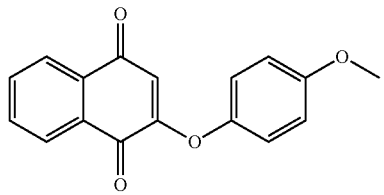 [SMILES: COc1ccc(OC2=CC(=O)c3ccccc3C2=O)cc1]

$^1$H NMR (500 MHz, DMSO-d$_6$), δ, ppm: 8.13-8.06 (m, 1H), 8.00-7.92 (m, 1H), 7.93-7.84 (m, 2H), 7.25-7.17 (m, 2H), 7.11-7.01 (m, 2H), 5.72 (s, 1H), 3.80 (s, 3H). ESI-MS, m/z: 281.3 [M+H]$^+$.

2-(4-(benzyloxy)phenoxy)-1,4-naphthoquinone (R6) (F06)

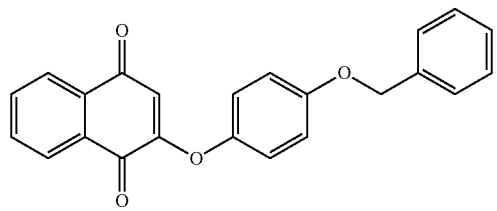 [SMILES: O=C1C=C(Oc2ccc(OCc3ccccc3)cc2)C(=O)c2ccccc21]

$^1$H NMR (500 MHz, DMSO-d$_6$), δ, ppm: 8.13-8.06 (m, 1H), 8.00-7.93 (m, 1H), 7.93-7.84 (m, 2H), 7.51-7.30 (m, 5H), 7.25-7.12 (m, 4H), 5.73 (s, 1H), 5.14 (s, 2H). ESI-MS, ink: 357.4 [M+H]$^+$.

2-(4-chloro-2-methylphenoxy)-1,4-naphthoquinone (R7) (F07)

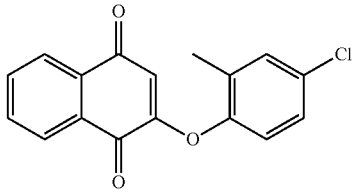 [SMILES: Cc1cc(Cl)ccc1OC1=CC(=O)c2ccccc2C1=O]

$^1$H NMR (500 MHz, DMSO-d$_6$), δ, ppm: 8.14-8.06 (m, 1H), 8.01-7.93 (m, 1H), 7.93-7.85 (m, 2H), 7.52 (dd, J=2.5, 0.9 Hz, 1H), 7.40 (dd, J=8.6, 2.6 Hz, 1H), 7.25 (d, J=8.6 Hz, 1H), 5.70 (s, 1H), 2.18 (s, 3H). ESI-MS, m/z: 298.6 [M]$^+$.

2-(3-methylphenoxy)-1,4-naphthoquinone (R8) (F08)

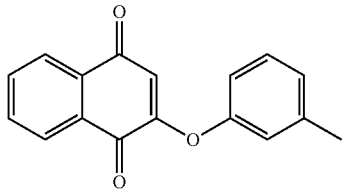 [SMILES: Cc1cccc(OC2=CC(=O)c3ccccc3C2=O)c1]

UV-VIS (MeOH) λ$_{max}$ (nm) (ε$_{max}$, dm$^3$·mol$^{-1}$·cm$^{-1}$): 241 (17,900), 245 (17,900), 267 (11,500), 327 (2,940). $^1$H NMR (500 MHz, DMSO-d$_6$), δ, ppm: 8.14-8.05 (m, 1H), 8.01-7.93 (m, 1H), 7.93-7.84 (m, 2H), 7.41 (t, J=7.8 Hz, 1H), 7.18 (ddt, J=7.7, 1.7, 0.9 Hz, 1H), 7.14-7.03 (m, 2H), 5.79 (s, 1H), 2.36 (d, J=0.8 Hz, 3H). ESI-MS, m/z: 287.1 [M+Na]$^+$.

2-(naphthalene-2-yloxy)-1,4-naphthoquinone (R9) (F09)

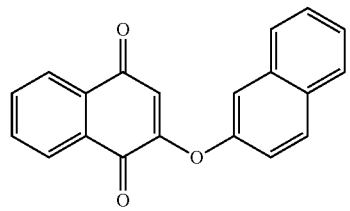 [SMILES: O=C1C=C(Oc2ccc3ccccc3c2)C(=O)c2ccccc21]

UV-VIS (MeOH) $\lambda_{max}$ (nm) ($\varepsilon_{max}$, dm$^3$·mol$^{-1}$·cm$^{-1}$): 240 (22,900), 246 (22,600), 270 (15,000), 328 (3,300). $^1$H NMR (500 MHz, DMSO-d$_6$), δ, ppm: 8.16-8.05 (m, 2H), 8.04-7.85 (m, 5H), 7.82 (d, J=2.4 Hz, 1H), 7.63-7.53 (m, 2H), 7.47 (dd, J=8.9, 2.5 Hz, 1H), 5.92 (s, 1H). ESI-MS, m/z: 301.3 [M+H]$^+$.

2-(4-hydroxyphenoxy)-1,4-naphthoquinone (R10) (F10)

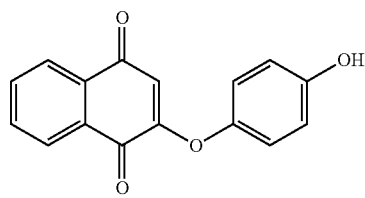 [SMILES: O=C1C=C(Oc2ccc(O)cc2)C(=O)c2ccccc21]

UV-VIS (MeOH) $\lambda_{max}$ (nm) ($\varepsilon_{max}$, dm$^3$·mol$^{-1}$·cm$^{-1}$): 240 (13,700), 245 (13,600), 272 (9,900), 330 (2,260). $^1$H NMR (500 MHz, DMSO-d$_6$), δ, ppm: 9.65 (s, 1H), 8.12-8.05 (m, 1H), 7.98-7.93 (m, 1H), 7.91-7.83 (m, 2H), 7.11-7.03 (m, 2H), 6.89-6.84 (m, 2H), 5.71 (s, 1H). ESI-MS, m/z: 267.1 [M+H]$^+$.

2-(4-(2-dimethylaminoethyl)phenoxy)-1,4-naphthoquinone (R11) (F11)

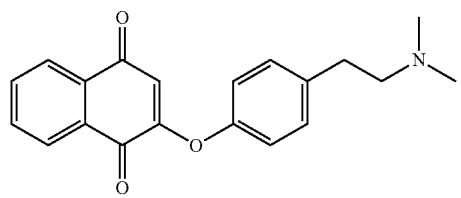 [SMILES: CN(C)CCc1ccc(OC2=CC(=O)c3ccccc3C2=O)cc1]

$^1$H NMR (500 MHz, DMSO-d$_6$), δ, ppm: 8.13-8.06 (m, 1H), 8.00-7.93 (m, 1H), 7.93-7.84 (m, 2H), 7.41-7.34 (m, 2H), 7.21-7.14 (m, 2H), 5.75 (s, 1H), 2.79-2.72 (m, 2H), 2.50-2.44 (m, 2H), 2.19 (s, 6H). ESI-MS, m/z: 322.4 [M+H]$^+$.

2-(4-nitrophenoxy)naphthalene-1,4-dione (R12) (F12)

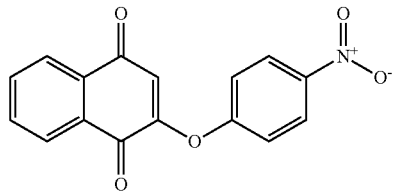 [SMILES: O=C1C=C(Oc2ccc([N+](=O)[O-])cc2)C(=O)c2ccccc21]

$^1$H NMR (500 MHz, DMSO-d$_6$), δ, ppm: 8.37-8.30 (m, 2H), 8.11-8.04 (m, 1H), 8.04-7.85 (m, 3H), 7.58-7.51 (m, 2H), 6.39 (s, 1H). ESI-MS, m/z: 295.1 [M−H]$^-$.

2-(2-benzyl-4-chlorophenoxy)naphthalene-1,4-dione (R13) (F13)

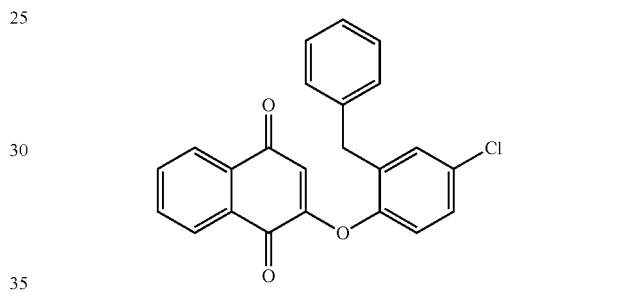

$^1$H NMR (500 MHz, DMSO-d$_6$), δ, ppm: 8.13-8.06 (m, 1H), 7.96-7.84 (m, 3H), 7.57 (d, J=2.7 Hz, 1H), 7.44 (ddd, J=8.6, 2.6, 0.9 Hz, 1H), 7.30-7.10 (m, 5H), 7.03 (tq, J=7.3, 1.2 Hz, 1H), 5.53 (d, J=0.9 Hz, 1H), 3.91 (s, 2H). ESI-MS, m/z: 375.9 [M+H]$^+$.

2-(4-chlorophenoxy)naphthalene-1,4-dione (R16) (F14)

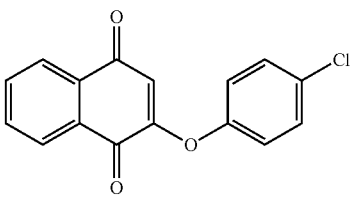 [SMILES: O=C1C=C(Oc2ccc(Cl)cc2)C(=O)c2ccccc21]

$^1$H NMR (500 MHz, DMSO-d$_6$), δ, ppm: 8.13-8.05 (m, 1H), 8.02-7.94 (m, 1H), 7.94-7.84 (m, 2H), 7.61-7.53 (m, 2H), 7.37-7.29 (m, 2H), 5.91 (s, 1H). ESI-MS, m/z: 307.7 [M+Na]$^+$.

2-(4-chloro-3-methylphenoxy)naphthalene-1,4-dione (R14) (F15)

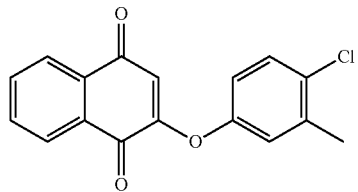 [SMILES: Cc1cc(OC2=CC(=O)c3ccccc3C2=O)ccc1Cl]

¹H NMR (500 MHz, DMSO-d₆), δ, ppm: 8.13-8.05 (m, 1H), 8.02-7.94 (m, 1H), 7.94-7.85 (m, 2H), 7.55 (d, J=8.7 Hz, 1H), 7.32 (dd, J=3.0, 0.9 Hz, 1H), 7.16 (dd, J=8.7, 2.8 Hz, 1H), 5.92 (s, 1H), 2.36 (s, 3H). ESI-MS, m/z: 321.2 [M+Na]⁺.

2-(2-chloro-4-methoxyphenoxy)naphthalene-1,4-dione (R15) (F16)

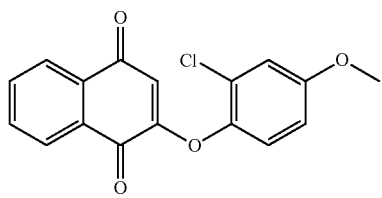 [SMILES: COc1ccc(OC2=CC(=O)c3ccccc3C2=O)c(Cl)c1]

¹H NMR (500 MHz, DMSO-d₆), δ, ppm: 8.14-8.08 (m, 1H), 8.01-7.96 (m, 1H), 7.94-7.86 (m, 2H), 7.38 (d, J=9.0 Hz, 1H), 7.27 (d, J=2.9 Hz, 1H), 7.07 (dd, J=9.0, 3.0 Hz, 1H), 5.72 (s, 1H), 3.83 (s, 3H). ESI-MS, m/z: 337.7 [M+Na]⁺.

2-(3,5-difluorophenoxy)naphthalene-1,4-dione (R17) (F17)

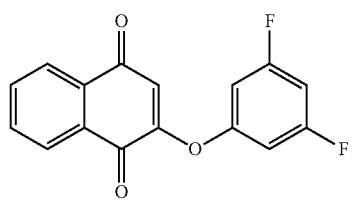 [SMILES: O=C1C=C(Oc2cc(F)cc(F)c2)C(=O)c2ccccc21]

¹H NMR (500 MHz, DMSO-d₆), δ, ppm: 8.12-8:04 (m, 1H), 8.04-7.96 (m, 1H), 7.95-7.86 (m, 2H), 7.25-7.13 (m, 3H), 6.28 (s, 1H). ESI-MS, m/z: 309.2 [M+Na]⁺.

Example 2

General Procedure for Synthesis of 2-bromo-3-phenoxy-1,4-naphthoquinones

One millimole of 2,3-dibromo-1,4-naphthoquinone dissolved in 20 ml of dry acetonitrile or THF was mixed with 1 mmol of appropriate phenol. 1 mmol of N,N-diisopropylethylamine was added and the mixture was refluxed for 30 minutes to 2 hours. The progress of the reaction was monitored by TLC. Then the solvent was evaporated on a rotary evaporator and the product was purified by liquid chromatography on a silica gel column. The following compounds were synthesized according to this general procedure.

2-bromo-3-phenoxy-1,4-naphthoquinone (Y4) (F18)

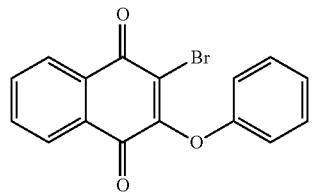 [SMILES: O=C1C(Br)=C(Oc2ccccc2)C(=O)c2ccccc21]

¹H NMR (500 MHz, DMSO-d₆), δ, ppm: 8.16-8.08 (m, 1H), 8.02-7.85 (m, 3H), 7.38-7.30 (m, 2H), 7.21-7.06 (m, 3H).

methyl 3-bromo-1,4-naphthoquinon-2-yl-salicylate (Y12) (F19)

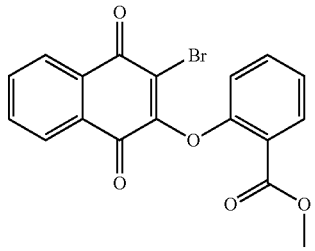 [SMILES: COC(=O)c1ccccc1OC1=C(Br)C(=O)c2ccccc2C1=O]

¹H NMR (500 MHz, DMSO-d₆), δ, ppm: 8.14-8.08 (m, 1H), 7.98-7.83 (m, 4H), 7.51 (ddd, J=8.2, 7.3, 1.8 Hz, 1H), 7.30-7.22 (m, 2H), 3.81 (s, 3H). ESI-MS, m/z: 387.2 [M]⁻.

2-bromo-3-(2,3,4,5,6-pentafluorophenoxy)-1,4-naphthoquinone (F20)

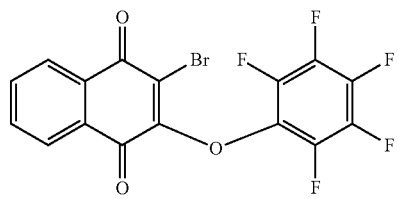 [SMILES: O=C1C(Br)=C(Oc2c(F)c(F)c(F)c(F)c2F)C(=O)c2ccccc21]

¹H NMR (500 MHz, DMSO-d₆), δ, ppm: 8.13-8.08 (m, 1H), 8.02-7.96 (m, 1H), 7.94-7.88 (m, 2H).

Example 3

General Procedure for Synthesis of 2,3-diphenoxy-1,4-naphthoquinones

One millimole of 2,3-dibromo-1,4-naphthoquinone dissolved in 30 ml of dry acetonitrile or THF was mixed with 2.5 mmol of appropriate phenol. N,N-diisopropylethylamine (2.5 mmol) was added and the mixture was refluxed for 30 minutes to 2 hours. The progress of the reaction was monitored by TLC. Then the solvent was evaporated on a rotary evaporator and the product was purified by liquid chromatography on a silica gel column. The following compounds were synthesized according to this general procedure.

2,3-diphenoxy-1,4-naphthoquinone (B9) (F21)

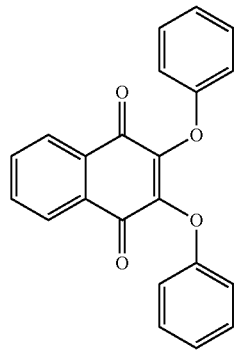 [SMILES: O=C1C(Oc2ccccc2)=C(Oc2ccccc2)C(=O)c2ccccc21]

$^1$H NMR (500 MHz, DMSO-d$_6$), δ, ppm: 8.02 (dd, J=5.7, 3.3 Hz, 2H), 7.90 (dd, J=5.7, 3.3 Hz, 2H), 7.30-7.21 (m, 4H), 7.13-6.99 (m, 6H). ESI-MS, m/z: 343.2 [M+H]$^+$.

2,3-bis(2,4,6-trifluorophenoxy)naphthalene-1,4-dione (B10) (F22)

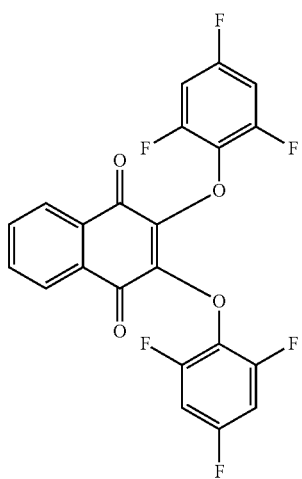 [SMILES: O=C1C(Oc2c(F)cc(F)cc2F)=C(Oc2c(F)cc(F)cc2F)C(=O)c2ccccc21]

$^1$H NMR (500 MHz, DMSO-d$_6$), δ, ppm: 8.01 (dd, J=5.7, 3.3 Hz, 2H), 7.91 (dd, J=5.7, 3.3 Hz, 2H), 7.35 (t, J=8.7 Hz, 4H).

2,3-bis(4-chloro-2-methylphenoxy)-1,4-naphthoquinone (B11) (F23)

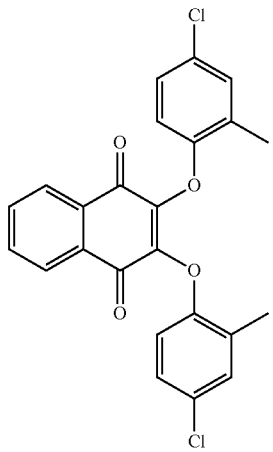 [SMILES: Cc1cc(Cl)ccc1OC1=C(Oc2ccc(Cl)cc2C)C(=O)c2ccccc2C1=O]

$^1$H NMR (500 MHz, DMSO-d$_6$), δ, ppm: 8.02 (dt, J=7.4, 3.7 Hz, 2H), 7.90 (dd, J=5.7, 3.3 Hz, 2H), 7.24 (dd, J=2.6, 1.0 Hz, 2H), 7.13 (d, J=8.7 Hz, 2H), 7.07 (dd, J=8.7, 2.6 Hz, 2H), 2.01 (s, 6H).

2,3-bis(4-hydroxyphenoxy)-1,4-naphthoquinone (B12) (F24)

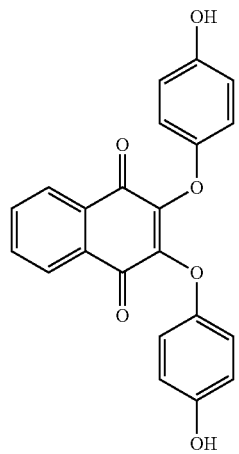 [SMILES: O=C1C(Oc2ccc(O)cc2)=C(Oc2ccc(O)cc2)C(=O)c2ccccc21]

$^1$H NMR (500 MHz, DMSO-d$_6$), δ, ppm; 9.12 (s, 214), 8.02-7.93 (m, 2H), 7.91-7.83 (m, 2H), 6.90-6.82 (m, 4H), 6.64-6.56 (m, 4H). ESI-MS, m/z: 375.3 [M+H]$^+$.

97

N,N'-(((1,4-dioxo-1,4-dihydronaphthalene-2,3-diyl)
bis(oxy))bis(4,1-phenylene))diacetamide (B14)
(F25)

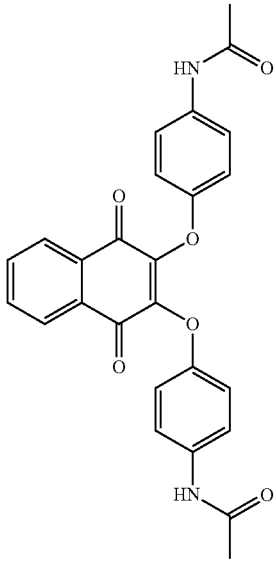 [SMILES: CC(=O)Nc1ccc(OC2=C(Oc3ccc(NC(C)=O)cc3)C(=O)c3ccccc3C2=O)cc1]

¹H NMR (500 MHz, DMSO-d₆), δ, ppm: 9.84 (s, 2H), 8.00 (dt, J=7.4, 3.7 Hz, 2H), 7.89 (dd, J=5.7, 3.3 Hz, 2H), 7.47-7.40 (m, 4H), 7.05-6.98 (m, 4H), 2.00 (s, 6H). ESI-MS, m/z: 457.4 [M+H]⁺.

2,3-bis(m-tolyloxy)naphthalene-1,4-dione (B15)
(F26)

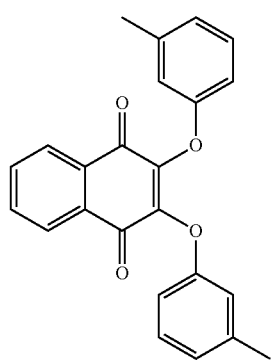 [SMILES: Cc1cccc(OC2=C(Oc3cccc(C)c3)C(=O)c3ccccc3C2=O)c1]

¹H NMR (500 MHz, DMSO-d₆), δ, ppm: 8:02 (dd, J=5.7, 3.3 Hz, 2H), 7.90 (dd, J=5.7, 3.3 Hz, 2H), 7.12 (t, J=7.9 Hz, 2H), 6.93 (t, J=2.0 Hz, 2H), 6.89-6.80 (m, 4H), 2.21 (s, 6H). ESI-MS, m/z: 371.3 [M+H]⁺.

98

2,3-bis(perfluorophenoxy)naphthalene-1,4-dione
(B16) (F27)

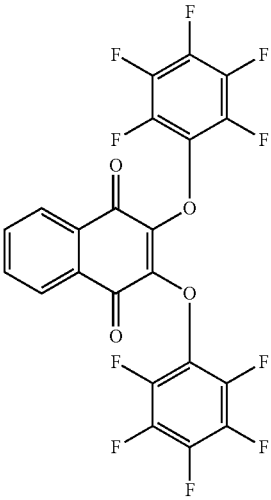 [SMILES: O=C1C(Oc2c(F)c(F)c(F)c(F)c2F)=C(Oc2c(F)c(F)c(F)c(F)c2F)C(=O)c2ccccc21]

¹H NMR (500 MHz, DMSO-d₆), δ, ppm: 8.01 (dd, J=5.8, 3.3 Hz, 2H), 7.92 (dd, J=5.8, 3.3 Hz, 2H), 3.28 (d, J=7.5 Hz, 15H). ESI-MS, m/z: 522.1 [M]⁺.

2,3-bis(4-nitrophenoxy)naphthalene-1,4-dione (B17)
(F28)

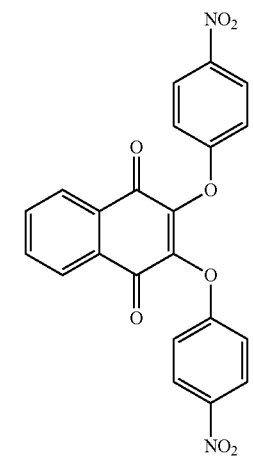 [SMILES: O=C1C(Oc2ccc([N+](=O)[O-])cc2)=C(Oc2ccc([N+](=O)[O-])cc2)C(=O)c2ccccc21]

¹H NMR (500 MHz, DMSO-d₆), δ, ppm: 8.21-8.14 (m, 4H), 8.06 (dd, J=5.7, 3.3 Hz, 2H), 7.94 (dd, J 5.7, 3.3 Hz, 2H), 7.49-7.42 (m, 4H).

| 99 | 100 |
|---|---|
| 2,3-bis(4-aminophenoxy)-1,4-naphthoquinone (F29) | 2,3-bis(4-chlorophenoxy)naphthalene-1,4-dione (F31) |

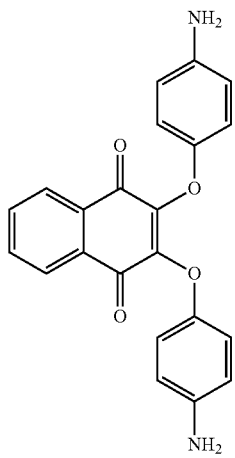

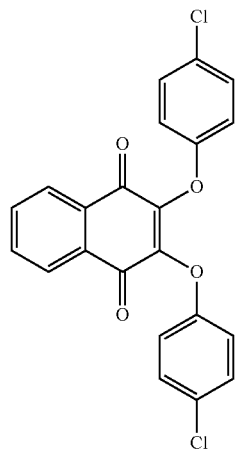

¹H NMR (500 MHz, DMSO-d₆), δ, ppm: 8.01 (dd, J=5.7, 3.3 Hz, 2H), 7.90 (dd, J=5.7, 3.3 Hz, 2H), 7.13-7.05 (m, 4H), 7.05-6.96 (m, 4H), 4.04 (s, 4H). ESI-MS, m/z: 373.3 [M+H]⁺.

¹H NMR (500 MHz, DMSO-d₆), δ, ppm: 8.02 (dd, J=5.7, 3.3 Hz, 2H), 7.90 (dd, J=5.7, 3.3 Hz, 2H), 7.35-7.27 (m, 4H), 7.20-7.12 (m, 4H). ESI-MS, m/z: 410.2 [M−H]⁻.

2,3-bis(3,5-difluorophenoxy)naphthalene-1,4-dione (F30)

2,3-bis(4-methoxyphenoxy)naphthalene-1,4-dione (F32)

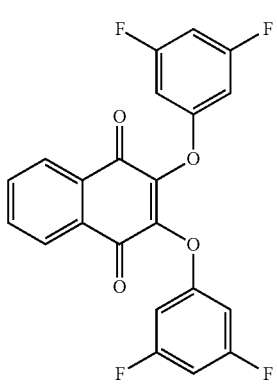 [SMILES: O=C1C(Oc2cc(F)cc(F)c2)=C(Oc2cc(F)cc(F)c2)C(=O)c2ccccc21]

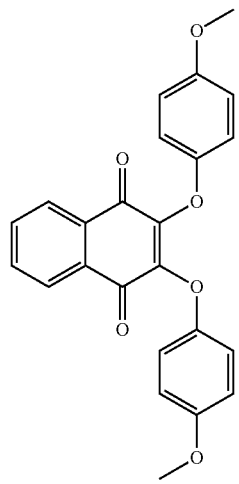 [SMILES: COc1ccc(OC2=C(Oc3ccc(OC)cc3)C(=O)c3ccccc3C2=O)cc1]

¹H NMR (500 MHz, DMSO-d₆), δ, ppm: 8.05 (dd, J=5.7, 3.3 Hz, 2H), 7.96-7.88 (m, 2H), 7.13-7.04 (m, 4H), 6.94 (tt, J=9.3, 2.3 Hz, 2H). ESI-MS, m/z: 437.2 [M+Na]⁺.

¹H NMR (500 MHz, DMSO-d₆), δ, ppm: 8.03-7.96 (m, 2H), 7.88 (dd, J=5.7, 3.3 Hz, 2H), 7.04-6.96 (m, 4H), 6.83-6.76 (m, 4H), 3.69 (d, J=0.6 Hz, 6H). ESI-MS, m/z: 403.3 [M+H]⁺.

101
2,3-bis(4-(benzyloxy)phenoxy)naphthalene-1,4-dione (F33)

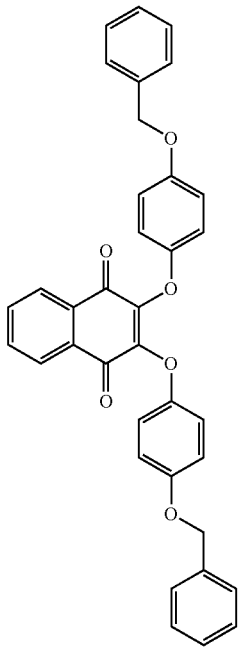 [SMILES: O=C1C(Oc2ccc(OCc3ccccc3)cc2)=C(Oc2ccc(OCc3ccccc3)cc2)C(=O)c2ccccc21]

¹H NMR (500 MHz, DMSO-d₆), δ, ppm: 8.00 (dd, J=5.7, 3.3 Hz, 2H), 7.92-7.84 (m, 2H), 7.44-7.36 (m, 8H), 7.34-7.30 (m, 2H), 7.02-6.95 (m, 4H), 6.90-6.83 (m, 4H), 5.03 (s, 4H). ESI-MS, m/z: 555.6 [M+H]⁺.

Example 4

Synthesis of 2,3-bis(4-((2-chloroethyl)carbamoyloxy)phenoxy)-1,4-naphthoquinone

To 0.25 mmol of 2,3-bis(4-hydroxyphenoxy)-1,4-naphthoquinone in 5 ml of dimethylformamide, 0.5 mmol of 2-chloroethyl isocyanate and 0.5 mmol of N,N-diisopropylethylamine was added, and the resulting mixture was stirred at room temperature for 6 hours. The product was purified by liquid chromatography on a silica column. The following compound was synthesized according to this general procedure.

102
2,3-bis(4-((2-chloroethyl)carbamoyloxy)phenoxy)-1,4-naphthoquinone (N5) (F34)

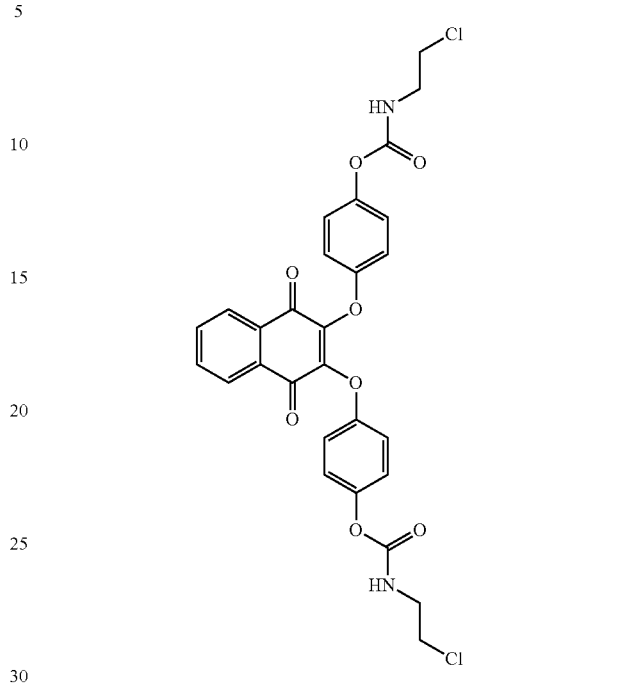

¹H NMR (500 MHz, DMSO-d₆), δ, ppm: 8.06-7.95 (m, 4H), 7.90 (dd, J=5.7, 3.3 Hz, 2H), 7.15-7.06 (m, 4H), 7.05-6.96 (m, 4H), 3.66 (t, J=6.1 Hz, 4H), 3.38 (q, J=6.0 Hz, 4H). ESI-MS, m/z: 585.9 [M]⁺.

Example 5

General Procedure for Synthesis of 2-arylamino-1,4-naphthoquinones

To 1 mmol of 1,4-naphthoquinone dissolved in 30 ml of anhydrous methanol, 0.75 mmol of corresponding arylamine was added. The mixture was stirred for 6-12 hours at 50-60° C. The solvent was evaporated on a rotary evaporator and the product was purified by liquid chromatography on a silica gel column. The following compounds were synthesized according to this general procedure.

2-(phenylamino)naphthalene-1,4-dione (W1) (F35)

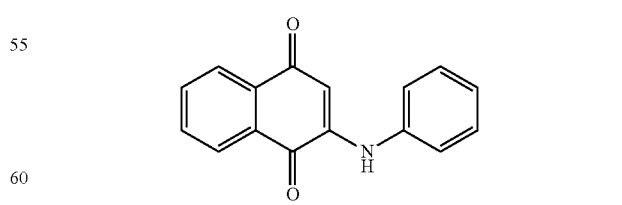

¹H NMR (500 MHz, DMSO-d₆), δ, ppm: 9.21 (s, 1H), 8.07 (dd, J=7.7, 1.3 Hz, 1H), 7.95 (dd, J=7.6, 1.3 Hz, 1H), 7.86 (td, J=7.5, 1.4 Hz, 1H), 7.79 (td, J=7.5, 1.4 Hz, 1H), 7.49-7.36 (m, 4H), 7.23 (tt, J=7.2, 1.3 Hz, 1H), 6.11 (s, 1H). ESI-MS, m/z: 272.1 [M+Na]⁺.

2-((4-(trifluoromethyl)phenyl)amino)naphthalene-1,4-dione (F59)

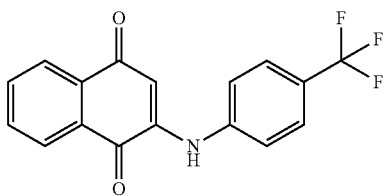 [SMILES: O=C1C=C(Nc2ccc(C(F)(F)F)cc2)C(=O)c2ccccc21]

¹H NMR (500 MHz, DMSO-d$_6$), δ, ppm: 9.45 (s, 1H), 8.08 (dd, J=7.5, 1.4 Hz, 1H), 7.97 (dd, J=7.6, 1.4 Hz, 1H), 7.92-7.85 (m, 1H), 7.85-7.75 (m, 3H), 7.63 (d, J=8.4 Hz, 2H), 6.34 (d, J=1.0 Hz, 1H). ESI-MS, m/z: 316.3 [M−H]⁻.

2-((4-(trifluoromethoxy)phenyl)amino)naphthalene-1,4-dione (F36)

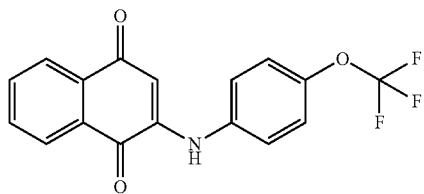 [SMILES: O=C1C=C(Nc2ccc(OC(F)(F)F)cc2)C(=O)c2ccccc21]

¹H NMR (500 MHz, DMSO-d$_6$), δ, ppm: 9.33 (s, 1H), 8.07 (dd, J=7.5, 1.4 Hz, 1H), 7.96 (dd, J=7.7, 1.4 Hz, 1H), 7.87 (td, J=7.5, 1.4 Hz, 1H), 7.80 (td, J=7.5, 1.4 Hz, 1H), 7.55-7.48 (m, 2H), 7.44 (d, J=8.6 Hz, 2H), 6.14 (s, 1H). ESI-MS, m/z: 332.3 [M−H]⁻.

2-(p-tolylamino)naphthalene-1,4-dione (F60)

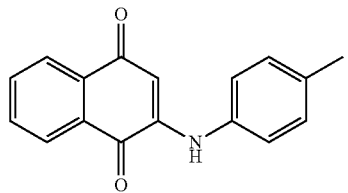 [SMILES: Cc1ccc(NC2=CC(=O)c3ccccc3C2=O)cc1]

¹H NMR (500 MHz, DMSO-d$_6$), δ, ppm: 9.17 (s, 1H), 8.06 (dd, J=7.7, 1.4 Hz, 1H), 7.94 (dd, J=7.7, 1.4 Hz, 1H), 7.85 (td, J=7.5, 1.4 Hz, 1H), 7.78 (td, J=7.5, 1.4 Hz, 1H), 7.30-7.22 (m, 4H), 6.04 (s, 1H), 2.32 (s, 3H). ESI-MS, m/z: 262.1 [M−H]⁻.

2-((3,5-difluorophenyl)amino)naphthalene-1,4-dione (F61)

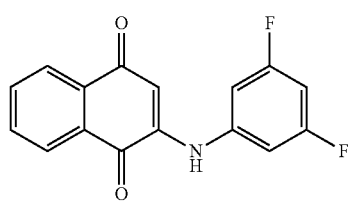 [SMILES: O=C1C=C(Nc2cc(F)cc(F)c2)C(=O)c2ccccc21]

¹H NMR (500 MHz, DMSO-d$_6$), δ, ppm: 9.36 (s, 1H), 8.07 (dd, J=7.6, 1.4 Hz, 1H), 7.97 (dd, J=7.6, 1.4 Hz, 1H), 7.88 (td, J=7.5, 1.4 Hz, 1H), 7.81 (td, J=7.5, 1.4 Hz, 1H), 7.21-7.14 (m, 2H), 7.04 (tt, J=9.3, 2.3 Hz, 1H), 6.33 (s, 1H), 3.29 (s, 1H). ESI-MS, m/z: 284.3 [M−H]⁻.

2-((4-chlorophenyl)amino)naphthalene-1,4-dione (F62)

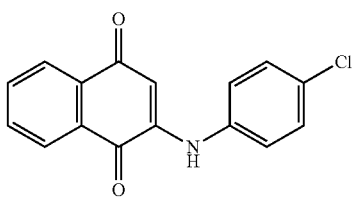 [SMILES: O=C1C=C(Nc2ccc(Cl)cc2)C(=O)c2ccccc21]

¹H NMR (500 MHz, DMSO-d$_6$), δ, ppm: 9.28 (s, 1H), 8.07 (dd, J=7.7, 1.3 Hz, 1H), 7.96 (dd, J=7.7, 1.3 Hz, 1H), 7.87 (td, J=7.5, 1.4 Hz, 1H), 7.80 (td, J=7.5, 1.4 Hz, 1H), 7.53-7.46 (m, 2H), 7.46-7.40 (m, 2H), 6.13 (s, 1H). ESI-MS, m/z: 282.7 [M−H]⁻.

N-((4-((1,4-dioxo-1,4-dihydronaphthalen-2-yl)amino)phenyl)sulfonyl)-acetamide (F63)

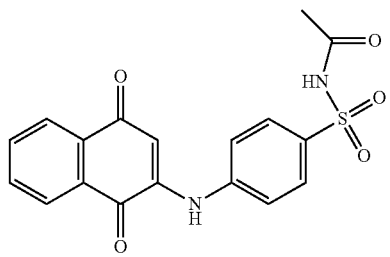 [SMILES: CC(=O)NS(=O)(=O)c1ccc(NC2=CC(=O)c3ccccc3C2=O)cc1]

¹H NMR (500 MHz, DMSO-d$_6$), δ, ppm: 12.06 (s, 1H), 9.50 (s, 1H), 8.09 (dd, J=7.7, 1.3 Hz, 1H), 7.98 (dd, J=7.6, 1.4 Hz, 1H), 7.95-7.85 (m, 3H), 7.82 (td, J=7.5, 1.4 Hz, 1H), 7.68-7.61 (m, 2H), 6.42 (s, 1H), 1.94 (s, 3H). ESI-MS, ink: 393.3 [M+Na]⁺.

4-((1,4-dioxo-1,4-dihydronaphthalen-2-yl)amino)benzenesulfonamide (F58)

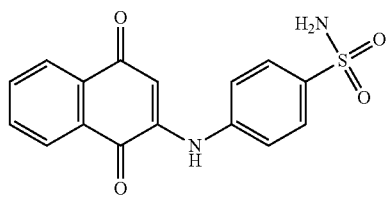 [SMILES: NS(=O)(=O)c1ccc(NC2=CC(=O)c3ccccc3C2=O)cc1]

¹H NMR (500 MHz, DMSO-d$_6$), δ, ppm: 9.43 (s, 1H), 8.08 (dd, J=7.5, 1.4 Hz, 1H), 7.97 (dd, J=7.6, 1.4 Hz, 1H), 7.92-7.77 (m, 4H), 7.62-7.56 (m, 2H), 7.34 (s, 2H), 6.32 (s, 1H). ESI-MS, m/z: 327.2 [M−H]⁻.

Example 6

General Procedure for Synthesis of 2-N-acetylamino-3-chloro-1,4-naphthoquinone 1 mmol of 2-amino-3-chloro-1,4-naphthoquinone was dispersed in 60 mmol of acetic anhydride and the mixture was stirred at room temperature. 1 drop of concentrated sulfuric acid was added as a catalyst, which lead to the formation of a yellow precipitate that was subsequently collected by vacuum filtration. The following compound was synthesized according to this general procedure.

2-N-acetylamino-3-chloro-1,4-naphthoquinone (F37)

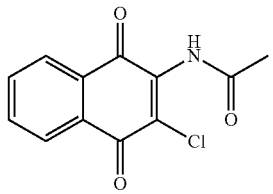 [SMILES: CC(=O)NC1=C(Cl)C(=O)c2ccccc2C1=O]

UV-VIS (MeOH) $\lambda_{max}$ (nm) ($\varepsilon_{max}$, dm$^3$·mol$^{-1}$·cm$^{-1}$): 244 (12,600), 250 (13,600), 284 (7,300), 334 (2,700). $^1$H NMR (500 MHz, DMSO-d$_6$), δ, ppm: 10.14 (s, 1H), 8.11-7.99 (m, 2H), 7.94-7.86 (m, 2H), 2.14 (s, 3H). ESI-MS, m/z: 248.6 [M–H]$^-$.

Example 7

General Procedure for Synthesis of 2-N-acetyl-3-phenoxy-1,4-naphthoquinones 1 mmol of 2-N-acetylamino-3-chloro-1,4-naphthoquinone in 30 ml of dry acetonitrile was mixed with 2.5 mmol of appropriate phenol. (N,N'-((1,4-phenylenebis(oxy))bis(1,4-dioxo-1,4-dihydronaphthalene-3,2-diyl))diacetamide was obtained using 0.5 mmol of hydroquinone and 2.5 mmol of N,N-diisopropylethylamine. The mixture was refluxed for 30 minutes to 2 hours. The progress of the reaction was monitored by TLC. The solvent was evaporated on a rotary evaporator and the product was then purified by liquid chromatography on a silica gel column. The following compounds were synthesized according to this general procedure.

N-(1,4-dioxo-3-phenoxy-1,4-dihydronaphthalen-2-yl)acetamide (F38)

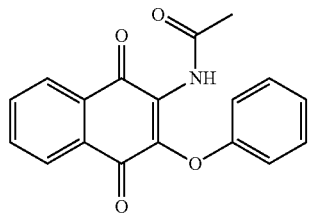 [SMILES: CC(=O)NC1=C(Oc2ccccc2)C(=O)c2ccccc2C1=O]

UV-VIS (MeOH) $\lambda_{max}$ (nm) ($\varepsilon_{max}$, dm$^3$·mol$^{-1}$·cm$^{-1}$): 249 (17,300), 278 (8,600), 330 (3,300). $^1$H NMR (500 MHz, DMSO-d$_6$), δ, ppm: 9.74 (s, 1H), 8.08-8.00 (m, 1H), 8.00-7.93 (m, 1H), 7.93-7.82 (m, 2H), 7.34-7.25 (m, 2H), 7.11-7.00 (m, 3H), 1.90 (s, 3H). ESI-MS, m/z: 308.3 [M+H]$^+$.

N-(3-(4-chlorophenoxy)-1,4-dioxo-1,4-dihydronaphthalen-2-yl)acetamide (F39)

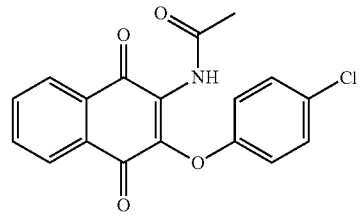 [SMILES: CC(=O)NC1=C(Oc2ccc(Cl)cc2)C(=O)c2ccccc2C1=O]

UV-VIS (MeOH) $\lambda_{max}$ (nm) ($\varepsilon_{max}$, dm$^3$·mol$^{-1}$·cm$^{-1}$): 249 (19,200), 277 (9,600), 330 (3,700). $^1$H NMR (500 MHz, DMSO-d$_6$), δ, ppm: 9.77 (s, 1H), 8.08-8.01 (m, 1H), 8.00-7.93 (m, 1H), 7.92-7.83 (m, 2H), 7.37-7.30 (m, 2H), 7.14-7.06 (m, 2H), 1.94 (s, 3H). ESI-MS, m/z: 342.7 [M+H]$^+$.

N-(4-((3-acetamido-1,4-dioxo-1,4-dihydronaphthalen-2-yl)oxy)phenyl)acetamide (F40)

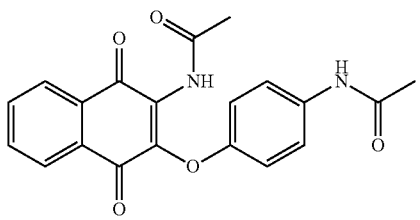 [SMILES: CC(=O)NC1=C(Oc2ccc(NC(C)=O)cc2)C(=O)c2ccccc2C1=O]

UV-VIS (MeOH) $\lambda_{max}$ (nm) ($\varepsilon_{max}$, dm$^3$·mol$^{-1}$·cm$^{-1}$): 249 (34,000), 333 (3,900). $^1$H NMR (500 MHz, DMSO-d$_6$), δ, ppm: 9.86 (s, 1H), 9.70 (s, 1H), 8.06-8.02 (m, 1H), 8.00-7.93 (m, 1H), 7.92-7.82 (m, 2H), 7.50-7.42 (m, 2H), 7.00-6.93 (m, 2H), 2.01 (s, 3H), 1.90 (s, 3H). ESI-MS, m/z: 387.3 [M+Na]$^+$.

N-(3-(4-methoxyphenoxy)-1,4-dioxo-1,4-dihydronaphthalen-2-yl)acetamide (F41)

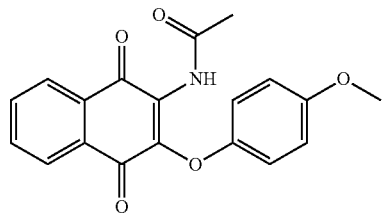 [SMILES: COc1ccc(OC2=C(NC(C)=O)C(=O)c3ccccc3C2=O)cc1]

UV-VIS (MeOH) $\lambda_{max}$ (nm) ($\varepsilon_{max}$, dm$^3$·mol$^{-1}$·cm$^{-1}$): 247 (22,400), 277 (13,200), 333 (3,700). $^1$H NMR (500 MHz, DMSO-d$_6$), δ, ppm: 9.67 (s, 1H), 8.06-8.00 (m, 1H), 7.99-7.92 (m, 1H), 7.92-7.82 (m, 2H), 7.02-6.95 (m, 2H), 6.88-6.81 (m, 2H), 3.72 (s, 3H), 1.90 (s, 3H). ESI-MS, m/z: 338.3 [M+H]$^+$.

N-(3-(4-(benzyloxy)phenoxy)-1,4-dioxo-1,4-dihydronaphthalen-2-yl)acetamide (F42)

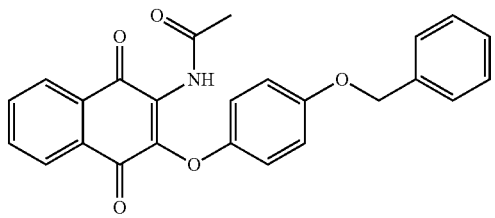 [SMILES: CC(=O)NC1=C(Oc2ccc(OCc3ccccc3)cc2)C(=O)c2ccccc2C1=O]

UV-VIS (MeOH) $\lambda_{max}$ (nm) ($\varepsilon_{max}$, dm$^3$·mol$^{-1}$·cm$^{-1}$): 245 (25,600), 277 (14,000), 333 (3,700). $^1$H NMR (500 MHz, DMSO-d$_6$), δ, ppm: 9.67 (s, 1H), 8.06-8.00 (m, 1H), 7.99-7.92 (m, 1H), 7.92-7.82 (m, 2H), 7.44 (d, J=7.2 Hz, 2H), 7.38 (dd, J=8.4, 6.7 Hz, 2H), 7.35-7.29 (m, 1H), 7.01-6.96 (m, 2H), 6.95-6.89 (m, 2H), 5.06 (s, 2H), 1.88 (s, 3H). ESI-MS, m/z: 414.4 [M+H]$^+$.

N-(3-(3,5-difluorophenoxy)-1,4-dioxo-1,4-dihydronaphthalen-2-yl)acetamide (F43)

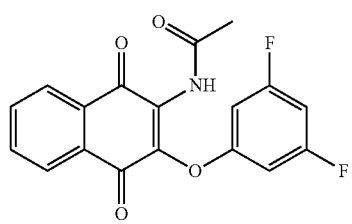 [SMILES: CC(=O)NC1=C(Oc2cc(F)cc(F)c2)C(=O)c2ccccc2C1=O]

UV-VIS (MeOH) $\lambda_{max}$ (nm) ($\varepsilon_{max}$, dm$^3$·mol$^{-1}$·cm$^{-1}$): 249 (21,000), 282 (11,200), 332 (3,900). $^1$H NMR (500 MHz, DMSO-d$_6$), δ, ppm: 9.81 (s, 1H), 8.08-8.01 (m, 1H), 8.01-7.94 (m, 1H), 7.93-7.84 (m, 2H), 6.94 (ddd, J=18.4, 9.0, 2.3 Hz, 3H), 1.99 (s, 3H). ESI-MS, m/z: 344.2 [M+H]$^+$.

N,N'-((1,4-phenylenebis(oxy))bis(1,4-dioxo-1,4-dihydronaphthalene-3,2-diyl))diacetamide (F44)

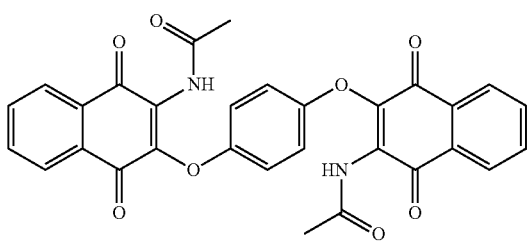 [SMILES: CC(=O)NC1=C(Oc2ccc(OC3=C(NC(C)=O)C(=O)c4ccccc4C3=O)cc2)C(=O)c2ccccc2C1=O]

UV-VIS (MeOH) $\lambda_{max}$ (nm) ($\varepsilon_{max}$, dm$^3$·mol$^{-1}$·cm$^{-1}$): 248 (26,000), 275 (13,400), 333 (4,800). $^1$H NMR (500 MHz, DMSO-d$_6$), δ, ppm: 9.74 (s, 2H), 8.08-8.00 (m, 2H), 8.00-7.92 (m, 2H), 7.92-7.82 (m, 4H), 6.98 (s, 4H), 1.95 (s, 6H). ESI-MS, m/z: 535.4 [M–H]$^-$.

Example 8

Synthesis of N-acetyl-N-(3-chloro-1,4-dioxo-1,4-dihydronaphthalen-2-yl)acetamide 0.01 mol of 2-amino-3chloro-1,4-naphthoquinone was suspended in 4 ml of acetic acid followed by addition of 0.07 mol of acetic anhydride and one drop of concentrated sulfuric acid. The reaction mixture was refluxed for 6 hours and then slowly cooled to 4° C. The precipitate was then filtered off and recrystallized from dichloromethane/methanol 3:1 to yield product.

N-acetyl-N-(3-chloro-1,4-dioxo-1,4-dihydronaphthalen-2-yl)acetamide (F45)

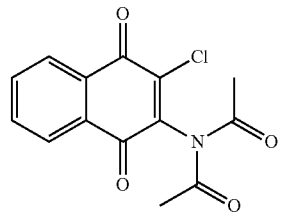 [SMILES: CC(=O)N(C(C)=O)C1=C(Cl)C(=O)c2ccccc2C1=O]

$^1$H NMR (500 MHz, DMSO-d$_6$), δ, ppm: 8.20-8.15 (m, 1H), 8.14-8.08 (m, 1H), 8.02-7.94 (m, 2H), 2.35 (s, 6H).

Example 9

Synthesis of methyl 2-((8-hydroxy-3-methyl-1,4-dioxo-1,4-dihydronaphthalen-2-yl)thio)acetate 0.8 mmol of plumbagin was dissolved in the mixture of 20 ml of methanol and 15 ml of 2-propanol. 0.8 mmol of methylthioglycolate was added, and the mixture was stifled at room temperature for 6 hours. The reaction mixture was poured into water and extracted with diethylether. The ether layer was washed twice with 10% CuSO$_4$ solution and then with water. The organic phase was then dried and concentrated on a rotary evaporator. The product was purified by column chromatography on silica gel. The following compound was synthesized according to this general procedure.

Methyl 2-((8-hydroxy-3-methyl-1,4-dioxo-1,4-dihydronaphthalen-2-yl)thio)acetate (F46)

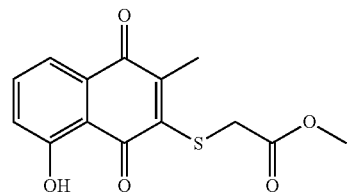 [SMILES: COC(=O)CSC1=C(C)C(=O)c2cccc(O)c2C1=O]

$^1$H NMR (500 MHz, DMSO-d$_6$), δ, ppm: 11.63 (s, 1H), 7.73 (dd, J=8.4, 7.5 Hz, 1H), 7.54 (dd, J=7.5, 1.1 Hz, 1H), 7.32 (dd, J=8.4, 1.1 Hz, 1H), 4.03 (s, 2H), 3.61 (s, 3H), 2.27 (s, 3H). ESI-MS, m/z: 293.1 [M+H]$^+$. Elemental analysis, found, %: C, 57.27; H, 4.63; S, 11.52. Calculated for C14H12O5S (292.04), %: C, 57.53; H, 4.14; S, 10.97.

Example 10

General Procedure for Synthesis of 5-alkyloxy-1,4-naphthoquinones 1 mmol of corresponding 5-hydroxy-1,4-naphthoquinone was dissolved in 10 ml of dry acetonitrile, followed by the addition of 5 mmol of appropriate allyliodide. 1 mmol of silver oxide was subsequently added. The mixture was stirred at room temperature for 6-24 hours. The progress of the reaction was monitored by thin layer chromatography (TLC) on aluminum-backed silica gel 60 F254 plates (Merck, Germany). The product was purified by liquid chromatography on silica gel using hexane/ethylacetate (4/1) as eluent. The following compounds were synthesized according to this general procedure.

5-methoxy-2-methyl-1,4-naphthoquinone (F47)

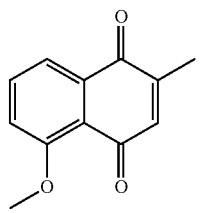

UV-VIS (MeOH) $\lambda_{max}$ (nm) ($\varepsilon_{max}$, dm$^3 \cdot$mol$^{-1} \cdot$cm$^{-1}$): 246 (16,900), 390 (4,400). $^1$H NMR (500 MHz, DMSO-d$_6$), δ, ppm: 7.77 (dd, J=8.5, 7.6 Hz, 1H), 7.61 (dd, J=7.6, 1.1 Hz, 1H), 7.52 (dd, J=8.6, 1.1 Hz, 1H), 6.78 (q, J=1.5 Hz, 1H), 3.90 (s, 3H), 2.04 (d, J=1.6 Hz, 3H). ESI-MS, m/z: 203.2 [M+H]$^+$. EA, found, %: C, 71.13; H, 5.55. Calculated for C12H10O3 (202.21), %: C, 71.28; H, 4.98.

5-(4-iodobutoxy)-2-methyl-1,4-naphthoquinone (F48)

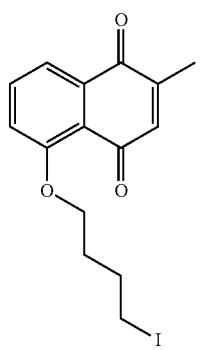 [SMILES: CC1=CC(=O)c2c(OCCCCI)cccc2C1=O]

$^1$H NMR (500 MHz, DMSO-d$_6$), δ, ppm: 7.75 (dd, J=8.5, 7.6 Hz, 1H), 7.61 (dd, J=7.6, 1.1 Hz, 1H), 7.51 (dd, J=8.6, 1.1 Hz, 1H), 6.77 (q, J=1.5 Hz, 11-1), 4.16 (t, J=6.1 Hz, 2H), 3.41 (t, J=6.9 Hz, 21-1), 2.09-1.99 (m, 5H), 1.90-1.80 (m, 2H). ESI-MS, m/z: 371.1 [M+H]$^+$. EA, found, %: C, 48.57; H, 4.35. Calculated for C15H15IO3 (370.19), %: C, 48.67; H, 4.08.

5-(3-iodopropoxy)-2-methyl-1,4-naphthoquinone (F49)

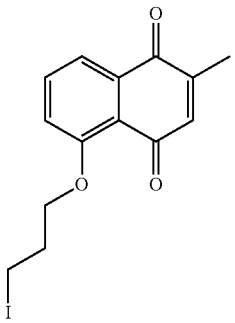 [SMILES: CC1=CC(=O)c2c(OCCCI)cccc2C1=O]

$^1$H NMR (500 MHz, DMSO-d$_6$), δ, ppm: 7.81-7.72 (m, 1H), 7.67-7.58 (m, 1H), 7.54 (dd, J=8.5, 1.1 Hz, 1H), 6.82-6.75 (m, 1H), 4.16 (t, J=5.6 Hz, 2H), 3.58 (t, J=6.8 Hz, 2H), 3.34-3.26 (m, 1H), 2.27-2.15 (m, 2H), 2.04 (d, J=1.5 Hz, 3H).

5-isopropoxy-2-methyl-1,4-naphthoquinone (F50)

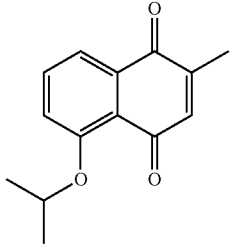 [SMILES: CC1=CC(=O)c2c(OC(C)C)cccc2C1=O]

$^1$H NMR (500 MHz, DMSO-d$_6$), δ, ppm: 7.73 (dd, J=8.5, 7.6 Hz, 1H), 7.59 (dd, J=7.7, 1.1 Hz, 1H), 7.52 (dd, J=8.5, 1.0 Hz, 1H), 6.75 (q, J=1.5 Hz, 1H), 4.75 (h, J=6.0 Hz, 1H), 2.03 (d, J=1.6 Hz, 3H), 1.32 (d, J=6.0 Hz, 6H). ESI-MS, m/z: 231.2 [M+H]$^+$.

5-methoxy-1,4-naphthoquinone (F51)

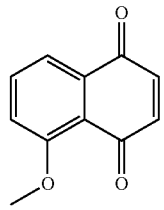

UV-VIS (MeOH) $\lambda_{max}$ (nm) ($\varepsilon_{max}$, dm$^3 \cdot$mol$^{-1} \cdot$cm$^{-1}$): 242 (19,370), 392 (4,170). $^1$H NMR (500 MHz, DMSO-d$_6$), δ, ppm: 7.81 (dd, J=8.5, 7.6 Hz, 1H), 7.62-7.53 (m, 2H), 6.99-6.91 (m, 1H), 6.92-6.85 (m, 1H), 3.92 (s, 3H).

5,8-dimethoxy-1,4-naphthoquinone (F52)

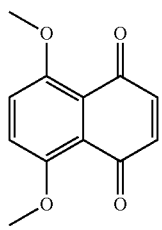 [SMILES: COc1ccc(OC)c2c1C(=O)C=CC2=O]

¹H NMR (500 MHz, DMSO-d₆), δ, ppm: 7.56 (s, 2H), 6.78 (s, 2H), 3.85 (s, 6H). ESI-MS, m/z: 219.1 [M+H]⁺.

Example 11

General Procedure for Synthesis of 2-alkyloxy-1,4-naphthoquinones 5.7 mmol of 2-hydroxy-1,4-naphthoquinone was dissolved in 50 ml of appropriate alcohol (methanol or ethanol), followed by addition of 0.8 ml of 36% HCl. The mixture was refluxed for 3-4 hours and then cooled to room temperature. The precipitate was filtered off and recrystallized from ethylacetate/methanol. The following compound was synthesized according to this general procedure.

2-ethoxy-1,4-naphthoquinone (F53)

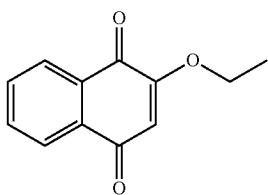

¹H NMR (500 MHz, DMSO-d₆), δ, ppm: 8.03-7.93 (m, 2H), 7.84 (dtd, J=18.0, 7.4, 1.5 Hz, 2H), 4.11 (q, J=7.0 Hz, 2H), 6.33 (s, 1H), 1.38 (t, J=7.0 Hz, 3H).

Example 12

General Procedure for Synthesis of 5-O-acetoxy-1,4-naphthoquinones 1 mmol of plumbagin in 10 ml of dichloromethane was mixed with 3 mmol of pyridine at 0° C. 2 mmol of corresponding acetyl chloride was added while the mixture was stirred at 0° C. The reaction mixture was incubated for 4 hours at room temperature then washed with water and brine. The dried organic phase was resolved by column chromatography on silica to yield the desired product. The following compounds were synthesized according to this general procedure.

6-methyl-5,8-dioxo-5,8-dihydronaphthalen-1-yl acetate (F54)

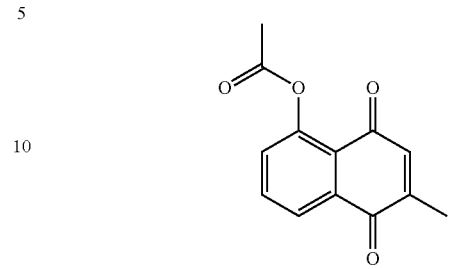

¹H NMR (500 MHz, DMSO-d₆), δ, ppm: 7.97 (dd, J=7.7, 1.3 Hz, 1H), 7.88 (t, J=7.9 Hz, 1H), 7.56 (dd, J=8.0, 1.3 Hz, 1H), 6.85 (q, J=1.5 Hz, 1H), 2.35 (s, 3H), 2.09 (s, 3H). ESI-MS, m/z: 253.2 [M+Na]⁺.

6-methyl-5,8-dioxo-5,8-dihydronaphthalen-1-yl 2-chloroacetate (F55)

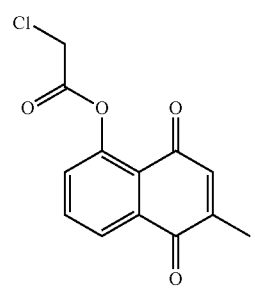 [SMILES: CC1=CC(=O)c2c(OC(=O)CCl)cccc2C1=O]

¹H NMR (500 MHz, DMSO-d₆), δ, ppm: 8.01 (dd, J=7.8, 1.3 Hz, 1H), 7.93 (t, J=7.9 Hz, 1H), 7.62 (dd, J=8.1, 1.3 Hz, 1H), 6.87 (q, J=1.5 Hz, 1H), 4.79 (s, 2H), 2.09 (s, 3H). ESI-MS, m/z: 287.4 [M+Na]⁺.

Example 13

General Procedure for Synthesis of phenylenedioxybis(1,4-naphthoquinones)

1 mmol of t-bromo-1,4-naphthoquinone dissolved in 20 ml of dry acetonitrile or THF was mixed With 0.5 mmol of corresponding hydroquinone. 1 mmol of N,N-diisopropylethylamine was added and the mixture was refluxed for 2 hours. The product was then purified by liquid chromatography on a silica gel column. The following compounds were synthesized according to this general procedure.

2,2'-(1,4-phenylenebis(oxy))bis(naphthalene-1,4-dione) (G1) (F56)

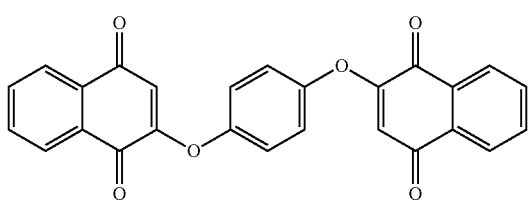 [SMILES: O=C1C=C(Oc2ccc(OC3=CC(=O)c4ccccc4C3=O)cc2)C(=O)c2ccccc21]

$^1$H NMR (500 MHz, DMSO-$d_6$), δ, ppm: 8.14-8.10 (m, 2H), 8.02-7.99 (m, 2H), 7.91 (td, J=5.3, 4.6, 3.2 Hz, 4H), 7.43 (s, 4H), 6.09 (s, 2H).

3,3'-(1,4-phenylenebis(oxy))bis(2-bromonaphthalene-1,4-dione) (G6) (F57)

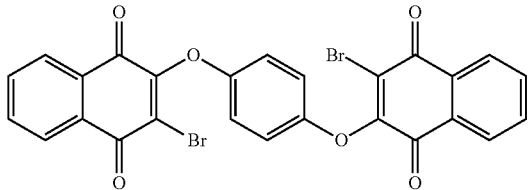 [SMILES: O=C1C(Br)=C(Oc2ccc(OC3=C(Br)C(=O)c4ccccc4C3=O)cc2)C(=O)c2ccccc21]

$^1$H NMR (500 MHz, DMSO-$d_6$), δ, ppm: 8.15-8.07 (m, 2H), 8.02-7.95 (m, 2H), 7.94-7.84 (m, 4H), 7.15 (s, 4H).

Example 14

Synthesis of 2,3-dimethoxy-1,4-naphthoquinone 0.01 mol of 2,3-dichloro-1,4-naphthoquinone and 0.03 mol of sodium methoxide were refluxed in 50 ml of anhydrous methanol for 4 hours. Then 0.02 mol of sodium methoxide was added to the reaction and the mixture was refluxed for 1 hour. The reaction mixture was concentrated in vaccuo, and the solid residue was filtered off and extensively washed with water.

2,3-dimethoxy-1,4-naphthoquinone

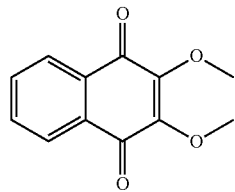 [SMILES: COC1=C(OC)C(=O)c2ccccc2C1=O]

$^1$H NMR (500 MHz, DMSO-$d_6$), δ, ppm: 7.96 (dd, J=5.7, 3.3 Hz, 2H), 7.84-7.79 (m, 2H), 3.99 (s, 6H). ESI-MS, m/z: 241.1 [M+Na]$^+$.

Example 15

Cell Culture:

PTEN-P2/GFP are cells that stably express histone H2B-GFP fusion protein. Kanda et al. (Kanda T, Sullivan K F, Wahl G M *Histone-GFP fusion protein enables sensitive analysis of chromosome dynamics in living mammalian cells. Curr Biol* 1998 Mar. 26; 8(7):377-85). These investigators developed a highly sensitive method for observing chromosome dynamics in living cells. They fused the human Histone H2B gene to the gene encoding the GFP, which was transfected into human HeLa cells to generate a stable line constitutively expressing H2B-GFP. The H2B-GFP fusion protein was incorporated into chromatin without affecting cell cycle progression. We have generated cDNA encoding a Histone H2B-GFP fusion protein under the 5'LTR in the LXRN retroviral cassette, and have introduced it into a number of humans, as well as, murine cancer cell lines by retroviral transduction.

Cells are grown in phenol red-free DMEM medium containing 10% FBS, 2 mM L-glutamine, 100 U/ml penicillin/100 µg/ml streptomycin, insulin-selenium-transferrin (5 µg/ml insulin), and DHT $10^{-8}$M final. Androgen withdrawal is achieved by not adding DHT to the medium. Cells are maintained in a humidified incubator at 37° C. and 5% $CO_2$. G418 (100 µg/ml) is added to maintain stable expression of H2B-GFP.

Cell Counting:

Cells in 12-well plates are washed once with PBS, detached using Trypsin, and transferred to a suspension vial in a final volume of 10 ml PBS. Cells are counted using a COULTER™ Multisizer II instrument (Beckman Coulter Inc., Hialeah, Fla.) gated for the appropriate cell size and corrected for particulate debris.

Animal Model and Surgical Techniques:

Animal experiments have been approved as appropriate. All surgical procedures are performed in a sterile laminar flow hood. Dorsal skinfold chambers and surgical instruments are autoclaved before use. Saline used to keep tissue moist during surgical preparation is mixed with gentamicin (50 µl/ml).

Male Nude mice (25-35 g body weight) are anesthetized (7.3 mg ketamine hydrochloride and 2.3 mg xylazine/100 g body weight, i.p.) and placed on a heating pad. Two symmetrical titanium frames are implanted into a dorsal skinfold, so as to sandwich the extended double layer of skin. A 15 mm full thickness circular layer is excised. The underlying muscle (M. cutaneous max.) and subcutaneous tissues are covered with a glass coverslip incorporated in one of the frames. After a recovery period of 2-3 days, prostate tissue and cancer cell spheroids are carefully placed in the chamber. Small circular Band Aids are applied on the backside of the chamber after surgery to prevent scratching. Before surgery, Buprenorphine (0.1 mg/kg) is given IP. After surgery Meloxicam is given in the drinking water for 4 days Meloxicam (5.0 mg/ml), is added at 35 µl per 100 ml of water to be medicated.

Preparation of Stroma:

A male donor mouse is euthanized and the anterior prostate tissue is excised, put in a Petri dish with antibiotics (gentamicin 50 µl/ml), and minced with fine scissors into small pieces (<1 mm$^2$) for implantation.

Preparation of Tumor Spheroids:

Liquid overlay plates are generated using 1% Agarose melted in DMEM that is added to round-bottom 96-well plates (50 ul/well). Cancer cells grown as pre-confluent monolayers are trypsinized, diluted to a final volume of 250,000 tumor cells/ml. Viability is determined using Trypan blue. The cells are plated at 100 ul/well into the agarose-coated plates. After 48 hours the cells form spheroids, which are picked and washed in serum-free medium before implantation into the mouse chambers. Viability is determined using Trypan blue. The size of the implanted spheroid can be determined precisely to minimize variations between animals.

Surgical Castration:

Mice are anesthetized with 7.3 mg ketamine hydrochloride and 2.3 mg xylazine/100 g body weight, i.p. A lateral incision across the scrotum is made and the testes are individually ligated and excised. The wound is cauterized. The incision is then sutured and sealed with Nexaband® acrylic.

Intravital Microscopy:

Fluorescence microscopy is performed using a Mikron Instrument Microscope equipped with epi-illuminator and video-triggered stroboscopic illumination from a xenon arc (MV-7600, EG&G). A silicon intensified target camera (SIT68, Dage-MTI) is attached to the microscope. A Hamamatsu image processor (Argus 20) with firmware version 2.50 (Hamamatsu Photonic System) is used for image enhancement and for the capture of images to a computer. A Zeiss Plan Neoflour 1.25×/0.035 objective is used to obtain an over-view of the chamber and to determine tumor size. A Zeiss A-Plan 10×/0.25 objective is used to capture images for calculation of vascular parameters. A Zeiss Achroplan 20×/0.5 W objective is used to capture images for calculation of mitotic and apoptotic indices. Our system permits evaluation of the following parameters.

Tumor area ($A_T$) is defined as number of pixels with photo density above 75 (256 gray levels), i.e., $A_T=\Sigma A_k$, for 75<k<255.

Number of Tumor Cells:

When tumors are heterogeneous, changes in $A_T$ do not directly reflect tumor growth. An estimate of the number of tumor cells ($N_{TC}$) can be obtained by fitting to a quadratic function of an intensity index, e.g. $N_{TC}=-3.296\times10^{-12}+190.6\times I_T+7.7310^{-2}\times(I_T)^2$, where the index of intensity is given by $I_T=\Sigma A_k*k$, for 75<k<255.

Mitotic and Apoptotic Indices:

At each time point, two peripheral and two central ×20 fields of the tumor are captured with a FITC filter and an integrated frame grabber. Only mitotic figures in metaphase-telophase (MI) are included in the mitotic indices to exclude the potential artifact of nuclear membrane distortion. Apoptotic/Pyknotic nuclei are defined as $H_2B$-GFP labeled nuclei with a cross sectional area <30 μm². Nuclear karyorrhexis (NK), easily distinguishable by the vesicular nuclear condensation and brightness of H2BGFP, is included within this apoptotic indices.

Image Analysis of Vascular Parameters:

For each spheroid, video recordings are used to calculate length, area and vascular density of the neovasculature being induced by the implanted tumor spheroids. Vascular parameters are analyzed from the video recording using Image-Pro Plus. Photomicrographs obtained with the ×10 objective, are "flattened" to reduce the intensity variations in the background pixels. An Area of Interest (AOI) is selected to eliminate distorted areas, and thresholding is used to segment the picture into objects and background. This panel is used to calculate the vascular area ($A_V$). The picture is skeletonized to calculate the vascular length ($L_V$). The average tumor vessel diameter $D_V$ is calculated as $A_V/L_V$, and the vascular density ($\rho_V$) is calculated as $L_V$ per tumor area. Finally, we calculate the growth rate of the total area of tumor vasculature.

Example 16

Effect of 1,4-Naphthoquinone Analogs on PTEN-P2/GFP Cell Proliferation 100 microliters of PTEN-P2/GFP prostate cancer cells were plated at a density of 8000 cells/well in 96-well plates (triplicates) in growing medium containing 10% Fetal Bovine Serum and DHT. The next day, increasing concentrations of a 1,4-naphthoquinone analog (diluted from 10 mM DMSO stock solutions) were added. DMSO used as solvent for all analogs, was kept constant through the 96-well plates. The control consisted of DMSO alone. The cells were subsequently incubated for 24 hours at 37° C. and 5% $CO_2$ in normal cell growth conditions. Cell viability was assessed by adding 9 μL/well of WST-1 reagent (Clontech), which measured mitochondrial activity of live cells. Blank control was measured from wells that do not contain cells. The incubation time was 3 hours at 37° C. Optical density of the cell samples was measured at 460 nm, by using plate reader Spectra Max 250 (Molecular Devices). The drug was determined to be cytotoxic when OD values show an inverse correlation with analog concentrations. The results are shown in TABLES 3.1-3.4, FIGS. 2A-2E, and FIGS. 3A-3D.

TABLE 3.1

Effect of 1,4-naphthoquinone analogs on PTEN-P2/GFP cell proliferation. Values are expressed as percent of control and calculated from triplicate measurements, i.e. (average OD − blank) × 100/(OD control-blank).

| Analog | Conc. (μM) | | | | | | | |
|---|---|---|---|---|---|---|---|---|
| | 0 | 1.2 | 2.5 | 5 | 7.5 | 10 | 15 | 20 |
| F04 | 100.00 | 101.28 | 100.99 | 83.33 | 17.58 | 2.09 | 1.47 | 2.64 |
| F05 | 100.00 | 102.23 | 112.56 | 56.12 | 8.83 | 1.32 | 0.77 | 3.41 |
| F06 | 100.00 | 99.82 | 99.82 | 104.65 | 106.45 | 108.06 | 99.16 | 79.89 |
| F09 | 100.00 | 117.14 | 113.83 | 105.95 | 70.05 | 28.67 | 1.97 | 3.09 |
| F12 | 100.00 | 121.91 | 117.77 | 118.43 | 117.31 | 114.53 | 78.75 | 8.27 |
| F13 | 100.00 | 129.14 | 119.36 | 60.46 | 17.48 | 1.69 | 2.19 | 2.53 |
| F14 | 100.00 | 100.03 | 92.33 | 86.23 | 71.03 | 19.23 | 1.27 | 2.30 |
| F15 | 100.00 | 95.60 | 88.97 | 97.07 | 55.47 | 4.30 | 1.67 | 2.40 |
| F16 | 100.00 | 92.80 | 97.00 | 82.50 | 12.03 | 0.73 | 1.43 | 2.30 |
| F17 | 100.00 | 97.00 | 91.77 | 88.67 | 78.23 | 71.47 | 1.07 | 2.53 |
| F22 | 100.00 | 91.17 | 103.04 | 104.80 | 106.65 | 104.44 | 104.53 | 101.46 |
| F24 | 100.00 | 111.45 | 87.12 | 57.62 | 30.95 | 8.07 | 6.73 | 3.73 |

TABLE 3.2

Effect of 1,4-naphthoquinone analogs on PTEN-P2/GFP cell proliferation. Values are expressed as percent of control and calculated from triplicate measurements, i.e. (average OD − blank) × 100/(OD control-blank).

| Analog | Conc. (µM) | | | | | | | | | |
|---|---|---|---|---|---|---|---|---|---|---|
| | 0 | 2 | 3 | 4 | 5 | 6 | 7 | 10 | 15 | 25 |
| F01 | 100 | 91.66 | 77.92 | 63.35 | 43.06 | 30.92 | 24.11 | 13.22 | 9.77 | 9.86 |
| F02 | 100 | 97.93 | 94.81 | 93.34 | 90.32 | 82.62 | 74.32 | 47.62 | 28.70 | 12.34 |
| F03 | 100 | 97.81 | 97.08 | 97.08 | 97.08 | 84.95 | 76.23 | 43.00 | 19.98 | 9.61 |
| F07 | 100 | 101.24 | 101.64 | 100.82 | 95.98 | 88.44 | 81.78 | 36.29 | 19.38 | 12.46 |
| F08 | 100 | 101.78 | 100.84 | 99.36 | 92.23 | 83.88 | 68.77 | 30.84 | 12.79 | 9.66 |
| F10 | 100 | 98.56 | 95.41 | 91.19 | 82.75 | 67.14 | 53.59 | 25.18 | 16.68 | 17.65 |
| F11 | 100 | 99.57 | 93.37 | 79.24 | 61.26 | 46.04 | 36.39 | 22.78 | 12.28 | 9.33 |
| F18 | 100 | 96.58 | 92.54 | 85.46 | 69.81 | 53.51 | 44.99 | 20.29 | 11.10 | 9.64 |
| F19 | 100 | 99.49 | 94.28 | 85.15 | 81.05 | 68.17 | 59.29 | 32.26 | 20.08 | 12.14 |
| F21 | 100 | 101.71 | 92.94 | 92.94 | 92.94 | 61.79 | 54.38 | 26.10 | 16.20 | 16.31 |
| F34 | 100 | 74.53 | 49.60 | 35.80 | 25.97 | 19.30 | 17.16 | 14.16 | 14.25 | 14.52 |
| F57 | 100 | 98.18 | 97.98 | 98.56 | 98.87 | 95.73 | 86.73 | 61.42 | 42.76 | 17.36 |

TABLE 3.3

Effect of 1,4-naphthoquinone analogs on PTEN-P2/GFP cell proliferation. Values are expressed as percent of control and calculated from triplicate measurements, i.e. (average OD − blank) × 100/(OD control-blank).

| Analog | Conc. (µM) | | | | | | | | | |
|---|---|---|---|---|---|---|---|---|---|---|
| | 0 | 2 | 3 | 4 | 5 | 6 | 7 | 10 | 15 | 25 |
| F37 | 100 | 100.87 | 94.44 | 86.58 | 71.43 | 55.72 | 36.71 | 17.65 | 13.95 | 13.58 |
| F38 | 100 | 95.76 | 86.99 | 71.65 | 54.02 | 40.95 | 30.74 | 16.58 | 14.66 | 14.29 |
| F39 | 100 | 101.60 | 82.21 | 70.56 | 57.49 | 41.52 | 29.44 | 14.26 | 12.04 | 12.66 |
| F40 | 100 | 96.95 | 98.80 | 89.21 | 85.20 | 73.18 | 67.29 | 56.18 | 46.08 | 44.62 |
| F41 | 100 | 95.08 | 89.80 | 84.52 | 75.00 | 69.62 | 63.93 | 36.93 | 13.48 | 12.64 |
| F42 | 100 | 100.96 | 101.26 | 97.56 | 89.14 | 83.76 | 75.26 | 37.49 | 20.23 | 16.60 |
| F43 | 100 | 94.63 | 88.70 | 78.33 | 68.39 | 55.27 | 45.23 | 32.85 | 24.68 | 24.07 |
| F44 | 100 | 105.78 | 101.97 | 68.98 | 58.58 | 50.49 | 45.36 | 38.74 | 20.86 | 17.13 |

TABLE 3.4

Effect of 1,4-naphthoquinone analogs on PTEN-P2/GFP cell proliferation. Values are expressed as percent of control and calculated from triplicate measurements, i.e. (average OD − blank) × 100/(OD control-blank).

| Analog | Conc. (µM) | | | | | | | | | |
|---|---|---|---|---|---|---|---|---|---|---|
| | 0 | 1 | 2 | 3 | 4 | 5 | 6 | 7 | 10 | 25 | 50 |
| F46 | 100 | 95.38 | 90.58 | 84.91 | 75.04 | 66.11 | 60.57 | 54.70 | 33.05 | 12.97 | 13.55 |
| F47 | 100 | 104.81 | 103.52 | 104.31 | 106.79 | 104.67 | 105.44 | 105.53 | 108.84 | 78.80 | 11.06 |
| F48 | 100 | 103.11 | 102.38 | 102.38 | 102.38 | 109.41 | 111.93 | 114.65 | 103.27 | 11.01 | 10.01 |
| F51 | 100 | 102.73 | 103.63 | 104.81 | 105.11 | 103.36 | 94.00 | 85.66 | 43.42 | 9.58 | 10.35 |
| F52 | 100 | 105.53 | 108.02 | 111.62 | 113.23 | 110.60 | 105.63 | 93.34 | 52.06 | 11.24 | 11.94 |
| F53 | 100 | 93.98 | 91.82 | 89.93 | 93.24 | 93.68 | 92.46 | 93.41 | 94.06 | 28.62 | 12.92 |

Example 17

Dose Response of 1,4-Naphthoquinone Analogs in Human Breast Cancer Cells SKBR-3

Figure 4:
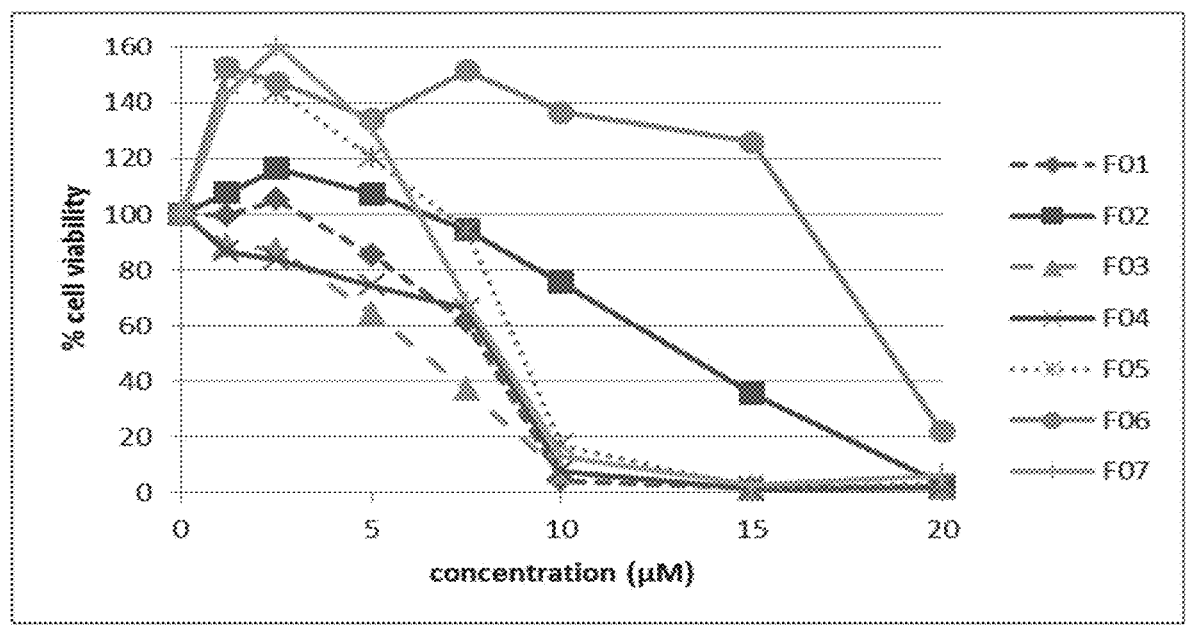
FIG. 4 illustrates the effects of 1,4-naphthoquinone analogs on the proliferation of SKBR-3 human breast cancer cells. The X axis depicts drug concentrations (μM) used in each of the treatments. The Y axis depicts the percentage of cell viability observed in each of the treatments.

100 microliters of human breast cancer SKBR-3 cells were plated at a density of 8000 cells/well in 96-well plates (triplicates) in growing medium containing 10% Fetal Bovine Serum, penicillin/streptomycin, and glutamine. The next day, increasing concentrations of a 1,4-naphthoquinone analog (diluted from 10 mM DMSO stock solutions) were added. DMSO used as solvent for all analogs, was kept constant through the 96-well plates. The control consisted of DMSO alone. The cells were subsequently incubated for 24 hours at 37° C. and 5% $CO_2$ in normal cell growth conditions. Cell viability was assessed by adding 9 µL/well of WST-1 reagent (Clontech), which measured mitochondrial activity of live cells. Blank control was measured from wells that do not contain cells. The incubation time was 3 hours at 37° C. Optical density of the cell samples was measured at 460 nm, by using plate reader Spectra Max 250 (Molecular Devices). The drug was determined to be cytotoxic when OD values show an inverse correlation with analog concentrations. The results are shown in TABLE 4, and FIG. 4.

TABLE 4

Effect of 1,4-naphthoquinone analogs on human SKBR-3 cell proliferation. Values are expressed as percent of control and calculated from triplicate measurements, i.e. (average OD − blank) × 100/(OD control-blank).

| Analog | Conc. (μM) | | | | | | | |
|---|---|---|---|---|---|---|---|---|
| | 0 | 1.2 | 2.5 | 5 | 7.5 | 10 | 15 | 20 |
| F01 | 100.00 | 99.47 | 105.05 | 85.33 | 61.15 | 4.30 | 1.90 | 2.19 |
| F02 | 100.00 | 107.66 | 116.47 | 107.37 | 94.47 | 75.45 | 35.60 | 3.02 |
| F03 | 100.00 | 88.89 | 87.44 | 64.41 | 36.88 | 7.32 | 1.24 | 1.57 |
| F04 | 100.00 | 86.74 | 83.72 | 74.38 | 65.90 | 7.52 | 1.20 | 1.90 |
| F05 | 100.00 | 151.35 | 144.41 | 120.15 | 94.14 | 17.05 | 1.91 | 2.99 |
| F06 | 100.00 | 152.32 | 147.42 | 134.16 | 151.41 | 136.66 | 125.96 | 21.95 |
| F07 | 100.00 | 143.50 | 160.12 | 131.48 | 68.35 | 12.78 | 2.70 | 6.29 |

Example 18

Dose Response of 1,4-Naphthoquinone Analogs in Human Fibrosarcoma Cells HT1080

Figure 5:
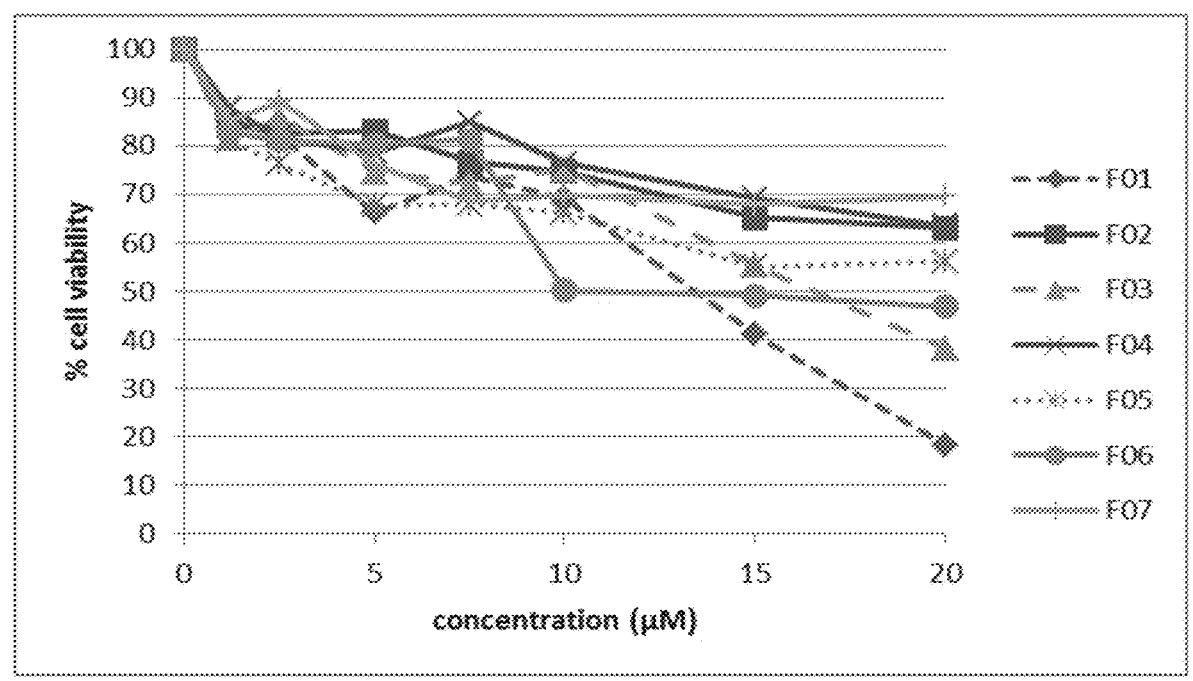
FIG. 5 illustrates the effects of 1,4-naphthoquinone analogs on the proliferation of HT1080 human fibrosarcoma cells. The X axis depicts drug concentrations (μM) used in each of the treatments. The Y axis depicts the percentage of cell viability observed in each of the treatments.

100 microliters of human fibrosarcoma HT1080 cells were plated at a density of 8000 cells/well in 96-well plates (triplicates) in growing medium containing 10% Fetal Bovine Serum, penicillin/streptomycin, and glutamine. The next day, increasing concentrations of a 1,4-naphthoquinone analog (diluted from 10 mM DMSO stock solutions) were added. DMSO used as solvent for all analogs, was kept constant through the 96-well plates. The control consisted of DMSO alone. The cells were subsequently incubated for 24 hours at 37° C. and 5% $CO_2$ in normal cell growth conditions. Cell viability was assessed by adding 9 μL/well of WST-1 reagent (Clontech), which measured mitochondrial activity of live cells. Blank control) was measured from wells that do not contain cells. The incubation time was 3 hours at 37° C. Optical density of the cell samples was measured at 460 nm, by using plate reader Spectra Max 250 (Molecular Devices). The drug was determined to be cytotoxic when OD values show an inverse correlation with analog concentrations. The results are shown in TABLE 5, and FIG. 5.

TABLE 5

Effect of 1,4-naphthoquinone analogs on the proliferation of human fibrosarcoma HT1080 cells. Values are expressed as percent of control and calculated from triplicate measurements, i.e. (average OD − blank) × 100/(OD control-blank).

| Analog | Conc. (μM) | | | | | | | |
|---|---|---|---|---|---|---|---|---|
| | 0 | 1.2 | 2.5 | 5 | 7.5 | 10 | 15 | 20 |
| F01 | 100.00 | 85.21 | 81.88 | 66.22 | 73.66 | 69.05 | 41.07 | 18.29 |
| F02 | 100.00 | 84.28 | 82.46 | 82.96 | 76.72 | 74.71 | 65.17 | 63.04 |
| F03 | 100.00 | 81.33 | 85.67 | 74.59 | 72.11 | 75.09 | 55.37 | 38.21 |
| F04 | 100.00 | 87.77 | 81.64 | 78.43 | 84.86 | 76.41 | 69.17 | 63.51 |
| F05 | 100.00 | 81.04 | 76.27 | 67.81 | 67.85 | 66.08 | 55.00 | 56.04 |
| F06 | 100.00 | 82.93 | 81.12 | 80.24 | 81.24 | 50.19 | 49.19 | 46.81 |
| F07 | 100.00 | 85.35 | 89.16 | 76.04 | 68.43 | 69.89 | 67.89 | 69.50 |

Example 19

Figure 6:
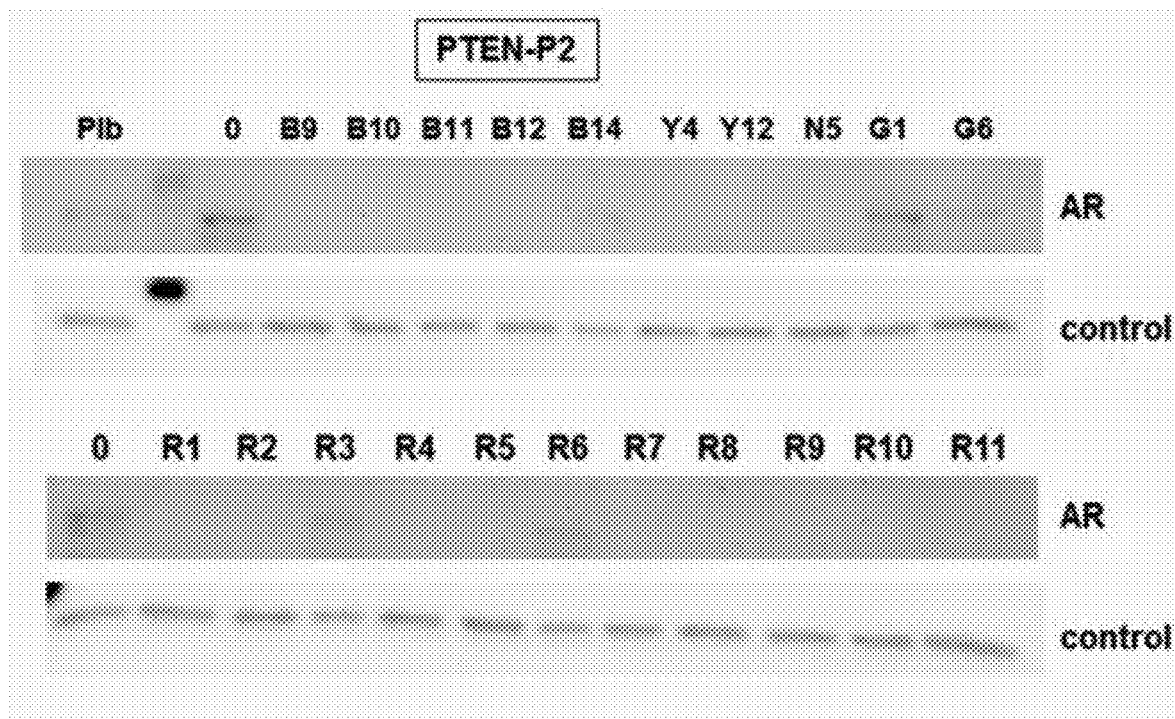
FIG. 6 summarizes results of assays of 1,4-naphthoquinone analogs for androgen receptor degradation in PTEN-P2 cells. Cells were plated in 60 mm dishes containing normal growth medium (DMEM without phenol-red, 10% FBS, penicillin/streptomycin, glutamine, Insulin-Transferrin-Selenium, DHT 10-8M). Three days after plating, analogs were individually added onto cells for 6 hours. The lanes labelled with "Plb" were cell samples treated with plumbagin. The lanes labelled with "0" were cell samples treated with a negative control solution that contained DMSO solvent only. The remaining lanes are labelled according to the analogs applied to the cells samples. All analogs were used at 20 μM, except for G1 and plumbagin that were used at 10 μM and 8 μM, respectively. Western blot analyses were performed by using anti-androgen receptor antibodies. Nitrocellulose membranes were subsequently stripped for reprobing with a loading control to ensure equal loading.

Effect of 1,4-Naphthoquinone Analogs on Androgen Receptor Degradation 1,4-Naphthoquinone analogs were assayed for androgen receptor degradation in PTEN-P2 cells. Cells were plated in 60 mm dishes containing normal growth medium (DMEM without phenol-red, 10% FBS, penicillin/streptomycin, glutamine, Insulin-Transferrin-Selenium, DHT 10-8M). Three days after plating, analogs were individually added onto cells for 6 hours. All analogs were used at 20 μM, except for G1 and plumbagin that were used at 10 μM and 8 μM, respectively. Western blot analyses were performed by using anti-androgen receptor antibodies. Nitrocellulose membranes were subsequently stripped for reprobing with loading control to ensure equal loading. The results are shown in FIG. 6.

Example 20

Figure 7:
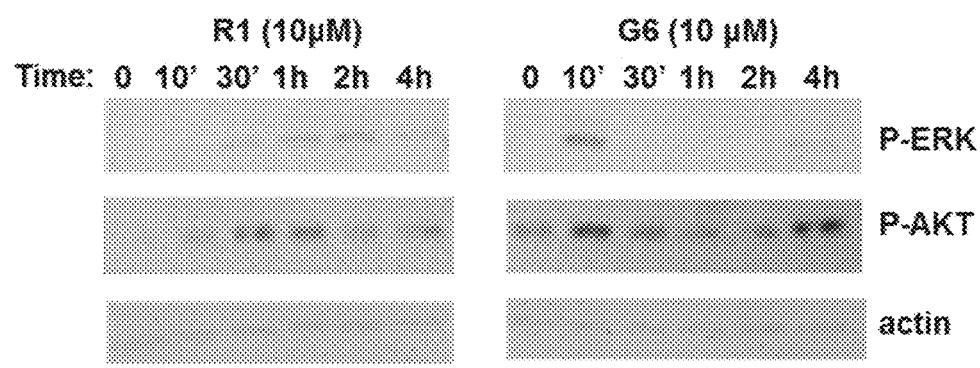
FIG. 7 shows the effect of 1,4-naphthoquinone analogs R1 and G6 on the phosphorylation of ERK and AKT in PTEN-P2 cells.

Effect of 1,4-Naphthoquinone Analogs on ERK Phosphorylation 1,4-Naphthoquinone analogs R1 and G6 were assayed for phosphorylation of ERK and AKT in PTEN-P2 cells. Cells were plated in 60 mm dishes containing normal growth medium (DMEM without phenol-red, 10% FBS, penicillin/streptomycin, glutamine, Insulin-Transferrin-Selenium, DHT 10-8M). Two days after plating, analogs R1 or G6 were added onto cells for various times ranging from 0 to 4 hours (0, 10 min, 30 min, 1 h, 2 h, 4 h) at a final concentration of 10 μM. The results are shown in FIG. 7. The lane labeled with "0" was for cells treated with DMSO solvent only. Western blot analyses were performed using anti-phospho ERK antibodies. Nitrocellulose membranes were subsequently stripped and reprobed several times with anti-phospho AKT antibodies, and finally anti-actin antibodies to ensure equal loading.

Example 21

Figure 8:
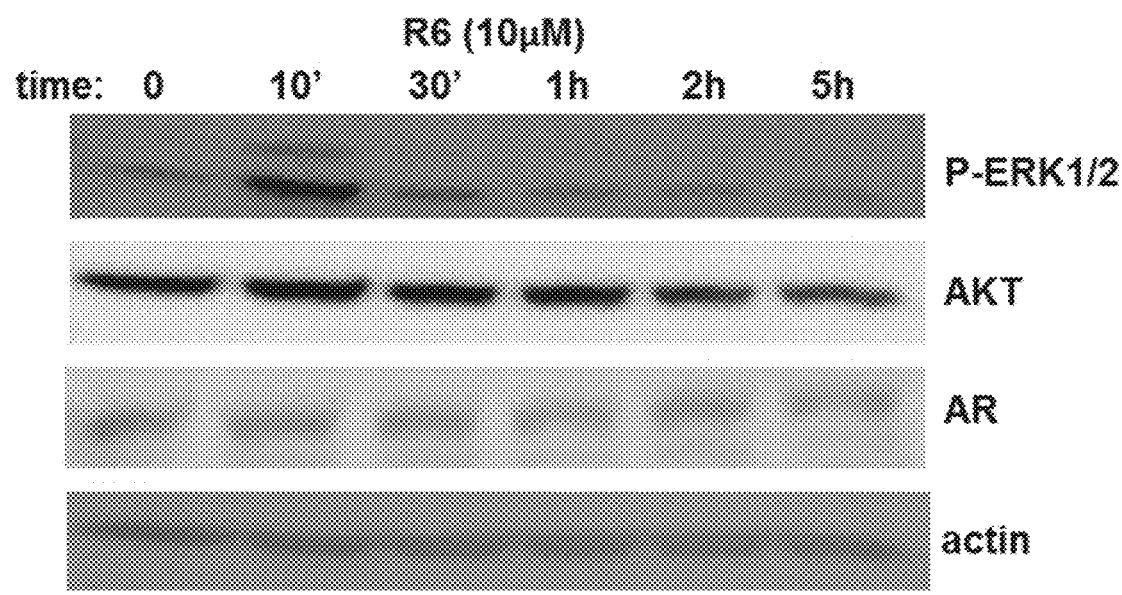
FIG. 8 shows the results of 1,4-naphthoquinone analog R6 on ERK phosphorylation and AR degradation in PTEN-P2 cells.

Effect of 1,4-Naphthoquinone Analog R6 on ERK Phosphorylation and AR Degradation 1,4-Naphthoquinone analog R6 was assayed for ERK phosphorylation and AR degradation in PTEN-P2 cells. Cells were plated in 60 mm dishes containing normal growth medium (DMEM without phenol-red, 10% FBS, penicillin/streptomycin, glutamine, Insulin-Transferrin-Selenium, DHT 10-8M). One day after plating, analog R6 was added onto cells for various times ranging from 0 to 5 hours (0, 10 min, 30 min, 1 h, 2 h, 5 h) at a final concentration of 10 μM. The results are shown in FIG. 8. The lane labeled with "0" was for cells treated with DMSO solvent only. Western blot analyses were performed using anti-phospho ERK antibodies. Nitrocellulose membranes were subsequently stripped and reprobed several times with anti-AKT, anti-androgen receptor antibodies, and finally anti-actin antibodies to ensure equal loading.

Example 22

In Vivo Effect of 1,4-Naphthoquinone Analogs Combined with Castration in the Pseudo-Orthotopic Chamber Model for Prostate Cancer Titanium chambers were surgically implanted onto the dorsal skinfold of male nu/nu mice. Two days later, minced prostate tissue from BalbC mice (syngeneic) was grafted into the chambers and allowed to vascularize for 7 to 10 days. Small tumor cells spheroids grown from PTEN-P2 tumor cells (stably transfected with H2B-GFP fusion protein (PTEN-P2/GFP)) were than implanted onto prostate tissue. When tumor vascularization was established (about 5-7 days), the animals were surgically castrated to inhibit androgen production. Surgical castration induces androgen deprivation, and is known in the art to effectively mimic clinically used hormonal/androgen ablation therapy. Treatment commenced the next day after castration.

Figure 9:
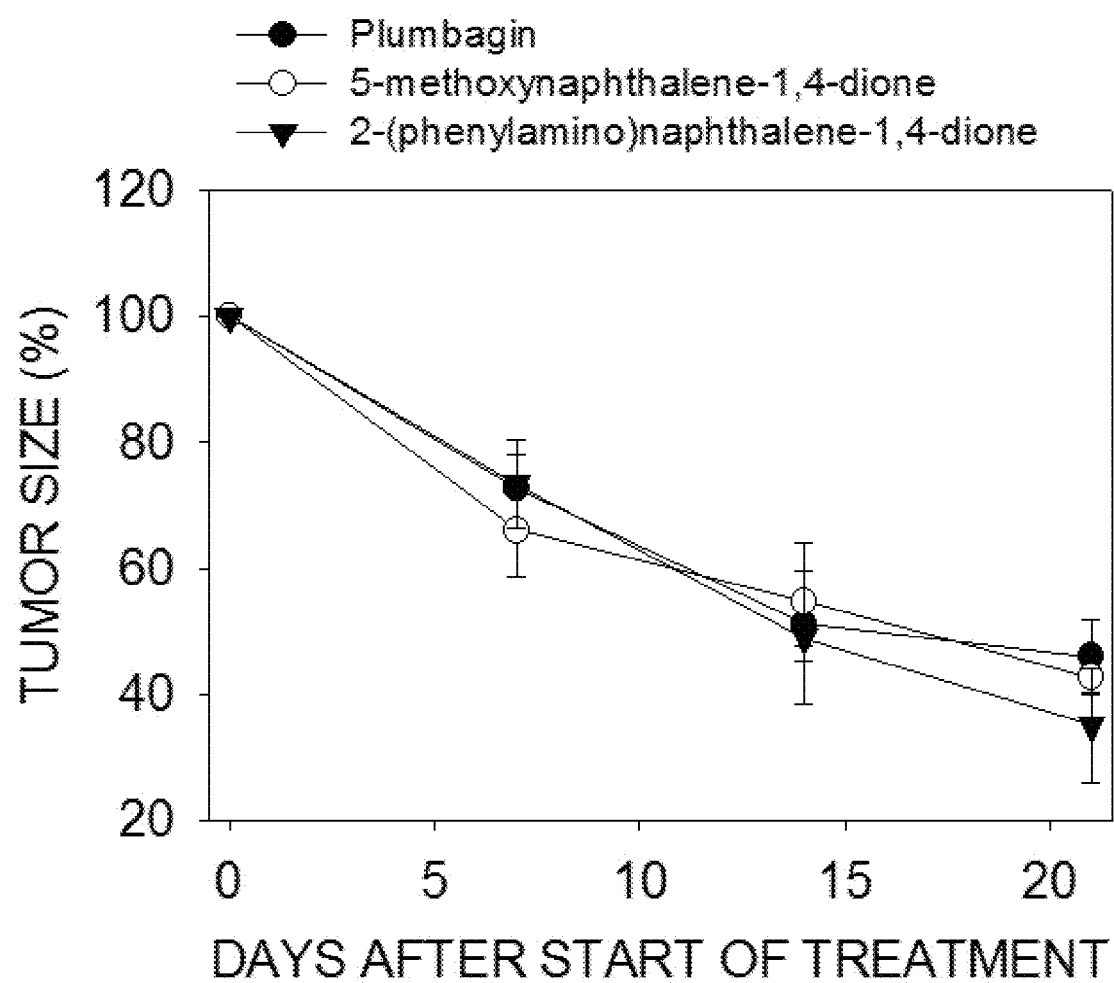
FIG. 9 shows the in vivo effect of plumbagin, 5-methoxynaphthalene-1,4-dione, and 2-(phenylamino)naphthalene-1,4-dione, given in combination with castration in a chamber mouse model of prostate cancer.

FIG. 9 shows the results of treatment of mice with plumbagin, 5-methoxynaphthalene-1,4-dione, or 2-(phenylamino)naphthalene-1,4-dione. The plumbagin, 5-methoxynaphthalene-1,4-dione, and 2-(phenylamino) naphthalene-1,4-dione (dissolved in sesame seed oil) were administered orally, once a day. The plumbagin dosage was 1 mg/kg. The 5-methoxynaphthalene-1,4-dione and 2-(phenylamino)-naphthalene-1,4-dione dosage was an equimolar dosage to 1 mg/kg of plumbagin (i.e., these compounds were dosed at 5.3 mol/kg). Day 0 is the first day of treatment with the 1,4-naphthoquinone analog.

The results indicate that the combination treatment of 5-methoxynaphthalene-1,4-dione or 2-(phenylamino)naphthalene-1,4-dione with castration was more efficient in vivo than treatment with plumbagin and castration. Therefore, this experiment provides an important indication that castration (whether surgical or chemical) in combination with 5-methoxynaphthalene-1,4-dione or 2-(phenylamino)naphthalene-1,4-dione can provide a significant improvement over therapies that were previously known in the art.

Figure 10:
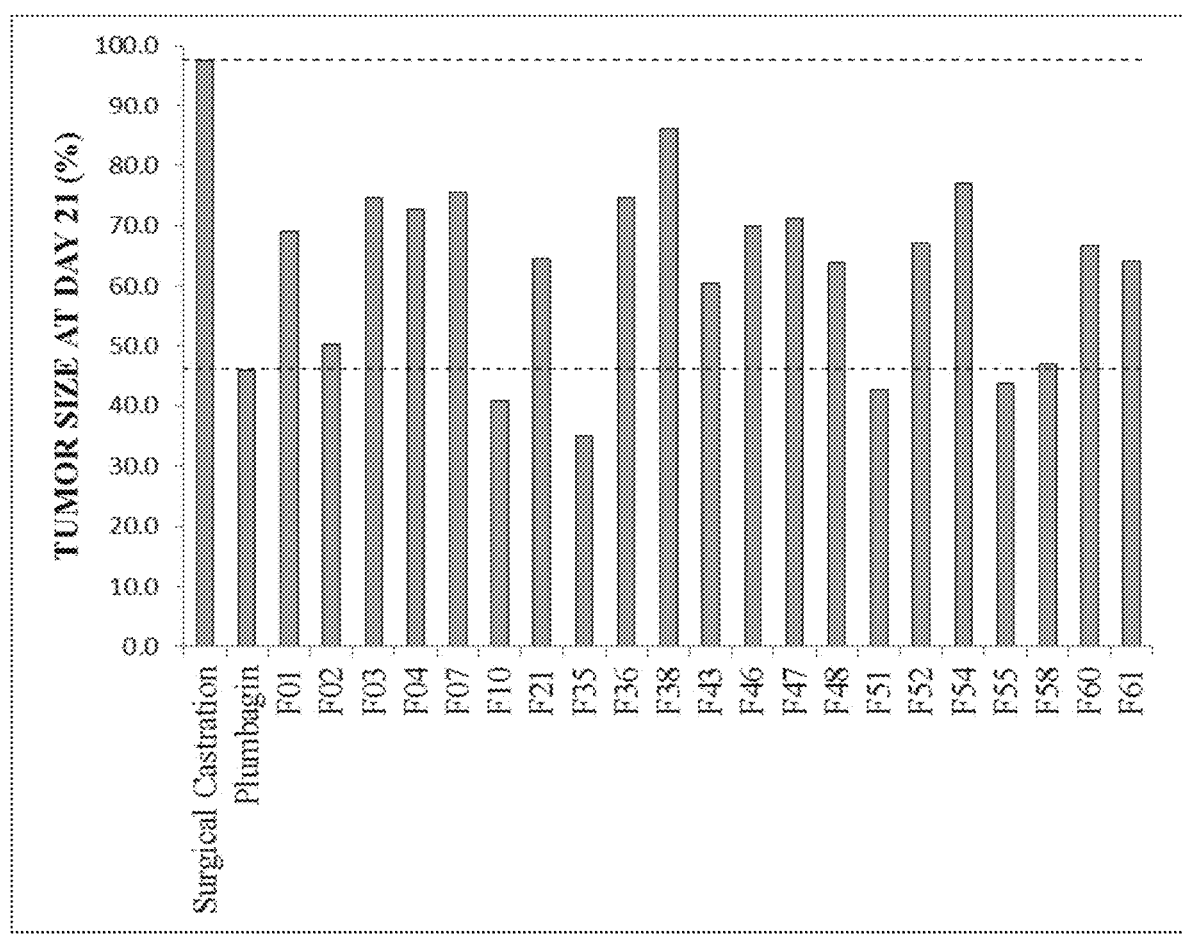
FIG. 10 shows the in vivo effect of plumbagin and several 1,4-naphthoquinone analogs, given in combination with castration in a chamber mouse model of prostate cancer after 20 days of treatment.

TABLE 6 and FIG. 10 show the results of treatment of mice with plumbagin, and several 1,4-naphthoquinone analogs disclosed herein, after 20 days of treatment. Treatments were administered orally, once daily. The plumbagin dosage was 1 mg/kg. The 1,4-naphthoquinone analogs were dosed at an equimolar dosage to 1 mg/kg of plumbagin (i.e., these compounds were dosed at 5.3 μmol/kg). Day 0 is the first day of treatment with plumbagin or the 1,4-naphthoquinone analogs. TABLE 6 and FIG. 10 also include control experiments ran with no treatment and with just surgical castration.

TABLE 6

Effect of 1,4-naphthoquinone analogs on the proliferation of H2B-GFP-PTEN-P2 tumor cells after 20 days of treatment. Values are expressed as the mean tumor size percent calculated from triplicate measurements (MEAN), along with the standard error of the mean (SEM).

| Analog | Description | MEAN (%) | SEM |
|---|---|---|---|
| n/a | no treatment (control) | 376.1 | 72.9 |
| n/a | surgical castration | 97.6 | 9.9 |
| n/a | plumbagin | 46.1 | 5.9 |
| F01 | 2-phenoxy-1,4-naphthoquinone | 69.1 | 1.5 |

TABLE 6-continued

Effect of 1,4-naphthoquinone analogs on the proliferation of H2B-GFP-PTEN-P2 tumor cells after 20 days of treatment. Values are expressed as the mean tumor size percent calculated from triplicate measurements (MEAN), along with the standard error of the mean (SEM).

| Analog | Description | MEAN (%) | SEM |
|---|---|---|---|
| F02 | 2-(2,3,4,5,6-pentafluorophenoxy)-1,4-naphthoquinone | 50.3 | 4.5 |
| F03 | 2-(4-acetamidophenoxy)-1,4-naphthoquinone | 74.6 | 15.5 |
| F04 | 2-(2,4,6-trifluorophenoxy)-1,4-naphthoquinone | 72.8 | 2.3 |
| F07 | 2-(4-chloro-2-methylphenoxy)-1,4-naphthoquinone | 75.6 | 1.7 |
| F10 | 2-(4-hydroxyphenoxy)-1,4-naphthoquinone | 40.7 | 3.2 |
| F21 | 2,3-diphenoxy-1,4-naphtho quinone | 64.7 | 2.4 |
| F35 | 2-(phenylamino)naphthalene-1,4-dione | 35.1 | 8.9 |
| F36 | 2-(4-(trifluoromethoxy)phenylamino)naphthalene-1,4-dione | 74.7 | 5.2 |
| F38 | N-(1,4-dioxo-3-phenoxy-1,4-dihydronaphthalen-2-yl)acetamide | 86.1 | 4.7 |
| F43 | N-(3-(3,5-difluorophenoxy)-1,4-dioxo-1,4-dihydronaphthalen-2-yl)acetamide | 60.4 | 2.2 |
| F46 | methyl 24(8-hydroxy-3-methyl-1,4-dioxo-1,4-dihydronaphthalen-2-yl)thio)acetate | 70.0 | 6.6 |
| F47 | 5-methoxy-2-methyl-1,4-naphthoquinone | 71.2 | 9.1 |
| F48 | 5-(4-iodopropoxy)-2-methyl-1,4-naphthoquinone | 63.9 | 7.6 |
| F51 | 5-methoxy-1,4-naphthoquinone | 42.8 | 2.7 |
| F52 | 5,8-dimethoxy-1,4-naphthoquinone | 67.2 | 4.0 |
| F54 | 6-methyl-5,8-dioxo-5,8-dihydronaphthalen-1-yl acetate | 77.0 | 11.7 |
| F55 | 6-methyl-5,8-dioxo-5,8-dihydronaphthalen-1-yl 2-chloroacetate | 43.8 | 2.2 |
| F58 | 4-((1,4-dioxo-1,4-dihydronaphthalen-2-yl)amino)benzenesulfonamide | 47.0 | 1.8 |
| F60 | 2-(p-tolylamino)naphthalene-1,4-dione | 66.8 | 6.1 |
| F61 | 2-((3,5-difluorophenyl)amino)naphthalene-1,4-dione | 64.1 | 5.4 |
| F62 | 2-((4-chlorophenyl)amino)naphthalene-1,4-dione | 144.9 | 9.8 |

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A method of inhibiting the growth of prostate cancer, comprising administering to a subject having prostate cancer a therapeutically effective amount of a compound of Formula (I) or a pharmaceutically acceptable salt thereof:

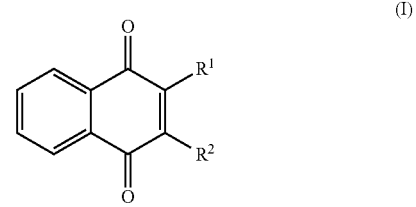

(I)

wherein:
$R^1$ is 4-hydroxyphenoxy;
$R^2$ is hydrogen;
wherein the growth of prostate cancer is inhibited; and, optionally,
wherein the composition comprising a compound of Formula (I) is administered to the subject in combination with, subsequent to, or concomitantly with, an androgen deprivation therapy.

2. The method of claim 1, wherein said androgen deprivation therapy is surgical orchiectomy.

3. The method of claim 1, wherein said androgen deprivation therapy is administration of one or more agents selected from the group consisting of cyproterone acetate, abiraterone, finasteride, flutamide, nilutamide, bicalutamide, diethylstilbestrol (DES), megestrol acetate, fosfestrol, estramustine phosphate, leuprolide, triptorelin, goserelin, histrelin, buserelin, abarelix, degarelix, orteronel, seviteronel (VT-464), enzalutamide, apalutamide (ARN-509), vinclozolin, galeterone, ketoconazole, 17-(5'-isoxazolyl)androsta-4,16-dien-3-one (L-39), aminoglutethimide, prochloraz, dutasteride, izonsteride, turosteride, episteride, genisterin, gossypol, equol, 18β-glycyrrhetinic acid, atraric acid, N-butylbenzene-sulfonamide, 3,3'-diindolylmethane, deslorelin, nafarelin, cetrorelix, and ganirelix.

4. The method of claim 1, wherein said androgen deprivation therapy reduces the production of testosterone or inhibits the conversion of testosterone to dihydrotestosterone (DHT).

5. The method of claim 1, wherein said androgen deprivation therapy is administration of one or more agents selected from the group consisting of abiraterone, finasteride, diethylstilbestrol (DES), megestrol acetate, fosfestrol, leuprolide, triptorelin, goserelin, histrelin, buserelin, abarelix, degarelix, orteronel, VT-464, ketoconazole, L-39, aminoglutethimide, prochloraz, dutasteride, izonsteride, turosteride, episteride, equol, deslorelin, nafarelin, cetrorelix, and ganirelix.

6. The method of claim 5, wherein said androgen deprivation therapy is administration of one or more agents selected from the group consisting of abiraterone, leuprolide, degarelix, and dutasteride.

7. The method of claim 1, wherein the androgen deprivation therapy decreases the subject's serum testosterone level to about 1-2%, 2-4%, 1-5%, 4-6%, 4-8%, or 5-10% of a healthy male subject.

8. The method of claim 1, wherein the androgen deprivation therapy decreases the subject's serum testosterone level to at least about ≤20 ng/dL.

9. A product combination that inhibits prostate cancer in a subject, wherein the product combination comprises a compound of Formula (I), or a pharmaceutically acceptable salt thereof, and a hormone therapy agent; and wherein the compound of Formula (I) has the following structure:

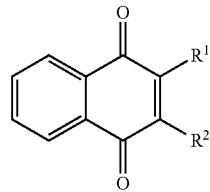

(I)

wherein:
$R^1$ is 4-hydroxyphenoxy; and
$R^2$ is hydrogen.

10. The product combination of claim 9, wherein said hormone therapy agent comprises one or more agents selected from the group consisting of cyproterone acetate, abiraterone, finasteride, flutamide, nilutamide, bicalutamide, diethylstilbestrol (DES), megestrol acetate, fosfestrol, estramustine phosphate, leuprolide, triptorelin, goserelin, histrelin, buserelin, abarelix, degarelix, orteronel, seviteronel (VT-464), enzalutamide, apalutamide (ARN-509), vinclozolin, galeterone, ketoconazole, 17-(5'-isoxazolyl)androsta-4,16-dien-3-one (L-39), aminoglutethimide, prochloraz, dutasteride, izonsteride, turosteride, episteride, genisterin, gossypol, equol, 18β-glycyrrhetinic acid, atraric acid, N-butylbenzene-sulfonamide, 3,3'-diindolylmethane, deslorelin, nafarelin, cetrorelix, and ganirelix.

11. The product combination of claim 9, wherein said hormone therapy agent reduces the production of testosterone or inhibits the conversion of testosterone to dihydrotestosterone (DHT).

12. The product combination of claim 9, wherein said hormone therapy agent comprises one or more agents selected from the group consisting of abiraterone, finasteride, diethylstilbestrol (DES), megestrol acetate, fosfestrol, leuprolide, triptorelin, goserelin, histrelin, buserelin, abarelix, degarelix, orteronel, VT-464, ketoconazole, L-39, aminoglutethimide, prochloraz, dutasteride, izonsteride, turosteride, episteride, equol, deslorelin, nafarelin, cetrorelix, and ganirelix.

13. The product combination of claim 10, wherein said hormone therapy agent comprises one or more agents selected from the group consisting of abiraterone, leuprolide, degarelix, and dutasteride.

* * * * *